US009777261B2

(12) United States Patent
Kim et al.

(10) Patent No.: US 9,777,261 B2
(45) Date of Patent: Oct. 3, 2017

(54) GLYCOSYLATED VEGF DECOY RECEPTOR FUSION PROTEIN

(71) Applicant: Korea Advanced Institute of Science and Technology (KAIST), Daejeon (KR)

(72) Inventors: Ho Min Kim, Daejeon (KR); Jung-Eun Lee, Daejeon (KR); Chan Kim, Daejeon (KR); Gou Young Koh, Daejeon (KR); Gyun Min Lee, Daejeon (KR)

(73) Assignee: Korea Advanced Institute of Science and Technology (KAIST), Yuseong-gu, Daejeon (KR)

( * ) Notice: Subject to any disclaimer, the term of this patent is extended or adjusted under 35 U.S.C. 154(b) by 23 days.

(21) Appl. No.: 14/740,158

(22) Filed: Jun. 15, 2015

(65) Prior Publication Data

US 2016/0032259 A1 Feb. 4, 2016

Related U.S. Application Data

(63) Continuation of application No. PCT/IB2015/000674, filed on Mar. 17, 2015.

(60) Provisional application No. 61/954,911, filed on Mar. 18, 2014.

(51) Int. Cl.

| | |
|---|---|
| ***A61K 38/16*** | (2006.01) |
| ***A61K 38/17*** | (2006.01) |
| ***C12N 9/12*** | (2006.01) |
| ***C07K 14/71*** | (2006.01) |
| ***C07K 16/00*** | (2006.01) |
| ***A61K 33/24*** | (2006.01) |
| ***A61K 38/45*** | (2006.01) |
| ***A61K 39/395*** | (2006.01) |
| *A61K 38/00* | (2006.01) |
| *A61K 48/00* | (2006.01) |
| *A61K 39/00* | (2006.01) |

(52) U.S. Cl.

CPC ................ *C12N 9/12* (2013.01); *A61K 33/24* (2013.01); *A61K 38/45* (2013.01); *A61K 39/395* (2013.01); *C07K 14/71* (2013.01); *C07K 16/00* (2013.01); *A61K 38/00* (2013.01); *A61K 48/00* (2013.01); *A61K 2039/505* (2013.01); *C07K 2319/30* (2013.01); *C07K 2319/32* (2013.01); *C07K 2319/70* (2013.01); *C07K 2319/91* (2013.01); *C12Y 207/10001* (2013.01)

(58) Field of Classification Search

None

See application file for complete search history.

(56) References Cited

U.S. PATENT DOCUMENTS

2005/0232925 A1* 10/2005 Sukhatme ............ A61K 31/401 424/155.1
2010/0254978 A1* 10/2010 Lawson ............. C07K 16/2878 424/133.1

OTHER PUBLICATIONS

Lee, Jung-Eun;Novel Glycosylated VEGF Decoy Receptor Fusion Protein, VEGF-Grab, Efficiently Suppresses Tumor Angiogenesis and Progression. Molecular Cancer Therapeutics,14(2) Feb. 2015.*
Ferrara N, Alitalo K. Clinical applications of angiogenic growth factors and their inhibitors. Nature medicine 1999;5 (12):1359-64.
Sung HK, Michael IP, Nagy A. Multifaceted role of vascular endothelial growth factor signaling in adult tissue physiology: an emerging concept with clinical implications. Current opinion in hematology 2010;17(3):206-12.
Egeblad M, Nakasone ES, Werb Z. Tumors as organs: complex tissues that interface with the entire organism. Developmental cell 2010;18(6):884-901.
Olsson AK, Dimberg A, Kreuger J, Claesson-Welsh L. VEGF receptor signalling—in control of vascular function. Nature reviews Molecular cell biology 2006;7(5):359-71.
Ferrara N, Hillan KJ, Gerber HP, Novotny W. Discovery and development of bevacizumab, an anti-VEGF antibody for treating cancer. Nature reviews Drug discovery 2004;3(5):391-400.
Holash J, Davis S, Papadopoulos N, Croll SD, Ho L, Russell M, et al. VEGF-Trap: a VEGF blocker with potent antitumor effects. Proceedings of the National Academy of Sciences of the United States of America 2002;99 (17):11393-8.
Shibuya M. Vascular endothelial growth factor and its receptor system: physiological functions in angiogenesis and pathological roles in various diseases. Journal of biochemistry 2013;153(1):13-9.
Sullivan LA, Carbon JG, Roland CL, Toombs JE, Nyquist-Andersen M, Kavlie A, et al. r84, a novel therapeutic antibody against mouse and human VEGF with potent anti-tumor activity and limited toxicity induction. PloS one 2010;5(8):e12031.
Bergers G, Hanahan D. Modes of resistance to anti-angiogenic therapy. Nature reviews Cancer 2008;8(8):592-603.
Potente M, Gerhardt H, Carmeliet P. Basic and therapeutic aspects of angiogenesis. Cell 2011;146(6):873-87.
Mancuso MR, Davis R, Norberg SM, O'Brien S, Sennino B, Nakahara T, et al. Rapid vascular regrowth in tumors after reversal of VEGF inhibition. The Journal of clinical investigation 2006;116(10):2610-21.
Pascolini D, Mariotti SP, Pokharel GP, Pararajasegaram R, Etya'ale D, Negrel AD, et al. 2002 global update of available data on visual impairment: a compilation of population-based prevalence studies. Ophthalmic epidemiology 2004;11(2):67-115.
Campochiaro PA, Soloway P, Ryan SJ, Miller JW. The pathogenesis of choroidal neovascularization in patients with age-related macular degeneration. Molecular vision 1999;5:34.

(Continued)

*Primary Examiner* — Christine J Saoud
*Assistant Examiner* — Jon M Lockard
(74) *Attorney, Agent, or Firm* — Joseph Hyosuk Kim; JHK Law

(57) ABSTRACT

The present application describes an isolated nucleic acid molecule encoding a polypeptide capable of synchronously binding VEGF polypeptide and placenta growth factor (PIGF) polypeptide comprising a nucleotide sequence encoding a VEGFR1 component.

9 Claims, 27 Drawing Sheets

(56) References Cited

OTHER PUBLICATIONS van Wijngaarden P, Coster DJ, Williams KA. Inhibitors of ocular neovascularization: promises and potential problems. Jama 2005;293(12):1509-13.
Jager RD, Mieler WF, Miller JW. Age-related macular degeneration. The New England journal of medicine 2008;358 (24):2606-17.
Group CR, Martin DF, Maguire MG, Ying GS, Grunwald JE, Fine SL, et al. Ranibizumab and bevacizumab for neovascular age-related macular degeneration. The New England journal of medicine 2011;364(20):1897-908.
Davis-Smyth T, Chen H, Park J, Presta LG, Ferrara N. The second immunoglobulin-like domain of the VEGF tyrosine kinase receptor Flt-1 determines ligand binding and may initiate a signal transduction cascade. The EMBO journal 1996;15(18):4919-27.
Fischer C, Jonckx B, Mazzone M, Zacchigna S, Loges S, Pattarini L, et al. Anti-PIGF inhibits growth of VEGF(R)- inhibitor-resistant tumors without affecting healthy vessels. Cell 2007;131(3):463-75.
Fischer C, Mazzone M, Jonckx B, Carmeliet P. FLT1 and its ligands VEGFB and PIGF: drug targets for anti-angiogenic therapy? Nature reviews Cancer 2008;8(12):942-56.
Adini A, Kornaga T, Firoozbakht F, Benjamin LE. Placental growth factor is a survival factor for tumor endothelial cells and macrophages. Cancer research 2002;62(10):2749-52.
Laurent J, Hull EF, Touvrey C, Kuonen F, Lan Q, Lorusso G, et al. Proangiogenic factor PIGF programs CD11b(+) myelomonocytes in breast cancer during differentiation of their hematopoietic progenitors. Cancer research 2011;71 (11):3781-91.
Anisimov A, Leppanen VM, Tvorogov D, Zarkada G, Jeltsch M, Holopainen T, et al. The basis for the distinct biological activities of vascular endothelial growth factor receptor-1 ligands. Science signaling 2013;6(282):ra52.
Elliott S, Lorenzini T, Asher S, Aoki K, Brankow D, Buck L, et al. Enhancement of therapeutic protein in vivo activities through glycoengineering. Nature biotechnology 2003;21(4):414-21.
Egrie JC, Browne JK. Development and characterization of novel erythropoiesis stimulating protein (NESP). Nephrology, dialysis, transplantation : official publication of the European Dialysis and Transplant Association—European Renal Association 2001;16 Suppl 3:3-13.
Ratner M. Genentech's glyco-engineered antibody to succeed Rituxan. Nature biotechnology 2014;32(1):6-7.
Jung K, Lee D, Lim HS, Lee SI, Kim YJ, Lee GM, et al. Double anti-angiogenic and anti-inflammatory protein Valpha targeting VEGF-A and TNF-alpha in retinopathy and psoriasis. The Journal of biological chemistry 2011;286 (16):14410-8.
Kim JY, Kim YG, Lee GM. CHO cells in biotechnology for production of recombinant proteins: current state and further potential. Applied microbiology and biotechnology 2012;93(3):917-30.
Koh YJ, Kim HZ, Hwang SI, Lee JE, Oh N, Jung K, et al. Double antiangiogenic protein, DAAP, targeting VEGF-A and angiopoietins in tumor angiogenesis, metastasis, and vascular leakage. Cancer cell 2010;18(2):171-84.
Kronewitter SR, de Leoz ML, Peacock KS, McBride KR, An HJ, Miyamoto S, et al. Human serum processing and analysis methods for rapid and reproducible N-glycan mass profiling. Journal of proteome research 2010;9(10):4952-9.
Kim C, Yang H, Fukushima Y, Saw PE, Lee J, Park JS, et al. Vascular RhoJ is an effective and selective target for tumor angiogenesis and vascular disruption. Cancer cell 2014;25(1):102-17.
Smith L, Wesolowski E, McLellan A, Kostyk SK, D'Amato R, Sullivan R, et al. Oxygen-induced retinopathy in the mouse Investigative ophthalmology & visual science 1994;35(1):101-11.
Yang Z, Lasker K, Schneidman-Duhovny D, Webb B, Huang CC, Pettersen EF, et al. UCSF Chimera, MODELLER, and IMP: an integrated modeling system. Journal of structural biology 2012;179(3):269-78.
Sola RJ, Griebenow K. Effects of glycosylation on the stability of protein pharmaceuticals. Journal of pharmaceutical sciences 2009;98(4):1223-45.
Hua S, Hu CY, Kim BJ, Totten SM, Oh MJ, Yun N, et al. Glyco-analytical multispecific proteolysis (Glyco-AMP): a simple method for detailed and quantitative Glycoproteomic characterization. Journal of proteome research 2013;12 (10):4414-23.
Jung K, Lee JE, Kim HZ, Kim HM, Park BS, Hwang SI, et al. Toll-like receptor 4 decoy, TOY, attenuates gram-negative bacterial sepsis. PloS one 2009;4(10):e7403.
Shojaei F, Wu X, Malik AK, Zhong C, Baldwin ME, Schanz S, et al. Tumor refractoriness to anti-VEGF treatment is mediated by CD11b+Gr1+ myeloid cells. Nature biotechnology 2007;25(8):911-20.
Murdoch C, Muthana M, Coffelt SB, Lewis CE. The role of myeloid cells in the promotion of tumour angiogenesis. Nature reviews Cancer 2008;8(8):618-31.
Shojaei F, Wu X, Zhong C, Yu L, Liang XH, Yao J, et al. Bv8 regulates myeloid-cell-dependent tumour angiogenesis. Nature 2007;450(7171):825-31.
Qian BZ, Li J, Zhang H, Kitamura T, Zhang J, Campion LR, et al. CCL2 recruits inflammatory monocytes to facilitate breast-tumour metastasis. Nature 2011;475(7355):222-5.
Kabbinavar F, Hurwitz HI, Fehrenbacher L, Meropol NJ, Novotny WF, Lieberman G, et al. Phase II, randomized trial comparing bevacizumab plus fluorouracil (FU)/leucovorin (LV) with FU/LV alone in patients with metastatic colorectal cancer. Journal of clinical oncology : official journal of the American Society of Clinical Oncology 2003;21(1):60-5.
Lin EY, Jones JG, Li P, Zhu L, Whitney KD, Muller WJ, et al. Progression to malignancy in the polyoma middle T oncoprotein mouse breast cancer model provides a reliable model for human diseases. The American journal of pathology 2003;163(5):2113-26.
Kuo CJ, Farnebo F, Yu EY, Christofferson R, Swearingen RA, Carter R, et al. Comparative evaluation of the antitumor activity of antiangiogenic proteins delivered by gene transfer. Proceedings of the National Academy of Sciences of the United States of America 2001;98(8):4605-10.
Bork K, Horstkorte R, Weidemann W. Increasing the sialylation of therapeutic glycoproteins: the potential of the sialic acid biosynthetic pathway. Journal of pharmaceutical sciences 2009;98(10):3499-508.
des Guetz G, Uzzan B, Chouahnia K, Morere JF. Cardiovascular toxicity of anti-angiogenic drugs. Targeted oncology 2011;6(4):197-202.
Michael IP, Westenskow PD, Hacibekiroglu S, Greenwald AC, Ballios BG, Kurihara T, et al. Local acting Sticky-trap inhibits vascular endothelial growth factor dependent pathological angiogenesis in the eye. EMBO molecular medicine 2014;6(5):604-23.
Stewart MW. Aflibercept (VEGF Trap-eye): the newest anti-VEGF drug. The British journal of ophthalmology 2012;96 (9):1157-8.
Heier JS, Brown DM, Chong V, Korobelnik JF, Kaiser PK, Nguyen QD, et al. Intravitreal aflibercept (VEGF trap-eye) in wet age-related macular degeneration. Ophthalmology 2012;119(12):2537-48.

* cited by examiner

FIG. 1A
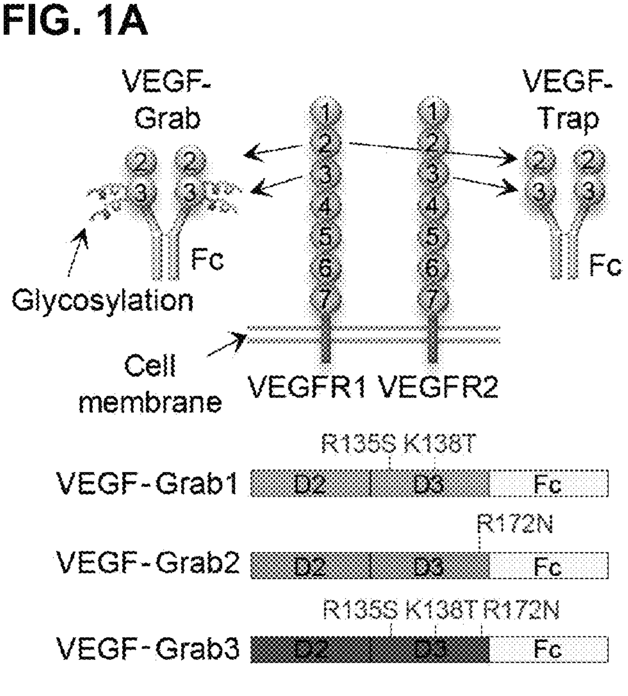
FIG. 1B
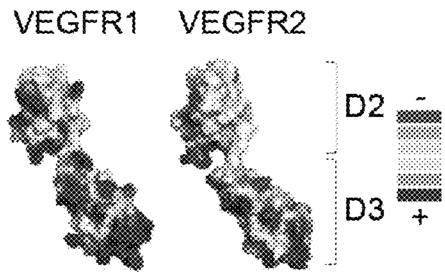
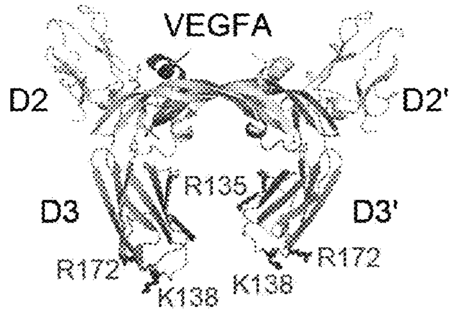
FIG. 1C

FIG. 1D
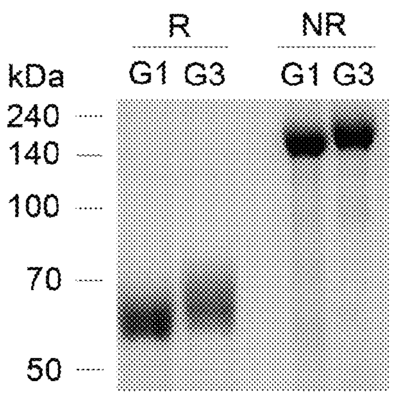
FIG. 1E
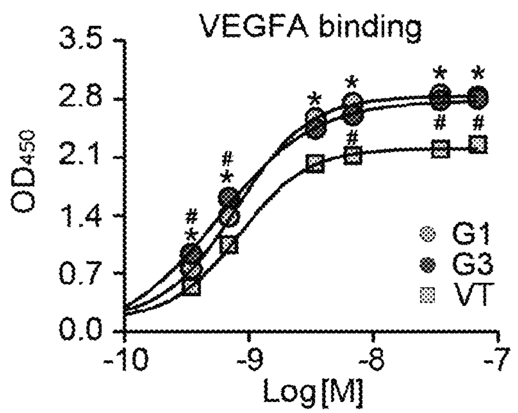
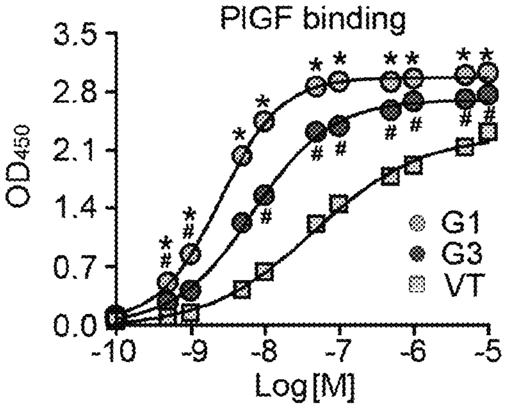
FIG. 1F
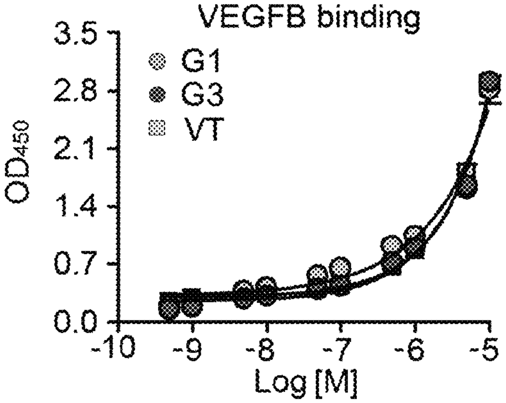
FIG. 1G

FIG. 3F
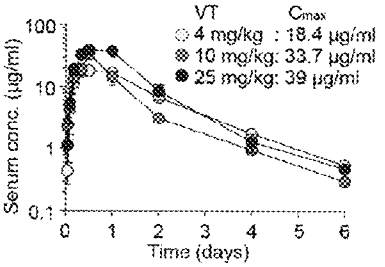
FIG. 3G
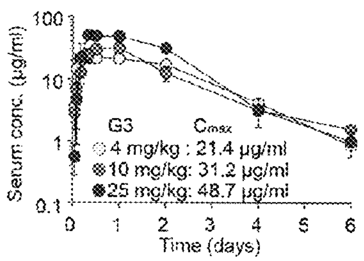
FIG. 3H
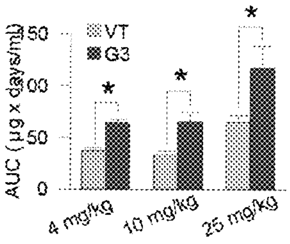
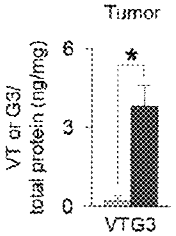
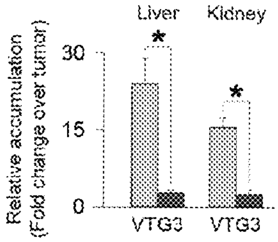
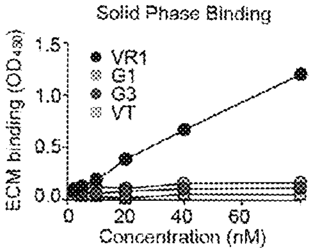
FIG. 3I
FIG. 3J
FIG. 3K Tumor volume (mm³)
Ctrl
G3 25 mg/kg
VT 25 mg/kg
Time (days)

Ctrl
VT
G3
Tumor sections
Tumor weight (g)
C VTG3
Necrotic area (%)
C VTG3

Intratumoral Peritumoral
CD31
LYVE-1 Pan-CK

VD (%)
LVD (%)

Metastasis (%)

FIG. 5J
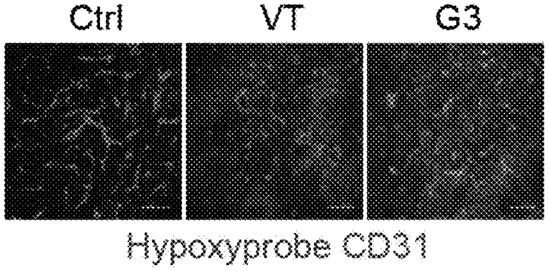
FIG. 5K
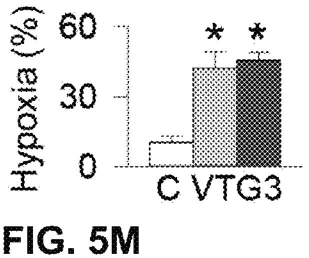
FIG. 5L
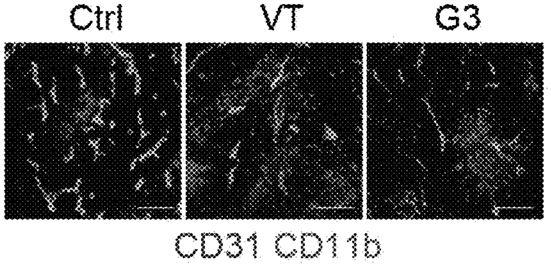
FIG. 5M
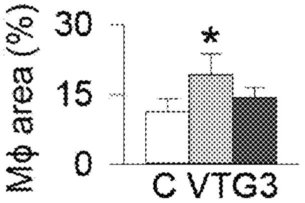
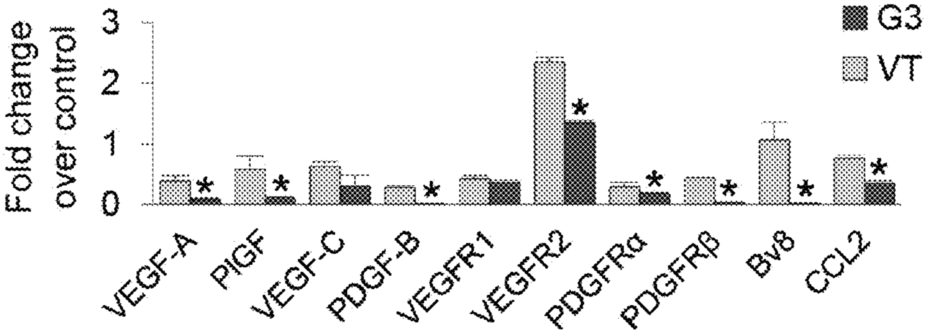
FIG. 5N FIG. 5O
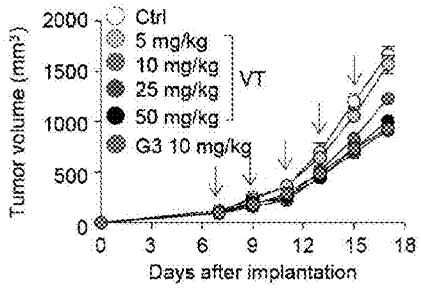
FIG. 5P
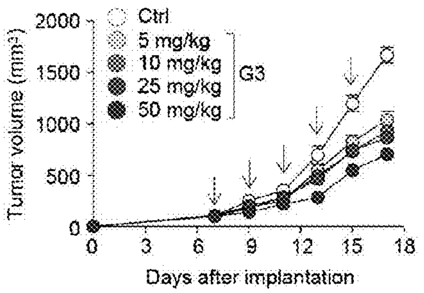
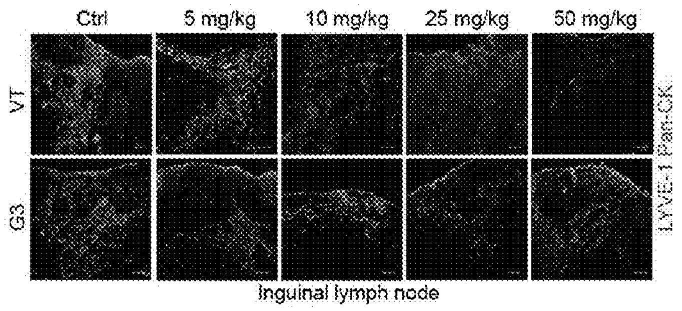
FIG. 5Q
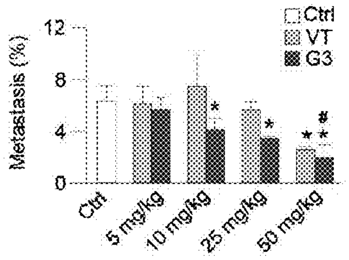
FIG. 5R FIG. 6E
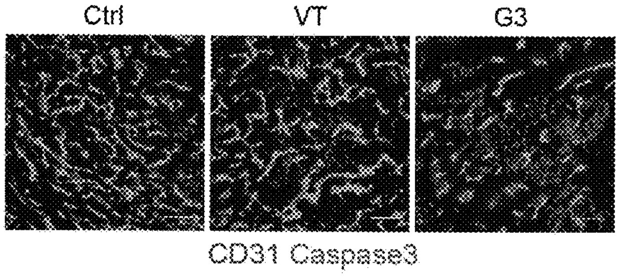
FIG. 6F
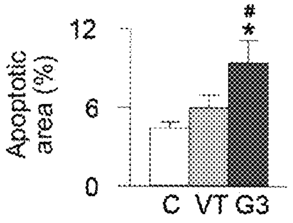
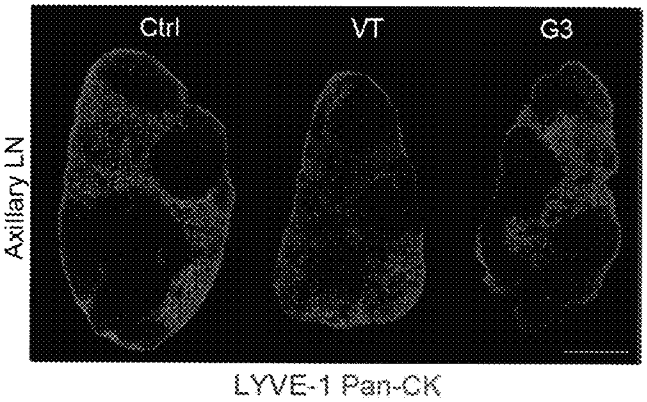
FIG. 6G
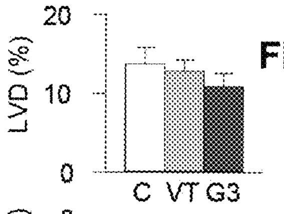
FIG. 6H
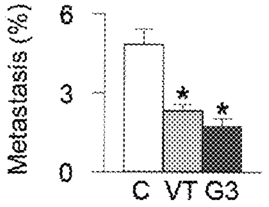
FIG. 6I FIG. 7A
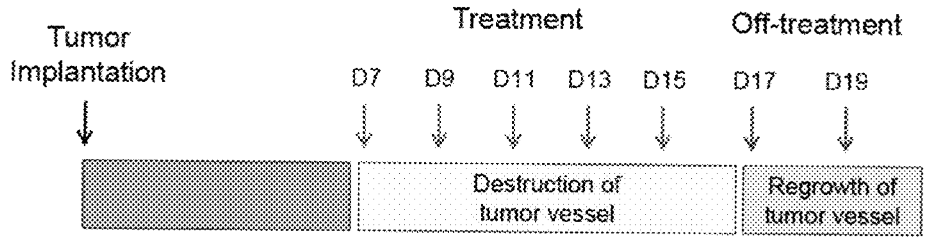
FIG. 7B
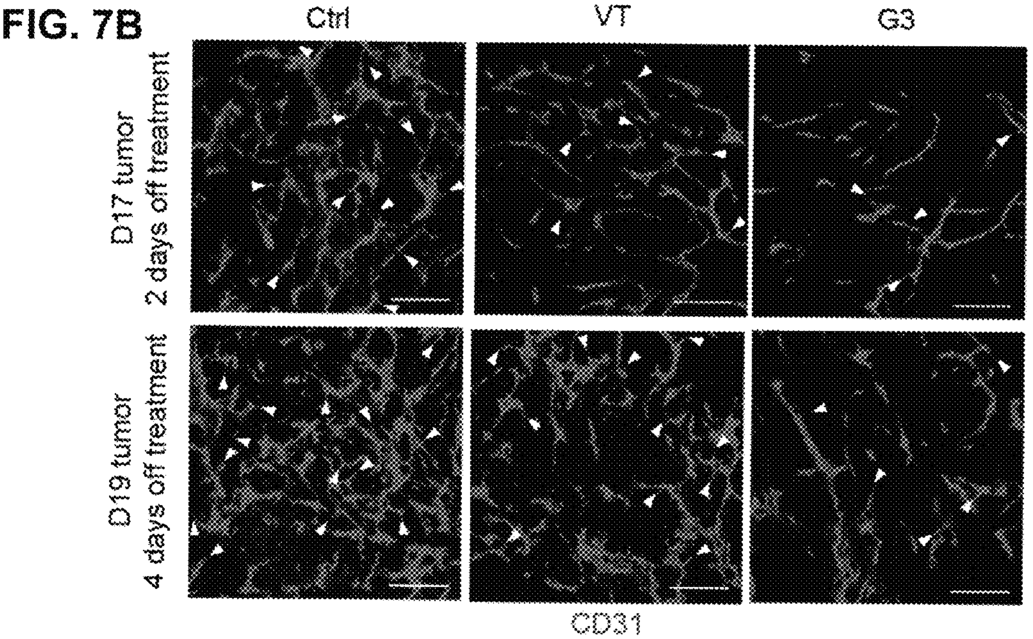
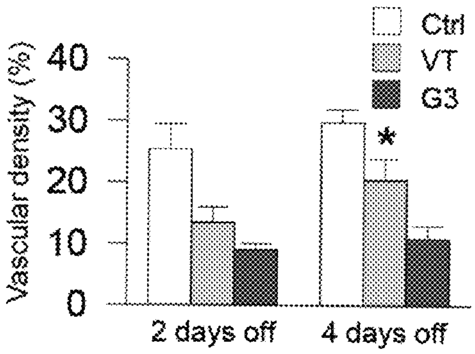
FIG. 7C
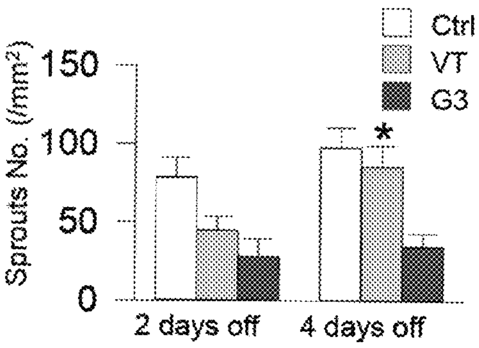
FIG. 7D FIG. 8A
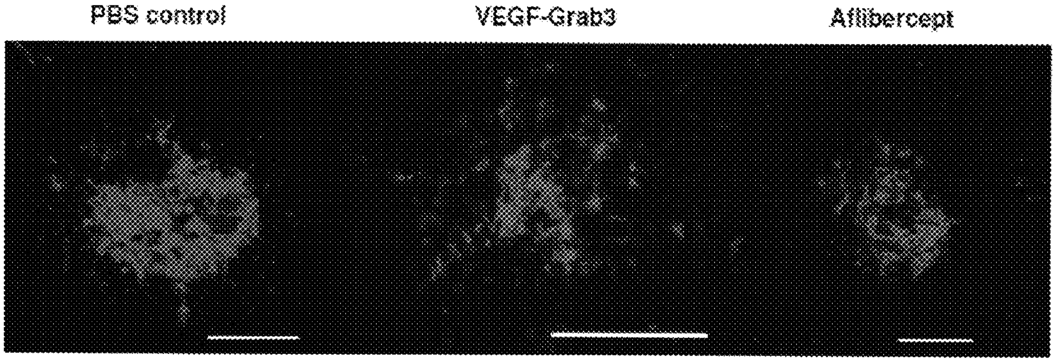
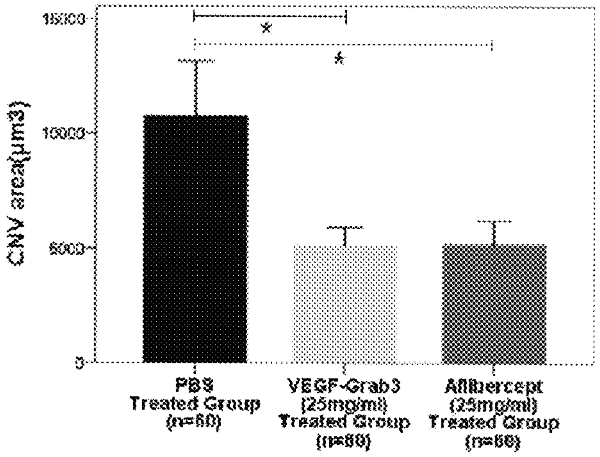
FIG. 8B

| Site | Glycosylated | Sequence | Mass | VEGF-Trap | VEGF-Grab1 | VEGF-Grab3 |
|---|---|---|---|---|---|---|
| 61Asn | Yes | $^{57}$VTSPDITVTLK$^{67}$ | 1172.654 | ✓ | ✓ | ✓ |
| | No | $^{57}$VTSPNITVTLK$^{67}$ | 1171.670 | × | × | × |
| 93Asn | Yes | $^{87}$KGFIISDATYK$^{97}$ | 1241.655 | ✓ | ✓ | ✓ |
| | No | $^{87}$KGFIISNATYK$^{97}$ | 1240.671 | × | × | × |
| 172Asn | Yes | $^{173}$DASVR$^{176}$ | 546.265 | N/A | N/A | × |
| | No | $^{173}$NASVR$^{176}$ | 545.281 | N/A | N/A | ✓ |
| | Yes | $^{173}$DASVRR$^{177}$ | 702.366 | N/A | N/A | × |
| | No | $^{173}$NASVRR$^{177}$ | 701.382 | N/A | N/A | ✓ |
| 308Asn | Yes | $^{304}$EEQYDSTYR$^{312}$ | 1189.478 | ✓ | ✓ | ✓ |
| | No | $^{304}$EEQYNSTYR$^{312}$ | 1188.494 | × | × | × |

FIG. 11A

✓ Detected
× Not detected
N/A Not Available

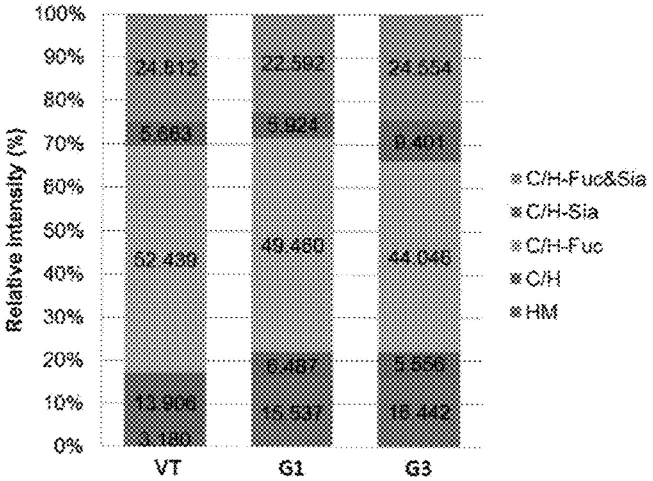

FIG. 11B

-VA
+VA
C G1 G3 VT C G1 G3 VT
pVR2
VR2
pERK
ERK pVR2/VR2
-VA
+VA pERK/ERK
-VA
+VA

+ VA
- VA
Ctrl
Ctrl
G1
G3
VT

Migration (%)
+VA
-VA
C C G1 G3 VT
+ VA
- VA
Ctrl
Ctrl
G1
G3
VT

Tube area (%)
+VA
-VA
C C G1 G3 VT

FIG. 17A
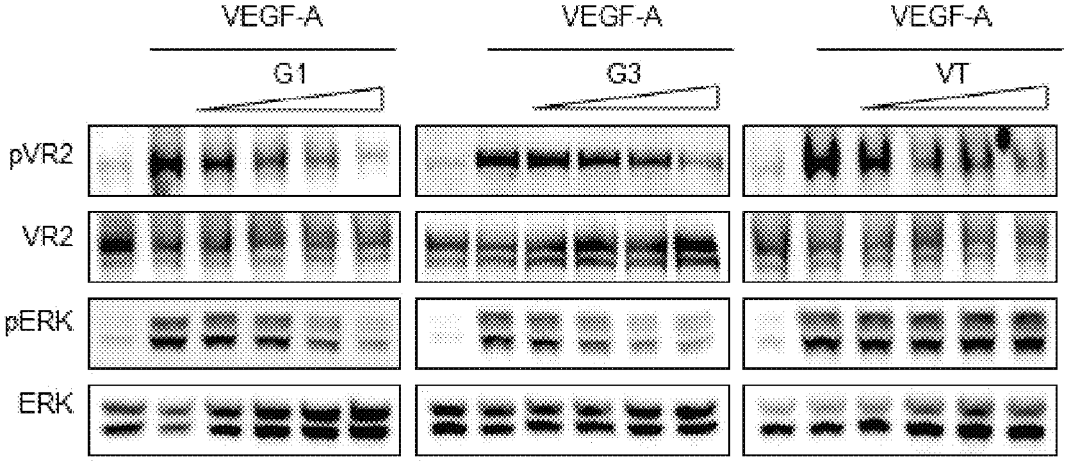
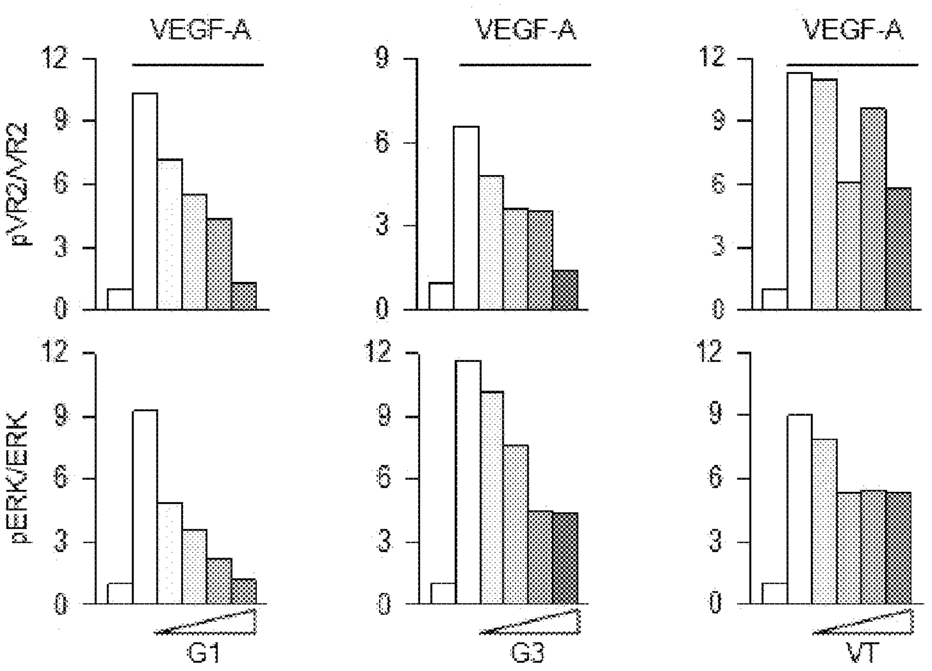
FIG. 17B

GLYCOSYLATED VEGF DECOY RECEPTOR FUSION PROTEIN

BACKGROUND OF THE INVENTION

1. Field of the Invention

The present application relates to making a chimeric molecule that is used to prevent blood vessel formation as a form of treating cancer or treating eye disease.

2. Description of the Background

Vascular endothelial growth factor-A (VEGF-A) is a critical regulator of tumor angiogenesis, mainly through the activation of its primary receptor, VEGF receptor 2 (VEGFR2). VEGF-A is expressed in most tumor cells and corresponding stromal cells throughout every stage of tumor progression, while VEGFR2 is highly expressed in growing tumor vessels, leading to the formation of structurally and functionally malformed tumor blood vessels. VEGF-A specifically binds to the second immunoglobulin (Ig) homology domain (D2) of the extracellular region of VEGFR2, resulting in activation of pro-angiogenic signalling. For the past decade, much effort has been devoted to targeting this VEGF-A/VEGFR2 signalling pathway using monoclonal antibodies, soluble decoy receptor fusion proteins, and small molecular inhibitors in cancer patients. While the current therapeutic blockade of VEGF-A/VEGFR2 signalling provides clinical benefits, the anti-cancer effect is modest and transient, eventually giving rise to acquired resistance through the activation of alternative pro-angiogenic pathways and further recruitment of pro-angiogenic cells such as tumor-associated macrophages (TAM). These limitations highlight current unmet needs in anti-angiogenic cancer treatment strategies, which must be addressed for successful therapy development.

Many ocular diseases are also associated with abnormal angiogenesis and up-regulated VEGF. Particularly, exudative age-related macular degeneration (AMD) is one of the most important causes of blindness in developed countries and the most clinically critical subtype of AMD. In exudative AMD, the macular region rapidly deteriorates due to abnormal angiogenesis, termed "choroidal neovascularization (CNV)" which arises from the choriocapillary across the retinal pigment epithelium (RPE) and Bruch's membrane to subretinal space of macula. CNV is also a major complication that threatens the vision of patients with various retinal degenerative and inflammatory diseases, including pathologic myopia and ocular histoplasmosis. Angiogenesis is normally a compensatory mechanism of our body in pathologic situations such as coronary collateral formation and wound healing process. And this mechanism is also triggered by an oxygen insufficiency state as known as "hypoxia". Hypoxic state stimulates hypoxic inducible factors (HIFs) including VEGF and it plays a crucial role in angiogenesis. In addition, eyes with high concentration of VEGF suffer from leakage from retinal vessels, and subsequently, macular edema develops. Therefore, VEGF may be a therapeutic target for ocular diseases associated with abnormal angiogenesis and vascular leakage such as exudative AMD, diabetic retinopathy, retinopathy of prematurity, neovascular glaucoma, corneal neovascularization, retinal vein occlusion and macular edema due to diabetic retinopathy or retinal vein occlusion.

VEGF-A binds to both VEGFR1 and VEGFR2. The binding affinity of VEGFR1 to VEGF-A (<10~20 pM) is much higher than that of VEGFR2 (<100~125 pM). In addition, VEGFR1 is a receptor for other pro-angiogenic ligands, VEGF-B and placental growth factor (PlGF), which have recently been highlighted as alternative targets for anti-angiogenic therapy. Because of its ability to bind multiple pro-angiogenic ligands, VEGFR1 has been considered as a potential backbone for the development of a novel decoy receptor fusion protein for therapeutic purposes. However, the efficiency of a decoy receptor fusion protein which consisted of the first 3 Ig domains of VEGFR1 fused with the Fc region of IgG1 (VEGFR1-Fc) proved unsatisfactory, due to non-specific binding to the extracellular matrix (ECM) attributed to the abundant positively charged residues in the third Ig domain (VEGFR1 D3) and its high isoelectric point (pI) value. Nonetheless, this finding inspired the invention of VEGF-Trap (Aflibercept from Regeneron), consisting of VEGFR1 D2 and VEGFR2 D3 fused to IgG1 Fc. By switching VEGFR1 D3 to VEGFR2 D3, the net pI of VEGF-Trap was decreased, resulting in less ECM binding and an improved pharmacokinetic (PK) profile compared to VEGFR1-Fc. However, because VEGFR2 D3 was used instead of VEGFR1 D3, the high-affinity binding of VEGF-A and PlGF was disturbed. Hence, the important issue to be addressed now is how to incorporate VEGFR1 D3 into a decoy receptor while minimizing non-specific ECM binding.

Glycosylation is a post-translational modification that results in the addition of carbohydrate chains to specific asparagine (N-linked glycosylation) or serine/threonine (O-linked glycosylation) residues. Glycosylation of secreted and membrane proteins affects their biochemical and biological properties. It usually provides a negative charge and increases solubility, thus diminishing non-specific binding to the ECM. Moreover, glycosylation grants resistance to proteolysis and extended serum half-life, enhancing a protein's PK profile. Glyco-engineered therapeutic proteins such as Aranesp (erythropoietin) from Amgen and Gazyva (obinutuzumab) from Genentech are good examples that exploited these advantages.

Here, we developed a novel VEGF decoy receptor fusion protein, VEGF-Grab. Parental VEGFR1-Fc (VEGFR1 D2-D3 fused to Fc) was used as a backbone, and new potential glycosylation sites were introduced into the positively-charged patch of VEGFR1 D3 by site-directed mutagenesis. This engineered VEGF-Grab showed significantly improved decoy efficiency and a dramatic decrease in net pI, thus attenuating non-specific ECM binding and enhancing PK profiles. Thus, VEGF-Grab strongly suppressed tumor angiogenesis, progression, and metastasis via effective capturing of three VEGFR1 ligands, VEGF-A, VEGF-B, and PlGF. Furthermore, we show the intravitreal therapeutic efficacy of VEGF-Grab3 to regress new vessels in laser-induced CNV and oxygen-induced retinopathy (OIR) murine models, which are reliable methods in predicting the therapeutic value of anti-VEGF therapies now approved for treating AMD and diabetic retinopathy.

SUMMARY OF THE INVENTION

Anti-angiogenic therapies targeting vascular endothelial growth factor A (VEGF-A) have been commonly used in clinics to treat cancers and age-related macular degeneration (AMD). However, its clinical efficacy has been limited, with drawbacks including acquisition of resistance and activation of compensatory pathways resulting from elevated circulating VEGF-B and placenta growth factor (PlGF). To bypass these disadvantages, we developed a novel glycosylated soluble decoy receptor fusion protein, VEGF-Grab, which can neutralize VEGF-A, VEGF-B, and PlGF. VEGF-Grab has the second and third immunoglobulin (Ig)-like domains of VEGF receptor 1 (VEGFR1) fused to IgG1 Fc, with three potential glycosylation sites introduced into the third Ig-like domain of VEGF-Grab by mutagenesis. Compared to VEGF-Trap, VEGF-Grab showed more potent decoy activity against VEGF and PlGF, mainly attributed to the VEGFR1 backbone. Most importantly, the negatively charged O-glycans attached to the third Ig-like domain of VEGFR1 counterbalanced the originally positively charged VEGFR1 backbone, minimizing non-specific binding of VEGF-Grab to the extracellular matrix, and resulting in greatly improved pharmacokinetic profile. These advancements led to stronger and more durable anti-angiogenic and anti-tumor efficacy as compared to VEGF-Trap, while toxicity profiles were comparable to VEGF-Trap. Collectively, our results highlight VEGF-Grab as a promising therapeutic candidate for further clinical drug development.

In one aspect, the present invention is drawn to an isolated nucleic acid molecule encoding a polypeptide capable of synchronously binding VEGF polypeptide and placenta growth factor (PIGF) polypeptide comprising a nucleotide sequence encoding a VEGFR1 component. The VEGFR1 component may include the second and third immunoglobulin (Ig)-like domains. The at least one encoded positive amino acid residue in at least one domain of VEGFR1 may be mutated to a negatively charged residue. The domain may be the third domain. And the amino acid residue may be on the β1-β2 loop, which may include nucleic acid positions 397 to 432 of SEQ ID NO:1, which corresponds to amino acid residues 133 to 144 of SEQ ID NO:2, or β3-β4 loop, which comprises nucleic acid positions 490 to 522 of SEQ ID NO:1, which corresponds to amino acid residues 164 to 174 of SEQ ID NO:2. Also, the at least one encoded positive amino acid residue in at least one domain of VEGFR1 may be mutated so as to produce a glycosylation site. The at least one encoded positive amino acid residue in at least one domain of VEGFR1 may be mutated so as to produce a decrease in net pI of the encoded polypeptide. The residue to be mutated may be R135 residue on the β1-β2 loop, K138 residue on the β1-β2 loop, or R172 residue on the β3-β4 loop on the third domain. The VEGF may be VEGF-A or VEGF-B. Optionally, the VEGFR1 component may be operatively linked to a nucleotide sequence encoding a multimerizing component.

In another aspect, the invention is directed to an isolated nucleic acid molecule comprising a nucleotide sequence encoding: (a) VEGF-Grab1; (b) VEGF-Grab2; or (c) VEGF-Grab3. In yet another aspect, the invention is drawn to a nucleic acid vector, which includes any of the nucleic acid molecule described above. The vector may be viral vector. Or, the vector may be an expression vector that includes any of above-described nucleic acid molecule, wherein the nucleic acid molecule may be operatively linked to an expression control sequence.

In yet another aspect, the invention is directed to a method of generating a polypeptide capable of synchronously binding VEGF polypeptide and placenta growth factor (PIGF) polypeptide comprising a VEGFR1 component in a patient, comprising administering to the patient the nucleic acid vector described above.

In yet another aspect, the invention is drawn to a host-vector system for the production of a polypeptide, which includes the expression vector described above, in a suitable host cell. The suitable host cell may be a bacterial cell, yeast cell, insect cell, or mammalian cell.

In another aspect, the invention is drawn to a method of generating a polypeptide capable of synchronously binding VEGF polypeptide and placenta growth factor (PIGF) polypeptide comprising a VEGFR1 component in a patient, comprising administering to the patient the cell described above.

In another aspect, the invention is drawn to a method of producing a polypeptide which steps include growing cells of the host-vector system described, under conditions permitting production of the polypeptide and recovering the polypeptide so produced.

In yet another aspect, the invention is drawn to a polypeptide encoded by any of the isolated nucleic acid molecule described above. The polypeptide may be wherein the VEGFR1 component comprises the second and third immunoglobulin (Ig)-like domains. The polypeptide may be wherein at least one positive amino acid residue in at least one domain of VEGFR1 may be mutated to a negatively charged residue. The domain may be the third domain. The amino acid residue may be on the β1-β2 loop, which may include amino acid residues 133 to 144 of SEQ ID NO:2, or β3-β4 loop, which may include amino acid residues 164 to 174 of SEQ ID NO:2. The at least one positive amino acid residue in at least one domain of VEGFR1 may be mutated so as to include a glycosylation site. The polypeptide may be glycosylated. Further, the polypeptide may be sialylated. In the polypeptide discussed above, at least one positive amino acid residue in at least one domain of VEGFR1 may be mutated so as to produce a decrease in net pI of the polypeptide. The residue to be mutated may be R135 residue on the β1-β2 loop, K138 residue on the β1-β2 loop, or R172 residue on the β3-β4 loop on the third domain.

In another aspect, the invention is drawn to a method of blocking blood vessel growth in a mammal comprising administering to the mammal in need thereof an effective amount of the polypeptide described above. The mammal may be human.

The blood vessel growth may occur in the eye to cause a medical condition that affects sight. The medical condition may be age-related macular degeneration, exudative age-related macular degeneration, choroidal neovascularization, pathologic myopia, diabetic retinopathy, diabetic macular edema, retinal vein occlusion, retinopathy of prematurity or neovascular glaucoma. The choroidal neovascularization may be myopic choroidal neovascularization, traumatic choroidal neovascularization, uveitic choroidal neovascularization, ocular histoplasmosis, or idiopathic choroidal neovascularization.

In yet another aspect, the invention is drawn to a method of inhibiting VEGF and/or PIGF activities in a mammal comprising administering to the mammal an effective amount of any of the polypeptides described above. The mammal may be human.

In another aspect, the invention is drawn to a method of attenuating or preventing tumor growth in a mammal, comprising administering to a subject in need thereof a therapeutically effective amount of the polypeptides described above. The mammal may be human.

In yet another aspect, the invention is drawn to a method of suppressing metastasis in a mammal, comprising administering to a subject in need thereof a therapeutically effective amount of the polypeptides described above. The mammal may be human.

In another aspect, the invention is drawn to a method of attenuating or preventing tumor growth in a mammal, comprising administering to a subject in need thereof a therapeutically effective amount of any of the polypeptides described above and a cytotoxic therapeutic agent. The mammal may be human. And, the cytotoxic therapeutic agent may be without limitation cisplatin.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 1A-1G show generation and characterization of VEGF-Grab. FIG. 1A, Schematic diagram of VEGF-Grabs (VEGF-Grab1, VEGF-Grab2 and VEGF-Grab3; hereinafter referred to as G1, G2, and G3) and VEGF-Trap (VT). Mutated residues in VEGF-Grabs are indicated by brown at the lower panel. FIG. 1B, Electrostatic potential of D2-D3 domain in VEGFR1 (left) and VEGFR2 (right). Positively and negatively charged residues are colored in blue and red, respectively. FIG. 1C, Model structure of VEGF-A/VEGFR1 D2-D3 complex. VEGF-A dimer is colored in yellow and green. VEGFR1 D2 and D3 are colored in tan and mustard. Residues indicated by blue stick are target sites for mutagenesis. FIG. 1D, SDS-PAGE analysis of G1 and G3 in reduced (R) and non-reduced (NR) conditions. E-G, Binding affinities of G1, G3, and VT for VEGF-A (FIG. 1E), PlGF (FIG. 1F), or VEGF-B (FIG. 1G) $*p<0.05$ G1 vs VT; $\#p<0.05$ G3 vs VT. For each group, n=3. Values are mean±SD.

FIGS. 3A-3K show that VEGF-Grab3 exhibits low ECM binding and prolonged pharmacokinetic profile. FIG. 3A, Isoelectric point analysis of G1, G3, and VT. Red lines on each band were used to analyse net pI. FIG. 3B. Comparison of pI for each protein. Net pI of each protein was the mean pI of each isoform denoted as lines. FIG. 3C, PNGase F digestion to remove N-linked glycan. FIG. 3D, Analysis of O-linked glycosylation at Serine135 of G3. FIG. 3E, Schematic diagram for glycosylated sites analysed by mass spectrometry. Occupied N-glycosylation sites (red); occupied O-glycosylation sites (blue); unoccupied N- or O-glycosylation sites (grey). F and G, PK profiles analysis of VT (FIG. 3F) and G3 (FIG. 3G) at varying doses. FIG. 3H, Comparison of area under the curve (AUC) of VT and G3. I and J, Tissue distribution of G3 and VT 48 hr after subcutaneous injection (4 mg/kg). FIG. 3I, Accumulated VT and G3 in tumor. FIG. 3J, Relative accumulated levels of VT and G3 in liver and kidney compared to tumor. FIG. 3K. Analysis of in vitro ECM binding affinities with Matrigel-coated plates. $*p<0.05$ G1 vs VT; $\#p<0.05$ G3 vs VT. Each group, n=3. Values are mean±SD.

FIGS. 4A-4H show that VEGF-grabs inhibit EC survival, migration, and tube formation via suppression of VEGF signalling pathway. FIGS. 4A-4C, Inhibition of VEGF-A-induced phosphorylation of VEGFR2 and ERK in HUVECs by the treatment of G1, G3, and VT. Immunoblotting (FIG. 4A) and quantification (FIG. 4B and FIG. 4C). FIG. 4D, Cell survival assay with HUVECs after G1, G3, and VT treatment (0.35, 0.7, 3.5, 7, 35, 70 nM) in the presence of VEGF-A (0.2 nM). FIG. 4E and FIG. 4F, Cell migration assay with HUVECs in the presence of VEGF-A and indicated proteins. Images (FIG. 4E) and quantification (FIG. 4F) of migration area. Wound healing areas are indicated in red. FIG. 4G and FIG. 4H, Images (FIG. 4G) and quantification (FIG. 4H) for tube formation assay with HUVECs in the presence of VEGF-A and indicated proteins. $*p<0.05$ vs control; $\#p<0.05$ G3 vs VT. Each group, n=3. Values are mean±SD.

FIGS. 5A-5U show that VEGF-Grab3 effectively suppresses tumor growth, angiogenesis, and metastasis in LLC tumors. FIGS. 5A-5N, Mice were treated with proteins on the indicated days (arrows). FIG. 5A and FIG. 5C, Comparison of tumor growth (FIG. 5A) and tumor weights (FIG. 5C). FIG. 5B and FIG. 5D, Images (FIG. 5B) and quantification (FIG. 5D) of intratumoral necrotic area stained with H&E. Dotted line demarcates intratumoral necrosis. FIG. 5E and FIG. 5F, Images (FIG. 5E) and quantification (FIG. 5F) of $CD31^+$ blood vessels in the peri- and intratumoral area. FIG. 5G, Images showing cytokeratin$^+$ tumor cell metastasis (red) in inguinal LNs. Each indicated region (squares) is magnified in the lower panel. FIG. 5H and FIG. 5I, Quantifications of lymphatic vascular densities (LVD) (FIG. 5H) and cytokeratin$^+$ tumor cell metastasis (FIG. 5I). FIG. 5J and FIG. 5K, Images (FIG. 5J) and quantifications (FIG. 5K) of Hypoxyprobe$^+$ hypoxic areas (green) in tumors. FIG. 5L and FIG. 5M, Images (FIG. 5L) and quantifications (FIG. 5M) of $CD11b^+$ myeloid cells (red) in tumor. FIG. 5N, Comparisons of mRNA expression levels of various genes in intratumoral tissue after treatment with G3 and VT. Values indicate fold changes over control tumors. FIGS. 5O-5R, Comparative dose responses of VT and G3 on tumor growth and metastasis. LLC tumor-bearing mice were treated with either VT, or G3 at the indicated days (arrows), respectively. FIG. 5O and FIG. 5P, Comparison of tumor growth after VT (FIG. 5O) or G3 (FIG. 5P) treatment. FIG. 5Q and FIG. 5R, Images (FIG. 5Q) and quantification (FIG. 5R) of cytokeratin$^+$ tumor cell metastasis in inguinal LNs. Scale bars, 100 μm. $*p<0.05$ vs control; $\#p<0.05$ G3 vs VT. FIGS. 5S-5U, Combination therapy of cisplatin (green arrows, at day 9 after tumor implantation) with either VT, or G3 at the indicated days (black arrows). FIG. 5S, Comparison of LLC tumor growth. Images (FIG. 5T) and comparison (FIG. 5U) of Caspase3$^+$ apoptotic cells (red) in intratumoral area. For each group n=5. Values are mean±SD. Scale bars, 100 μm. $*p<0.05$ vs cisplatin; $\#p<0.05$ cis+G3 vs cis+VT.

FIGS. 6A-6I show that VEGF-Grab3 delays tumor growth and suppresses neovessel formation and metastasis in a spontaneous breast cancer model. FIGS. 6A-6I, Female MMTV-PyMT mice (12-weeks old) received intraperitoneal-injections of VT, or G3 (25 mg/kg) twice per week for 3 weeks. FIG. 6A, Tumor sections stained with H&E. Invasive tumor cells (Inv), early carcinoma lesions (Ea), and surrounding adipose tissue (Adi) are denoted by dotted lines. FIG. 6B, Comparison of volumes of tumor nodules. Lines denote mean values. FIG. 6C and FIG. 6D, Images (FIG. 6C) and comparison (FIG. 6D) of $CD31^+$ blood vessels in the peri- and intratumoral areas. FIG. 6E and FIG. 6F, Images (FIG. 6E) and comparison (FIG. 6F) of Caspase3$^+$ apoptotic cells (red) in tumor. FIG. 6G, Images showing cytokeratin$^+$ tumor cell metastasis (red) in axillary LNs. FIG. 6H and FIG. 6I, Quantifications of LVD (FIG. 6H) and cytokeratin$^+$ tumor cell metastasis (FIG. 6I) in axillary LNs. Unless otherwise noted, for each group, n=4. Values are mean±SD. Scale bars, 100 μm. $*p<0.05$ vs control. $\#p<0.05$ G3 vs VT.

FIGS. 7A-D show that VEGF-Grab3 exerts more durable suppression of tumor angiogenesis. FIGS. 7A-7D, tumor vessel regrowth after VT or G3 treatment. FIG. 7A. Experimental Scheme. Mice were treated with proteins on the indicated days (green arrows). Treatment was withdrawn, and analysed at D17 and D19 (blue arrows). FIGS. 7B-7D, Changes in the vascularity after treatment with either VT, or G3. White arrowheads indicate representative new vascular sprouts. Images (FIG. 7B) and quantifications of $CD31^+$ blood vessels (FIG. 7C) and sprouts numbers (FIG. 7D). *p<0.05 VT D17 vs VT D19.

FIGS. 8A-8B show that a single intravitreal injection of 50 μg VEGF-Grab3 suppresses choroidal neovascularization at sites of rupture of Bruch's membrane. FIG. 8A. Representative confocal microscope images of the anti-PECAM-1/CD31 antibody-stained CNV lesions in the choroid flat mounts from laser-induced CNV in mice treated with PBS (Left), VEGF-Grab3 (middle) and Aflibercept (Right). CNVs were significantly abolished by the VEGF-Grab3 or Aflibercept treatment compared to PBS-treatment. Scale bar=100 μm. FIG. 8B. Bar graph showing the size of CNVs area developed in the laser-induced control PBS injected eyes, Aflibercept-treated eyes and VEGF-Grab3-treated eyes. Data are expressed as means±standard error of the mean (SEM). Measurement of the area of CNV by image analysis confirmed that there was significantly less neovascularization in eyes treated with VEGF-Grab3 (60 rupture sites) or Aflibercept (60 rupture sites) compared to those treated with PBS (60 rupture sites). Statistical differences between means were determined by analysis of variance with one-way followed by the Bonferroni test (* P<0.01).

FIG. 9A. Representative magnified confocal microscope images of OIR model mice. The density of vasculature was significantly reduced by the VEGF-Grab3 treatment compared to PBS-treatment. FIG. 9B. Bar graph showing VEGF-Grab3 increases the area of avascular retina at P17 in OIR model mice. Data are expressed as means±standard error of the mean (SEM). The vascular intensity of VEGF-Grab3 treated mice significantly decreased compared with the PBS-injected control eyes. (P<0.01).

FIGS. 11A-11B show analysis of N-linked glycosylation for VEGF-Grabs and VEGF-Trap. FIG. 11A, List of peptides possibly identified from PNGaseF/trypsin digestion of VEGF-Grabs and VT that encompass a potential site of N-glycosylation. If an Asn residue is N-glycosylated at a particular position, that residue will be converted to Asp after PNGase digestion, resulting in a mass gain of 0.984 Da. In contrast, Asn residues unoccupied by N-glycans are unaffected by deglycosylation. Thus, by tracking the mass of deglycosylated tryptic peptide with LC/MS, the occupied or unoccupied states of N-glycosylation sites can be determined. Detected peptides are indicated as ✓. Undetected peptides are indicated as x. N/A indicates not available. FIG. 11B, Relative abundances of each N-glycan class in VT, G1, and G3: fucosylated/sialylated complex/hybrid (C/H-Fuc&Sia); sialylated complex/hybrid (C/H-Sia); fucosylated complex/hybrid (C/H-Fuc); undecorated complex/hybrid (C/H); high mannose (HM).

FIGS. 15A and 15B, VT and G3 levels in tissues after subcutaneous injections of VT (4 mg/kg) and G3 (4 mg/kg) into LLC tumor-bearing C57BL/6J mice. Tissues were harvested after 48 hr, lysed in lysis buffer (Lysis buffer 6, R&D), quantified by Bradford assay, and analysed by ELISA for liver (FIG. 15A) and kidney (FIG. 15B). *p<0.05 G3 vs VT. Values are mean±SD.

FIGS. 16A-16C, VEGFR2 and ERK phosphorylation in HUVECs after treatment with G1, G3, and VT (2 μg/ml, 14 nM, respectively) in the presence or absence of VEGFA (50 ng/ml, 1 nM). Immunoblotting (FIG. 16A) and quantification (FIG. 16B and FIG. 16C). und. indicates undetected. FIG. 16D and FIG. 16E, Cell migration assay with HUVECs in the presence or absence of VEGFA (50 ng/ml, 1 nM) and indicated proteins (2 μg/ml, 14 nM). The amount of wound healing was monitored after 12 hr. Wound healing areas are indicated in red. Images (FIG. 16D) and quantification (FIG. 16E) of migration area. FIG. 16F and FIG. 16G, Tube formation assay with HUVECs in the presence or absence of VEGFA (50 ng/ml, 1 nM) and indicated proteins (2 μg/ml, 14 nM). Images (FIG. 16F) and quantification (FIG. 16G) of tube formation. Scale bars, 100 μm.

FIGS. 17A-17B show dose-dependent inhibition of VEGFR2 signalling with anti-VEGF therapy. FIGS. 17A-17B, HUVECs were cultured, starved overnight, pre-treated with each protein (0.125 μg/ml (0.875 nM), 0.25 μg/ml (1.75 nM), 0.5 μg/ml (3.5 nM), and 1 μg/ml (7 nM)) for 15 min, and treated with VEGFA (50 ng/ml, 1 nM) for 10 min. Cells were lysed and indicated proteins were immunoblotted to detect the activation of VEGFR2 and ERK1/2 signalling. FIG. 17A, Immunoblotting showing dose-dependent inhibition of VEGFR2 and ERK1/2 phosphorylation after treatment with VEGF-Grabs or VT. FIG. 17B, Comparisons of VEGFR2 and ERK1/2 phosphorylation after treatment with VEGF-Grabs or VT.

DETAILED DESCRIPTION OF THE INVENTION

Figure 2:
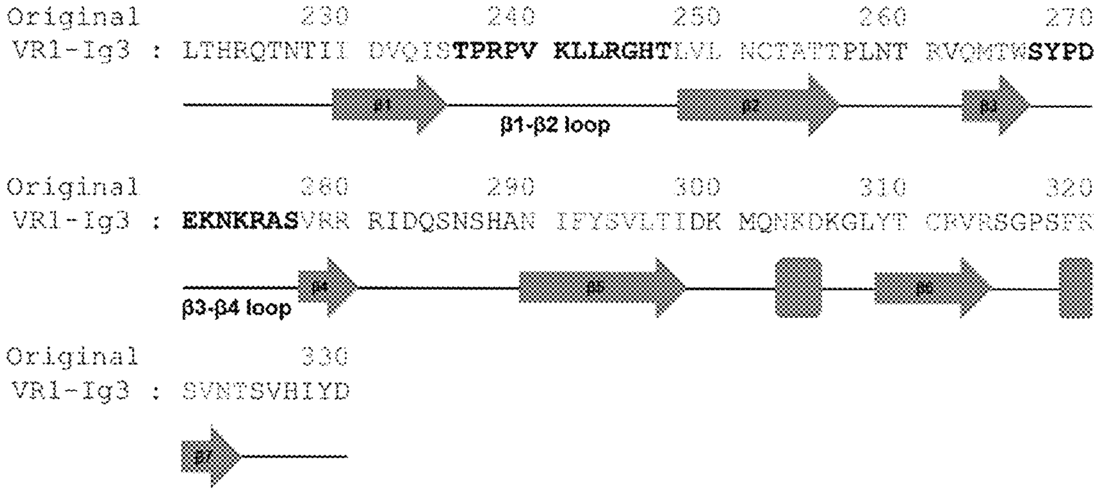
FIG. 2 shows secondary structure of original VEGFR1-Ig3. β strands are shown as arrows and cylinders (green). Residues on β1-β2 and β3-β4 loops of VEGFR1-D3 are displayed as bold.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-⌈-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the ⌈-carboxy or ⌈-amino functional group of the amino acid.

Deletional variants are those with one or more amino acids in the native amino acid sequence removed. Ordinarily, deletional variants will have one or two amino acids deleted in a particular region of the molecule.

As used herein, "antagonist" refers to a ligand that tends to nullify the action of another ligand, as a ligand that binds to a cell receptor without eliciting a biological response.

It is also contemplated that fusion proteins be labeled with a detectable label, such as radioisotope, fluorescent tag, enzymatic tag, or a chemiluminescent tag to determine ligand-receptor binding interaction. As such, assay systems employing the chimeric molecule is also contemplated.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "consisting essentially of" when used in the context of a nucleic acid sequence refers to the sequence that is essential to carry out the intended function of the amino acid encoded by the nucleic acid.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 μg/ml of carrier. In the case of compositions containing supplementary active ingredients, the dosages are determined by reference to the usual dose and manner of administration of the said ingredients.

As used herein, "sample" or "biological sample" is referred to in its broadest sense, and includes any biological sample obtained from an individual, body fluid, cell line, tissue culture, or other source, which may contain any PIGF or VEGF-A binding peptides, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art.

As used herein, "subject" is a vertebrate, preferably a mammal, more preferably a human.

As used herein, "synchronous" or "synchronously" binding refers to the binding of the protein to two or more designated proteins simultaneously if the proteins are available for binding.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

VEGF-Grab

In this study, we developed a novel glycosylated soluble decoy receptor fusion protein containing VEGFR1 D2-D3 and Fc, called VEGF-Grab, which demonstrates a prolonged PK profile and sequesters both VEGF and PlGF. Although VEGFR1 binds to VEGF-A and PlGF with higher affinity than does VEGFR2, the development of therapeutic decoy proteins with the VEGFR1 backbone has proven to be difficult thus far. The major reason behind this was the high pI value VEGFR1 due to the positively charged residues at the VEGFR1 D3 region, in particular, β1-β2 loop and/or β3-β4 loop. This causes non-specific ECM binding and poor PK profiles, leading to a shortened half-life, a subsequent decrease in efficacy, and even toxic side effects. In order to overcome this intrinsic property in VEGFR1 D3, we mutated three positive residues within VEGFR1 D3 loop that were predicted to be irrelevant to ligand binding. These positive residues were altered to become potential glycosylation sites (Ser, Thr or Asn).

Creating new decoy receptor fusion proteins using this glycosylation strategy results in several advantages. First, ECM binding of VEGF-Grab is dramatically decreased by introducing these glycosylation sites into the VEGFR1 D3 region. These sites counterbalance the positively charged residues with negatively charged residues or newly attached negatively charged glycans. In addition, as shown by glycan analysis with mass spectrometry, G3 contains increased sialylation compared with G1 or VT. Terminal sialic acid is critical for in vivo half-life of proteins since the asialoglycoprotein receptors in the liver bind to nonsialylated glycoproteins and remove them from the serum by endocytosis. This lower ECM binding and increased sialylation of G3 appears to facilitate an enhanced PK profile. Specifically, compared to VT, the AUC of G3 were increased by 1.7~1.9-fold, suggesting that bioavailability of G3 are superior to VT. Second, G3 containing the VEGFR1 D2-D3 showed more potent decoy activity against VEGF-A and PlGF, compared to VT; G3 bound 1.5-fold and 6.7-fold higher to VEGF-A and PlGF as compared to VT. This was evidenced by our in vitro experiments demonstrating strong suppression of EC proliferation, migration, and tube formation after treatment with G3. Consistent results were observed in vivo, where G3 showed much stronger anti-angiogenic, anti-tumor, and anti-metastatic effects in both implanted and spontaneous tumor models compared to VT. The binding affinity of G3 to PlGF, which is critical for TAM recruitment, was comparable to that of anti-PlGF antibody, resulting in the decreased macrophage infiltration in G3-treated tumor compared to those treated with VT. Considering that the LLC tumor model is known to be relatively resistant to anti-VEGF therapy, these findings suggest the possibility of overcoming resistance to anti-VEGF therapy by concurrent blockade of PlGF with VEGF-Grab. Third, G3 demonstrated improvements in toxicity profile as compared to the parental VEGFR1-Fc. Ascites formation and mortality were reported with the use of VEGFR1-Fc due to its non-specific interaction with the ECM. During our animal experiments, G3 was treated for long periods lasting 2~3 weeks, with no signs of ascites formation or mortality (data not shown). Furthermore, histologic analyses of vital organs did not reveal any significant differences in comparison to VT (FIG. 18), implying that the toxicity of parental VEGFR1-Fc can be overcome by introducing additional glycosylation. However, adverse effects of systemic anti-VEGF therapy have been reported, including delayed wound healing and hemorrhage. Recently, Sticky-trap, which locally inhibits angiogenesis, has been developed and confirmed to have no systemic side effects. While the potential side effects of G3 in clinics should be carefully studied at varying dosages, time points, and after long-term treatment, it could be further improved by adopting the Sticky-trap concept.

Currently, anti-VEGF agents are approved for clinical use in combination with chemotherapy for the treatment of various tumors. Here, we also demonstrated the potential application of VEGF-Grab as a candidate for combinational chemotherapy with its additive and synergistic effects. In our study, a single administration of VEGF-Grab3 demonstrated an equivalent outcome in vivo murine CNV and OIR model to aflibercept. As VEGF-Trap (aflibercept) was also FDA-approved for the treatment of age-related macular degeneration (AMD) exhibiting higher efficiency than a single approach inhibiting VEGF-A, indicating VEGF-Grab can be also applicable to angiogenic ocular diseases including AMD. In clinical practice, monthly or bimonthly repetitive injections of anti-VEGF agents need to maintain a visual acuity in AMD patients. However, our enhanced PK profile suggests a probability of similar outcomes as aflibercept with a less frequent dose regimen, which is consistent with the rationale that a higher binding affinity could lead to increased durability.

In conclusion, our evidence suggests VEGF-Grab3 is a potent and effective recombinant decoy for both VEGF and PlGF. Through the enhanced PK profile, VEGF-Grab3 showed durable suppression of tumor angiogenesis, growth, and metastasis. Clinical applicability of this novel fusion protein should be explored through further preclinical and clinical studies.

Treatment of Ocular Diseases

Many ocular diseases are also associated with abnormal angiogenesis, vascular leakage and up-regulated VEGF. In one aspect, the inventive glycosylated VEGF decoy receptor fusion protein may be administered to a patient with an eye condition associated with abnormal angiogenesis or vascular leakage. The patient may be a person suffering from unwanted neovascularization in the eye or macular edema.

Exudative Age-Related Macular Degeneration (AMD)

Exudative age-related macular degeneration (AMD) is one of the most important causes of blindness in developed countries and the most clinically critical subtype of AMD. In exudative AMD, the macular region rapidly deteriorates due to abnormal angiogenesis, termed “choroidal neovascularization (CNV)” which arises from the choriocapillaris across the retinal pigment epithelium (RPE) and Bruch’s membrane to subretinal space of macula. CNV is also a major complication that threatens the vision of patients with various retinal degenerative and inflammatory diseases, including pathologic myopia. Additional CNV conditions may include without limitation, myopic choroidal neovascularization, traumatic choroidal neovascularization, uveitic choroidal neovascularization such as ocular histoplasmosis, and idiopathic choroidal neovascularization.

Myopic Choroidal Neovascularization

Myopic CNV is a disease of the retina where new, abnormal blood vessels grow into the retina in persons who are severely myopic (typically more than minus six diopters). The disease is characterized by an abnormally elongated eye with a physical stretching of the sclera, choroid, and retina resulting in degenerative and progressive changes. These degenerative changes can induce rupture in the Bruch’s membrane and the development of choroidal neovascularization. Similar mechanism applies to traumatic CNV.

Uveitic Choroidal Neovascularization

Uveitis is an inflammation of the uvea. CNV is an uncommon complication of uveitis associated with visual impairment that occurs more commonly in forms affecting the outer retina—retinal pigment epithelium—choroid interface, during periods of inflammatory activity, in association with preretinal neovascularization, and in second eyes of patients with unilateral CNV.

Ocular Histoplasmosis

Ocular histoplasmosis and multifocal choroiditis and panuveitis (MCP) syndrome are examples of uveitis that are sometimes complicated by CNV. CNV is the main reason for vision deterioration in those ocular inflammatory diseases.

A fungus is inhaled early in life and causes a usually asymptomatic and self-limited infection throughout the body, including the lungs and choroid (the vascular layer lining the retina). For unknown reasons, several decades after the initial infection, choroidal scars may develop abnormal blood vessels (choroidal neovascularization) which leak fluid and blood. Distorted central vision and loss of reading vision occurs when the leakage involves the macula. A goal of treatment is to prevent choroidal neovascularization (CNV) from spreading into the macular center, or limit the size of and leakage from the CNV once it reaches the macular center.

Idiopathic Choroidal Neovascularization

When new blood vessels originating from the choroid appear to arise spontaneously, without a known cause, the condition is referred to as idiopathic choroidal neovascularization. The new blood vessels may proliferate beneath the retina’s pigment epithelial layer, causing type 1 neovascularization. They may penetrate the pigment epithelial layer and occupy the sub-retinal space beneath the sensory retina, causing type 2 neovascularization. Regardless of underlying causes and locations of growth, neovascularization results in vision loss.

Diabetic Retinopathy and Diabetic Macular Edema

Diabetic retinopathy develops in patients with diabetes mellitus and is the most common cause of blindness in working age population. As the disease progresses, retinal vascular obliteration and hypoxia induces VEGF upregulation and cause retinal neovascularization which is the hallmark of proliferative diabetic retinopathy. Retinal neovascularization usually causes vitreous hemorrhage and retinal detachment, which severely impairs vision. Suppression of VEGF can regress the retinal neovascularization in proliferative diabetic retinopathy. In addition, the high intraocular VEGF concentration can induce vascular leakage and macular edema. Macular edema can impair central vision in patients with diabetic retinopathy and other anti-VEGF agents such as bevacizumab, ranibizumab and aflibercept are known to be effective in the treatment of macular edema.

Retinal Vein Occlusion

There are two types of retinal vein occlusion: branch retinal vein occlusion and central retinal vein occlusion. Retinal vein occlusion is affected by similar pathogenic mechanism as with diabetic retinopathy: retinal capillary occlusion, hypoxia, and VEGF up-regulation. Thus, retinal neovascularization and macular edema often develop in this condition. Other anti-VEGF agents are also known to be effective in treating macular edema from retinal vein occlusion.

Retinopathy of Prematurity

Retinopathy of prematurity is the most common cause of blindness in children. Retinopathy of prematurity is characterized with abnormal retinal neovascularization, which causes tractional detachment of the retina. A traditional treatment method is laser photocoagulation on the ischemic retina to suppress VEGF and abnormal neovascularization. Recently, down-regulation of VEGF using bevacizumab was shown to be effective in regressing neovascularization and in preventing blindness.

Neovascular Glaucoma

Neovascular glaucoma is a blinding complication of ischemic retinopathy such as diabetic retinopathy, retinal vein occlusion and ocular ischemic syndrome. In chronic ocular ischemia, new vessel develops in the iris and in the angle, which blocks the trabecular meshwork and ocular hypertension develops. High intraocular pressure compresses optic nerve head and permanent blindness may develop. This series of pathogenic events leads to neovascular glaucoma. Anti-VEGF agents have been known to be efficacious in the prevention and treatment of neovascular glaucoma.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

Table 1 shows SEQ ID NO:1 nucleic acid sequence and its corresponding amino acid sequence (SEQ ID NO:2) for subdomain assemblies of VEGF-Grab backbone sequence composed of hVEGFR1 signal sequence, VEGFR1 domain 2, VEGFR1 domain 3, and hFC domain portion in order.

Table 2 shows SEQ ID NO:3 nucleic acid sequence and its corresponding amino acid sequence (SEQ ID NO:4) for subdomain assemblies of VEGF-Grab1 composed of hVEGFR1 signal sequence, VEGFR1 domain 2, VEGFR1 domain 3, and hFC domain portion in order with the following mutations in VEGFR1 domain 3: at nucleic acid positions 403~405 (amino acid position 135Ser), and nucleic acid positions 412~414 (amino acid position 138Thr).

Table 3 shows SEQ ID NO:5 nucleic acid sequence and its corresponding amino acid sequence (SEQ ID NO:6) for subdomain assemblies of VEGF-Grab2 composed of hVEGFR1 signal sequence, VEGFR1 domain 2, VEGFR1 domain 3, and hFC domain portion in order with the following mutations in VEGFR1 domain 3: at nucleic acid positions 514~516 (amino acid position 172Asn).

Table 4 shows SEQ ID NO:7 nucleic acid sequence and its corresponding amino acid sequence (SEQ ID NO:8) for subdomain assemblies of VEGF-Grab3 composed of hVEGFR1 signal sequence, VEGFR1 domain 2, VEGFR1 domain 3, and hFC domain portion in order with the following mutations in VEGFR1 domain 3: at nucleic acid positions 403~405 (amino acid position 135Ser), nucleic acid positions 412~414 (amino acid position 138Thr), and nucleic acid positions 514~516 (amino acid position 172Asn).

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, HEK or CHO cell.

The present invention also provides for methods of producing the fusion polypeptides of the invention by growing cells of the host-vector system described herein, under conditions permitting production of the fusion polypeptide and recovering the fusion polypeptide so produced. The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity, which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. The potential glycosylation amino acids include serine, threonine, and asparagine. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electroporation, or microinjection techniques.

In addition, the present invention contemplates use of the fusion polypeptides described herein in tagged form.

Any of the methods known to one skilled in the art for the insertion of DNA fragments into a vector may be used to construct expression vectors encoding the fusion polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a fusion polypeptide as described herein, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The fusion polypeptide, in particular modified of the present invention, may be expressed in the host cells transiently, constitutively or permanently.

The invention herein further provides for the development of a fusion polypeptide as a therapeutic agent for the treatment of patients suffering from disorders involving cells, tissues or organs which express the VEGF-A, VEGF-B and/or PlGF. Such molecules may be used in a method of treatment of the human or animal body, or in a method of diagnosis.

Effective doses useful for treating these or other diseases or disorders may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions, which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

In a specific embodiment, nucleic acids comprising sequences encoding the inventive chimeric molecule, by way of gene therapy to inhibit angiogenesis. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode VEGF-Grab, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for various diseases that are characterized by unwanted blood vessel formation. In this way, the inventive therapeutic compound may be administered to human patients who are either suffering from, or prone to suffer from the disease by providing a molecule that bind to VEGF-A, VEGF-B and/or PIGF.

The formulation of therapeutic compounds is generally known in the art and reference can conveniently be made to Remington's Pharmaceutical Sciences, 17th ed., Mack Publishing Co., Easton, Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intra ocular, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, intra ocular, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), sulphur ($^{35}S$), tritium ($^{3}H$), indium ($^{112}In$), and technetium ($^{99m}Tc$), and fluorescent labels, such as fluorescein and rhodamine, and biotin.

Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is preferred isotope where in vivo imaging is used since its avoids the problem of dehalogenation of the $^{125}I$ or $^{131}I$-labeled polypeptide by the liver. In addition, this radionucleotide has a more favorable gamma emission energy for imaging. For example, $^{111}In$ coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}Gd$, $^{55}Mn$, $^{162}Dy$, $^{52}Tr$, and $^{56}Fe$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (Clin. Chim. Acta 70:1-31 1976 and Schurs et al. Clin. Chim. Acta 81:1-40, 1977). Coupling techniques include the glutaraldehyde method, the periodate method, the dimaleimide method, the m-maleimidobenzyl-N-hydroxy-succinimide ester method, all of which methods are incorporated by reference herein.

The polypeptides and antibodies of the present invention, including fragments thereof, may be used to detect VEGF-Grab/ligand complex using biochip and biosensor technology. Biochip and biosensors of the present invention may also comprise antibodies, which specifically recognize the polypeptides of the present invention to detect VEGF-Grab/ligand complex.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—Materials and Methods

Example 1.1—Cell Lines

All cell lines for this studies (HUVEC (CC-2519, Lonza), dhfr-deficient CHO cells (CRL-9096, ATCC) and LLC cells (CRL-1642, ATCC)) have not been cultured for longer than 6 months.

Example 1.2—Generation of Recombinant Proteins

Human VEGFR1 (amino acid residues 132-331) fused to human Fc domain of IgG1 (referred to as Fc) was cloned into the pCMV-dhfr vector. A series of VEGF-Grabs were generated by site directed mutagenesis. VEGF-Grabs constructs were transfected into dhfr-deficient CHO cells. Transfected cells were selected by G418, and genes were amplified by gradually increasing methotrexate treatment (0.001-0.5 μM). The cells were then grown in HyQSFM4CHO (ThermoScientific) media containing 0.5 μM methotrexate. VEGF-Grabs and VEGF-Trap were purified by protein A-sepharose affinity chromatography. Purified proteins were quantitated using Bradford assay and confirmed by Coomassie blue staining after SDS-PAGE.

Example 1.3—Isoelectric Focusing Analysis

To analyze isoelectric points of VEGF Grabs (G1 and G3) and VEGF Trap (VT), 5 μg of proteins and IEF marker (Novex) were loaded on IEF gels ranging pH 3-10 (Novex) and run at 100V for 1 hr, 200V for 1 hr and 500V for 30 min. After electrophoresis, gels were stained with silver staining kit (Elpis).

Example 1.4—In Vitro ECM Binding Assay

Serially diluted G1, G3 or VT (5-80 nM) were treated to the ECM-coated plate (Becton Dickinson). After washing, HRP conjugated goat anti-human Fc antibody was added and TMB solution was added. The absorbance was measured by ELISA reader at 450 nm.

Example 1.5—In Vivo ECM Binding Assay 100 nM of VR1-Fc, VT, or G3 were treated to the tumor sections which were not treated with any protein therapeutics, and the nonspecifically bound VR1-Fc, VT, or G3 were detected with an anti-human Fc-cy3 antibody. As an ECM marker, collagen type IV that is a collagen primarily found in basal lamina of ECM was counterstained with FITC.

Example 1.6—Solid Phase Binding Assay

The binding affinities of VEGF-Grabs to ligands were measured by ELISA as described previously. Briefly, the MaxiSorp plates (Nunc) were coated with either hVEGF-$A_{165}$(150 ng/ml), PlGF (62.5 ng/ml), or hVEGF-B (125 ng/ml) and serially increasing amounts (0.1 nM-10 μM) of VEGF-Grabs or VEGF-Trap were added. After washing, the plates were incubated with HRP-conjugated goat anti-human Fc antibody. Then, 3,3',5,5'-tetramethylbenzidine (TMB) solution (Sigma-Aldrich) was added and absorbance was measured by ELISA reader (BioRad) at 450 nm.

Example 1.7—Generation of De-N-Glycosylated Peptides

Glycoproteins were thermally denatured, followed by reduction and alkylation using dithiothreitol and iodoacetamide, respectively. Trypsin (Promega, Madison, Wis.) was added at an enzyme-to-protein ratio of 1:50 (w/w) and the mixture was incubated at 37° C. for 16 h. Peptides/glycopeptides were enriched by a C18 peptide trap (Michrom, Auburn, Calif.) and dried by speedvac. N-glycopeptides were deglycosylated by incubation with 2 μL peptide N-glycosidase F (New England Biolabs, Ipswich, Mass.) at 37° C. for 16 h. Peptides were enriched by a C18 peptide trap (Michrom, Auburn, Calif.) and dried by speedvac.

Example 1.8—Enzymatic Release of N-Glycans

N-glycan release and associated processing steps were carried out as previously described. Briefly, glycoproteins were thermally denatured and reduced in an aqueous solution of ammonium bicarbonate and dithiothreitol prior to digestion by peptide N-glycosidase F at 37° C. for 16 h.

Example 1.9—Enrichment of Glycans and Short Glycopeptides with Graphitized Carbon SPE Released glycans and glycopeptides were purified by graphitized carbon solid-phase extraction according to previously optimized procedures. Briefly, graphitized carbon cartridges (Grace Davison, Deerfield, Ill.) were conditioned with water; loaded with aqueous N-glycan solutions; and washed with water. N-glycans were eluted stepwise with 20% acetonitrile in water, followed by 40% acetonitrile and 0.05% trifluoroacetic acid (v/v) in water. Samples were dried by speedvac.

Example 1.10—Immunoblotting for Detecting VEGFR2 Activation

When HUVECs grown in EGM-2 (Lonza) became confluent, cells were starved overnight in OPTI-MEM (Invitrogen). VEGF-Grabs or VEGF-Trap (2 μg/ml, 14 nM) was then treated for 15 min followed by VEGF-A treatment (50 ng/ml, 1 nM) for 10 min. After the treatment, cells were washed with 1×PBS and lysed in lysis buffer. Then, 50 μg of total proteins were loaded on 10% SDS-PAGE, transferred onto nitrocellulose membrane, and immunoblotted with anti-phospho-VEGFR2 and anti-phospho-ERK1/2 antibody (Cell signaling). After stripping, VEGFR2 and ERK1/2 were also immunoblotted.

Example 1.11—Migration Assay

HUVECs were seeded on the culture-insert of μ-dish (Ibidi). When cells became confluent, the culture-inserts were removed. Then migrated cells within the wound were monitored for 12 hr in the presence of VEGF-A (50 ng/ml, 1 nM) and indicated proteins (2 μg/ml, 14 nM) in EBM-2 (Lonza).

Example 1.12—Tube Formation Assay

Matrigel with reduced growth factor (BD Biosciences) was coated onto 24-well plate. HUVECs were seeded ($5\times10^4$ cells per well) and treated with VEGF-Grabs or VEGF-Trap (2 μg/ml, 14 nM). After 15 min, VEGF-A (50 ng/ml, 1 nM) was added and incubated for 12 hrs. The images were taken under a microscope.

Example 1.13—Cell Survival Assay

When the seeded HUVECs became confluent, cells were starved in OPTI-MEM (Invitrogen) concurrently treated with VEGF-Grabs or VEGF-Trap (0.35, 0.7, 3.5, 7, 35, and 70 nM) in the presence or absence of VEGFA (0.2 nM). After 36 hr, WST-1 (water-soluble tetrazolium salt, DOGEN) was added and absorbance was measured at 450 nm.

Example 1.14—Migration Assay

Seventy μl of HUVECs at a density of $5\times10^5$ cells/ml were seeded on the culture-insert of μ-dish (Ibidi). When cells became confluent, the culture-inserts were removed. Then migrated cells within the wound were monitored for 12 hr in the presence of VEGF-A (50 ng/ml) and indicated proteins (2 μg/ml) in EBM-2 (Lonza). The images were taken under a microscope.

Example 1.15—Mice

Specific pathogen-free (SPF) male C57BL/6J and female MMTV-PyMT transgenic mice (FVB/N) were purchased from Jackson Laboratory. All mice were anesthetized with 80 mg/kg of ketamine and 12 mg/kg of xylazine, before sacrifice. Particularly for ocular experiments, a total of 15 Male C57BL/6J mice, six-week-old, weighing 18-20 g were used. All mice were treated in accordance with the Association for Research in Vision and Ophthalmology (ARVO) Statement for the Use of Animals in Ophthalmic and Vision Research. All animal care and experimental procedures were performed under the approval (KA2013-42) from the Animal Care Committee of KAIST.

Example 1.16—PK Analysis

C57BL/6J mice (~25 g) were given subcutaneous injections of 4, 10, or 25 mg/kg VEGF-Grabs and VEGF-Trap. Blood samples were collected from tails at 1, 2, 4, 8, 12, 24, 48, 96 and 144 hr after injection. The protein levels in serum were measured with ELISA.

Example 1.17—Tumor Models and Treatment Regimes

Murine Lewis lung carcinoma (LLC) cells ($1\times10^6$ cells in 100 μl) were subcutaneously injected into the dorsal flank of mice (8 to 10-weeks old). Tumor volume was calculated according to the formula: 0.5×length×width. VEGF-Grab3 or VEGF-trap (indicated dose) was intraperitoneally injected at given time points. For the combined therapy of G3 with chemotherapeutics, cisplatin (10 mg/kg, Sigma-Aldrich) was intraperitoneally injected at day 9 into LLC tumor-bearing mice that were receiving injections of either VT, or G3. Female MMTV-PyMT mice (12-weeks old) received IP-injections of either VT, or G3 (25 mg/kg) twice per week for 3 weeks to test its anti-cancer effects in spontaneous breast cancer model. Mice were anesthetized and their primary tumors, LNs, and organs were harvested for histological analyses. Animal care and experimental procedures were performed under the approval (KA2013-42) from the Animal Care Committee of KAIST.

Example 1.18—Quantitative Real-Time PCR

Total RNA was extracted from the tumor samples using RNeasy plus mini kit (Qiagen) followed by cDNA synthesis with SuperScriptII reverse transcriptase (Invitrogen). Quantitative real-time PCR was performed with indicated primer pairs (Table 5 for the primer sequences) by using TOPreal™ qPCR SYBR premix (Enzynomics) and CFX96 real-time PCR detection system (Bio-Rad). The results of the real-time PCR were analysed with CFX manager software (Bio-Rad).

Example 1.19—Histological Analyses

Tumors were processed and stained as previously described. Frozen samples were sectioned and then stained with antibodies (See Table 6 for detailed information of antibodies). For the visualization of hypoxic areas in the tumors, Hypoxyprobe-1™ (60 mg/kg, solid pimonidazole hydrochloride, Hypoxyprobe) was intravenously injected 90 min before sacrifice. The tumors were harvested, sectioned, and stained with FITC-conjugated anti-Hypoxyprobe antibody. The $CD11b^+$, $cytokeratin^+$, and $caspase3^+$ areas were calculated as a percentage per total sectional area.

Example 1.20—Ocular Treatment Procedure

C57BL/6J mice subjected to diode 532 nm laser treatment (Lumenis Inc., Santa Clara, Calif.) after general anesthesia. After a drop of 0.5% tropicamide and 0.5% phenylephrine (Mydrin-P®; Santen Pharmaceutical, Osaka, Japan) is instilled in each eye of each mouse to dilate the pupils, CNV was induced by rupturing the RPE and the underlying Bruch's membrane. Disruption of Bruch's membrane was induced using a power of 100 mW, a spot size of 75 μm and duration of 100 ms to 2.0 times of disc diameters apart from the optic disc. For CNV suppression analysis, the mice were then randomly divided into three groups: the VEGF-Trap-treated group that was intravitreally administered commercially available drug—Eylea® (Aflibercept) (concentration, 25 mg/ml; dose, 2 μl) Aflibercept is dissolved in an isosmotic liquid (10 mM sodium phosphate, 40 mM sodium chloride, 0.03% polysorbate 20, and 5% sucrose [pH 6.2]); the VEGF-Grab3-treated group that was intravitreally administered VEGF-Grab3 (concentration, 25 mg/ml; dose, 2 μl); and the control group that was treated with phosphate-buffered saline (PBS) (2 μl). OIR model was established in the mouse by oxygen induction as described previously. Briefly, litters of 7-day-old [postnatal day 7 (P7)] C57BL/6J mice neonates and their mothers were placed in a closed high-oxygen chamber for 5 days. An oxygen concentration of 75% was maintained and the mice were fed a standard mouse diet and water ad libitum. Then, pups and their mothers were removed at P12 returned to room air (normoxia) conditions. For OIR regression analysis, the mice were then randomly divided into three groups: the VEGF-Trap-treated group that was intravitreally administered commercially available drug—Eylea® (Aflibercept) (concentration, 25 mg/ml; dose, 1 μl); the VEGF-Grab3-treated group that was intravitreally administered VEGF-Grab3 (concentration, 25 mg/ml; dose, 1 μl); and the control group that was treated with phosphate-buffered saline (PBS) (1 μl). At P17, the mice were euthanized for analyses.

Example 1.21—Ocular Sample Excision and Processing

Two weeks after laser photocoagulation for CNV model and 17 days after OIR pups were born, all mice were anesthetized and perfused through the left ventricle with 1 mL PBS containing 25 mg/mL of fluorescein isothiocyanate (FITC)-labeled dextran ($2\times10^6$ average molecular weight, Sigma, St. Louis, Mo.). After sacrifice of the mouse by cervical dislocation, the eyes were enucleated and fixed in 2% paraformaldehyde (PFA) in PBS for 5 minutes at room temperature. Under a dissecting microscope the cornea, lens and vitreous were removed. The open eyecup was inserted in a 1% PFA solution for 20 minutes. The remaining retina/choroid/sclera complex was placed on the glass slide. Four radial incisions in the retina/choroid/sclera eyecup were made to prepare a flat mount. The retina was gently separated from the underlying RPE/choroid/sclera and separately flat mounted. In order to evaluate the choroidal and retinal vasculature, incubation with hamster anti-PECAM-1/CD31 (hamster anti-mouse, clone 2H8, MAB1398Z, Millipore, 1:200) was performed. In short, after blocking with PBS containing 0.4% Triton X-100 (Sigma-Aldrich, St. Louis, Mo.), 5% normal goat serum (DAKO, Hamburg, Germany), and 20% dimethyl sulfoxide (DMSO; Sigma, St. Louis, Mo.), the RPE/choroid/sclera flat-mounts were incubated 2 days at 4° C. with hamster anti-PECAM-1/CD31 primary antibody in blocking buffer. Anti-PECAM-1/CD31 antibody binds to the surface of endothelial cells and selectively labels the murine vasculature. After washing with PBS, flat mounts incubated 2 days at 4° C. with tetramethylrhodamine isothiocyanate (TRITC)-conjugated goat anti-american hamster IgG (Jackson ImmunoResearch Laboratories, Inc., 1:200) as a secondary antibody in blocking buffer. After washing with PBS, the cell nuclei were stained with 10 μg/ml 4'6-diamidino-2-phenylindole (DAPI, Sigma).

Example 1.22—Antibodies

Antibodies used in this study are listed in Table 6.

Example 1.23—Imaging and Quantification

The flat mounts were then examined for CNV. Z-stack images were then captured using scanning laser confocal microscopy (Zeiss—LSM780, Zeiss, Jena, Germany). The vasculature filled with FITC-labeled dextran stained green and CNV complexes were identified using the red channel (anti-PECAM-1/CD31 antibody conjugated TRITC). Images of CNV in choroidal flat mounts were digitalized using an image capture program (LSM Image Browser, Zeiss). Anti-PECAM-1/CD31 antibody conjugated TRITC stained red color area confirms the CNV existence. The total area (in $\mu m^2$) of FITC-labeled dextran stained green color lesion was calculated and compared using an image analysis program (Image-J software, NIH, USA). Whole retinal tile-scan images of OIR pups' retinal flat mounts were also obtained using scanning laser confocal microscopy. And then, the retinal vascular intensity was calculated using an image analysis program (Image-J software, NIH, USA).

Example 1.24—Statistical Analyses

Values are presented as mean±SD. Statistical differences between means were determined by independent sample t-test or analysis of variance with one-way followed by the Student-Newman-Keuls or Bonferroni test. Statistical significance was set at $p<0.05$.

Example 2—Results

Example 2.1—Design of VEGF-Grab and their Enhanced Binding Affinities for VEGF-A and PlGF Both VEGFR1 and VEGFR2 have seven immunoglobulin (Ig)-like domains in the extracellular domain (FIG. 1A). Among them, VEGFR1 D2 is the primary contributor to VEGF-A and PlGF binding. In addition, residues in VEGFR1 D3 also participate in the high affinity binding of VEGF-A and PlGF. Therefore, the VEGFR1 D2-D3 is the minimal required domain to bind both VEGF-A and PlGF with high affinity. To design a novel VEGF decoy receptor fusion protein, w e first analysed the model structures of VEGFR1 D2-D3/VEGF-A complex generated by MODELLER using template structures (PDB ID: 1FLT and 2X1X) (FIGS. 1B and C). The electrostatic potential analysis revealed that VEGFR1 D3 has abundant positively charged amino acids (shown in blue), responsible for the high pI of this domain compared to VEGFR2 D3 (FIG. 1B). Using VEGFR1, we designed VEGF decoy receptor fusion protein, called VEGF-Grab. VEGF-Grab includes hVEGFR1 signal sequence (amino acids from 1 to 26, nucleotides from 1 to 78 which is taken from amino acids from 1 to 26 (nucleotides from 1 to 78) of the original hVEGFR1), hVEGFR1 D2-D3 domain (amino acids from 27 to 229, nucleotide from 79 to 687 which is taken from amino acids from 132 to 332 (nucleotides from 394 to 996) of the original hVEGFR1), and Fc domain of human IgG (amino acids from 230 to 459, nucleotides from 688 to 1377). In an attempt to reduce the net pI of VEGFR1 D3 and improve in vivo half-life of VEGF decoy receptor fusion protein, we targeted residues for mutagenesis located on β1-β2 and β3-β4 loops of VEGFR1-D3 (FIG. 2) because the model structure of the VEGF-A/VEGFR1 D2-D3 complex shows that the β1-β2 loop of hVEGFR1 D3 domain (amino acids from 133 to 144 of SEQ ID NO:2, nucleotides from 397 to 432 of SEQ ID NO:1, which is taken from amino acids 236 to 247 (nucleotides 706 to 741) of the original hVEGFR1) and the β3-β4 loop of hVEGFR1 D3 domain (amino acids from 164 to 174 of SEQ ID NO:2, nucleotides 490 to 522 of SEQ ID NO:1, which is taken from amino acids from 267 to 277 (nucleotides from 799 to 831) of original hVEGFR1) are not involved in ligand binding but are located within the flexible loops as well as contain many positive residues. Thus, it was predicted that charge conversion mutations on these loops of VEGF-Grab would maintain their high affinities to VEGF-A/PlGF, reduce the net pI of VEGFR1 D3 domain and avoid structural disruption (FIG. 1C). In addition to the charge conversion mutation, another rationale for the mutagenesis on these loop is the mutation to Serine, Threonine or Asparagine to be a potential 0- or N-glycosylation site which can improve protein half-life.

Figure 10:
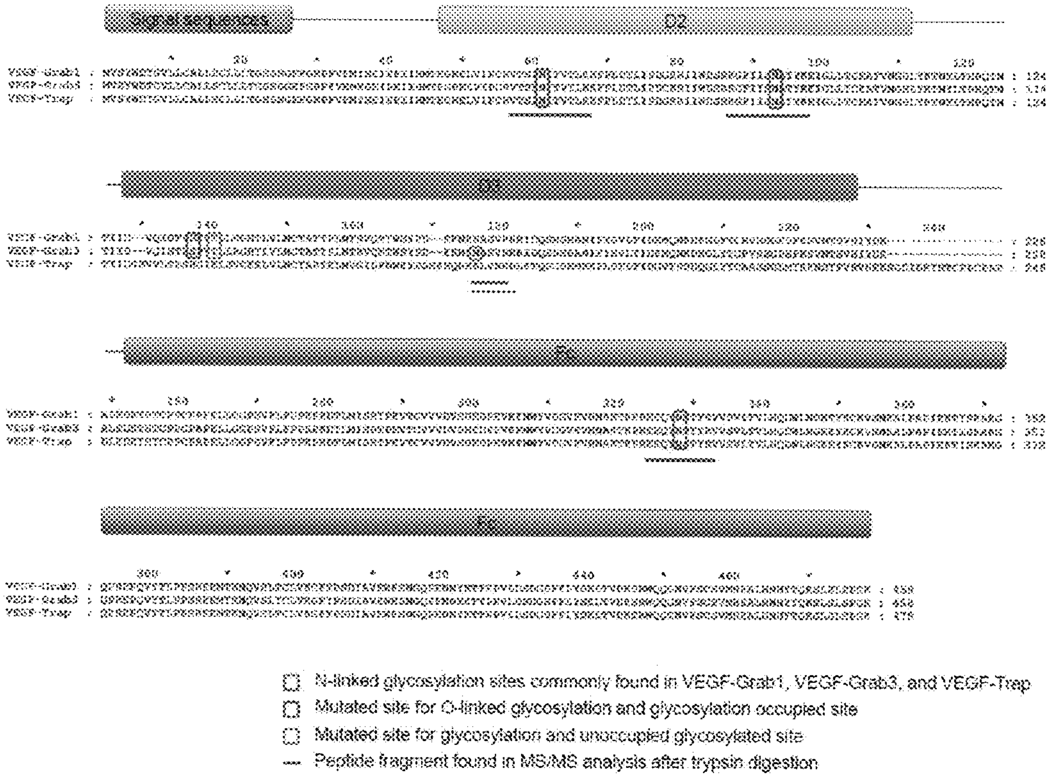
FIG. 10 shows sequence alignment of VEGF-Grab1, VEGF-Grab3, and VEGF-Trap. Amino acid sequences of G1, G3, and VT were aligned using CLUSTALW. Signal sequences, D2, D3, and Fc domains are shown above the sequence alignment. N-linked glycosylation sites detected by mass spectrometry in all proteins are highlighted by the red box. The mutated site occupied by O-linked glycosylation is highlighted by the blue box. The mutated sites for glycosylation that are unoccupied by glycans are highlighted by the grey box. The peptide fragments analysed by MS spectrometry after trypsin digestion are shown below the sequence as brown lines (See FIG. 11A for additional description).

To test these ides, we generated three VEGFR1 variants; VEGF-Grab1, VEGF-Grab2, and VEGF-Grab3 (FIG. 1A). Three positive-charged residues—R135, K138 and the R172, within the VEGFR1 D3 loop region were mutated to negative-charged residues (R135S, K138T and R172N) where glycans could be attached (FIG. 1A and FIG. 10). All VEGF-Grab constructs consist of VEGFR1 D2-D3 variants fused to Fc (FIG. 1A). Unfortunately, the expression levels of parental VEGFR1-Fc and VEGF-Grab2 in CHO cells were too low, so further analyses were performed only with VEGF-Grab1 and VEGF-Grab3. All of the proteins—VEGF-Grab1, VEGF-Grab3, and VEGF-Trap (hereafter, abbreviated as G1, G3, and VT, respectively), were produced from CHO cell and purified by ProteinA affinity chromatography. Purified G1 and G3 showed diffuse band patterns in reduced SDS-PAGE condition (FIG. 1D), which is a typical characteristic of glycosylated proteins. Under non-reduced conditions, VEGF-Grabs displayed a dimeric form due to the disulfide bond in the Fc (FIG. 1D). The in vitro binding affinities of VEGF-Grabs and VT to pro-angiogenic ligands—VEGF-A, PlGF, and VEGF-B, showed that G1 ($K_D$=7.9×$10^{-10}$ M) and G3 ($K_D$=5.6×$10^{-10}$ M) had 1.1 and 1.5-fold higher affinity to VEGF-A than VT ($K_D$=8.4×$10^{-10}$ M) (FIG. 1E). However, the binding affinities of G1 and G3 to VEGF-B, which only requires VEGFR1-D2 for binding, were similar to VT (FIG. 1G). Intriguingly, the binding affinities of G1 ($K_D$=2.8×$10^{-9}$ M) and G3 ($K_D$=6.9×$10^{-9}$ M) to PlGF were 18.5 and 6.7-fold more potent than VT ($K_D$=4.6×$10^{-8}$ M), respectively (FIG. 1F), suggesting that we successfully generated new glycosylated-VEGF decoy receptor fusion proteins, G1 and G3, which have significantly higher affinities to both VEGF-A and PlGF.

Example 2.2—Identification of Newly Added O-Glycan on VEGF-Grabs

Figures 3A, 3B, 3C, 3D, 3E:
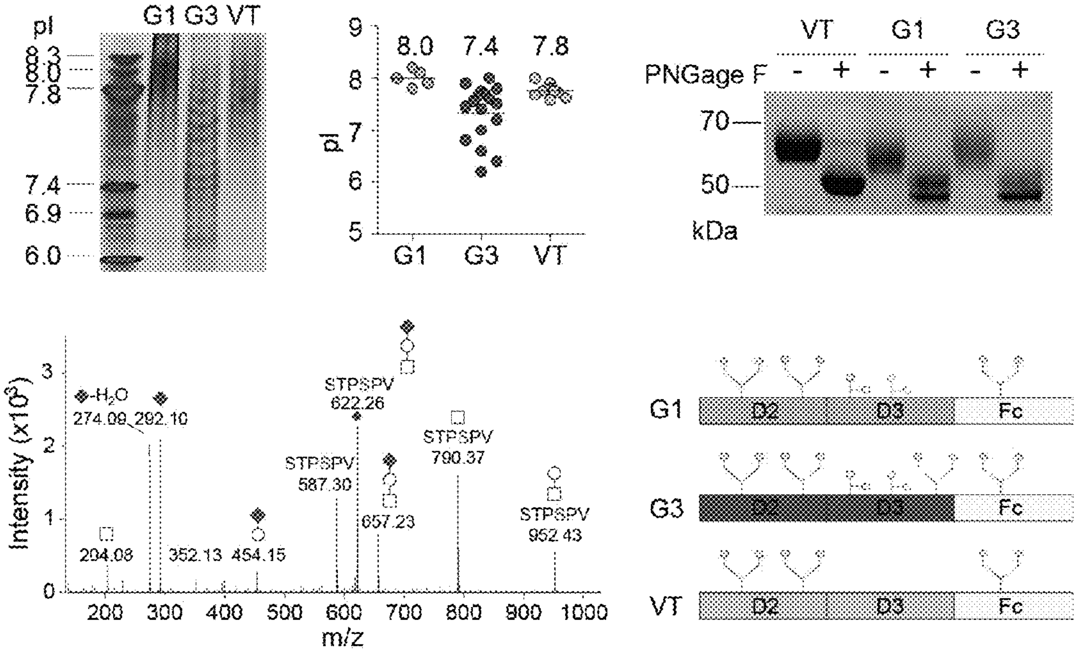

Because glycosylation can alter the pI of proteins, we measured the pI of the VEGF-Grabs. Due to the diverse composition of attached glycans, VT, G1, and G3 exhibited micro-heterogeneity with diverse isoform on the isoelectric focusing gel (FIG. 3A). Intriguingly, the pIs of G1 and G3 were dramatically decreased to 8.0 and 7.4, respectively (FIG. 3B), compared to that of parental VEGFR1-Fc (pI: 9.4). These pI values were comparable to that of VT (pI: 7.8). After digestion with PNGaseF, the molecular weights of the VEGF-Grabs and VT were decreased (FIG. 2C), indicating the presence of N-linked glycosylation in VT, G1, and G3. In contrast to VT, even after PNGaseF digestion, G1 and G3 still displayed diffuse band patterns suggesting their O-linked glycosylation.

Figure 12:
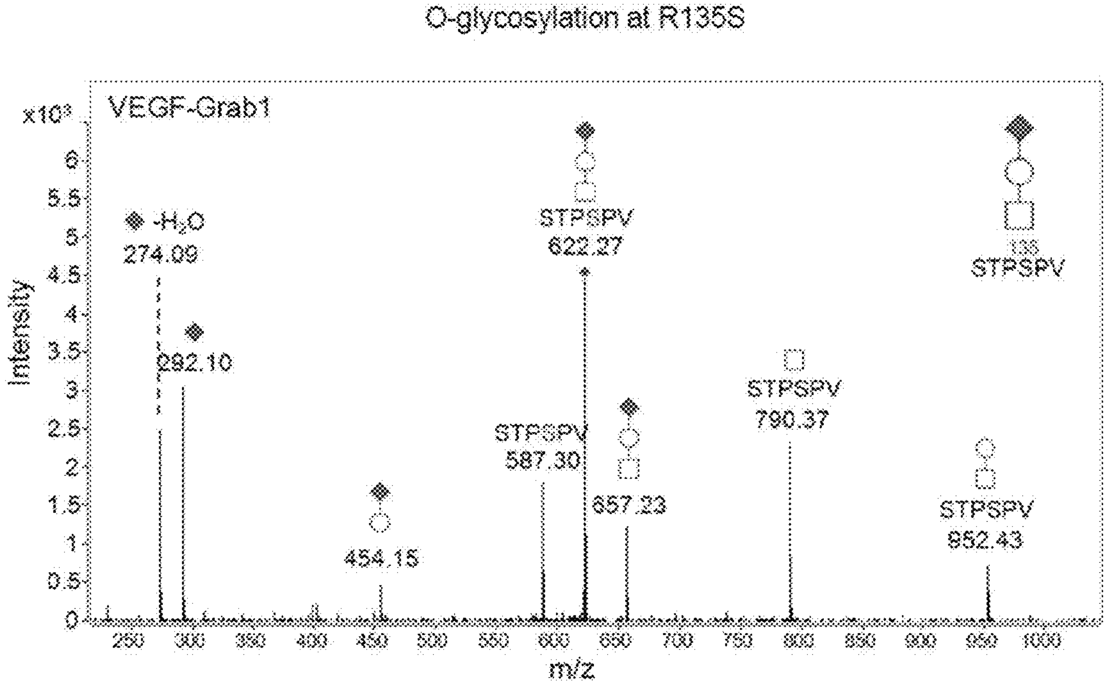
FIG. 12 shows analysis of O-linked glycosylation in VEGF-Grab1. Tandem MS spectrum of G1 glycopeptide. O-linked glycosylation at the Serine135 was detected. Extensive peptide and glycan fragmentation enabled complete site- and structure-specific assignment. Square=N-acetylhexosamine, circle=hexose, and diamond=sialic acid.

To further confirm the presence of N- or O-glycans at the mutated sites of VEGF-Grabs, w e performed a mass spectrometry for glycosylation mapping. Calculated masses of both deglycosylated and unglycosylated tryptic peptides that encompass a potential site for N-glycosylation are listed in FIG. 11A. LC/MS data indicates that the mutated Asn172 on G3 was not glycosylated, whereas three original N-glycosylation sites, Asn61, Asn93, and Asn308 (Asn328 for VT), were all fully occupied (FIG. 3E and FIG. 10). Next, using Glyco-Analytical Multispecific Proteolysis (glyco-AMP), we determined whether Ser135 and Thr138 of the VEGF-Grabs were 0-glycosylated. From the MS/MS spectrum, O-glycopeptide (STPSPV+HexNAc1Hex1NeuAc1) were observed in both G1 and G3 (FIG. 3D and FIG. 12). Typical glycan fragments for HexNAc, NeuAc-H2O, NeuAc, Hex1NeuAc1, and HexNAc1Hex1NeuAc1 confirmed that VEGF-Grabs are O-glycosylated at Ser135. However, we found no evidence of O-glycosylation at Thr138.

We then analysed the overall N-glycan compositions of G1, G3, and VT. N-glycan profile was quantified by both nano-LC/MS and MALDI-MS. This data indicated that G1 and G3 exhibited an increase in high mannose (HM) glycosylation, a decreased in fucosylaed, and complex-undecorated glycans (C/H-Fuc) as compared to VT (FIG. 11B). Particularly, G3 displayed increased sialylation compared to G1 leading to G3's lower pI as compared to G1 (FIG. 3A). This mass spectrometry analysis showed that both G1 and G3 have only one additional O-glycosylation site (Ser135) among the mutated residues (FIG. 3E and FIGS. 10-12), as well as three N-glycosylation sites at 61N, and 93N in VEGFR1 D2 and 308N (328N for VT) in the Fc. In addition, G3 was revealed to be more sialylated than VT or G1.

Example 2.3—VEGF-Grab3 Exhibits Decreased ECM Binding and Enhanced PK Profiles

Figure 13:
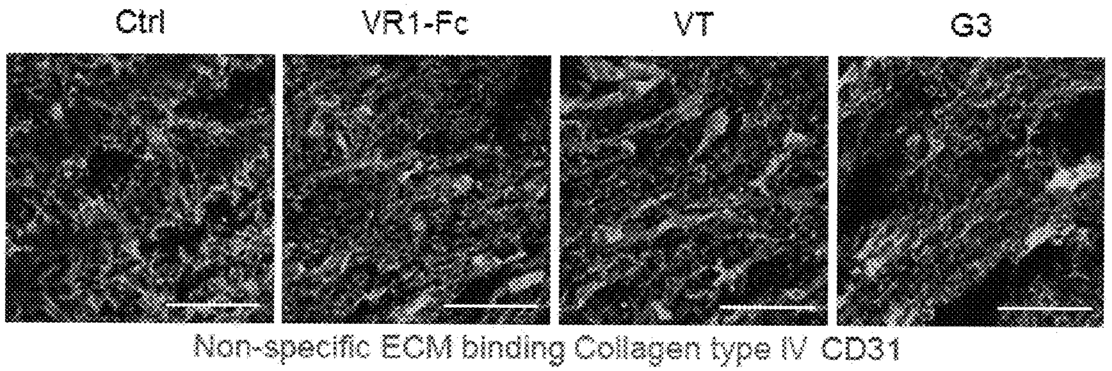
FIG. 13 shows that VEGF-Grab3 displays low binding to tumor ECM. Control tumor sections which were not treated with any protein therapeutics, were stained with 100 nM of VR1-Fc, VT, or G3 and subsequently visualized using the anti-human Fc-cy3 antibody to detect non-specific binding (red) of these molecules to tumor ECM. Collagen type IV (green) is a collagen primarily found in the basal lamina of the ECM. Scale bars, 100 μm.
Figure 14:
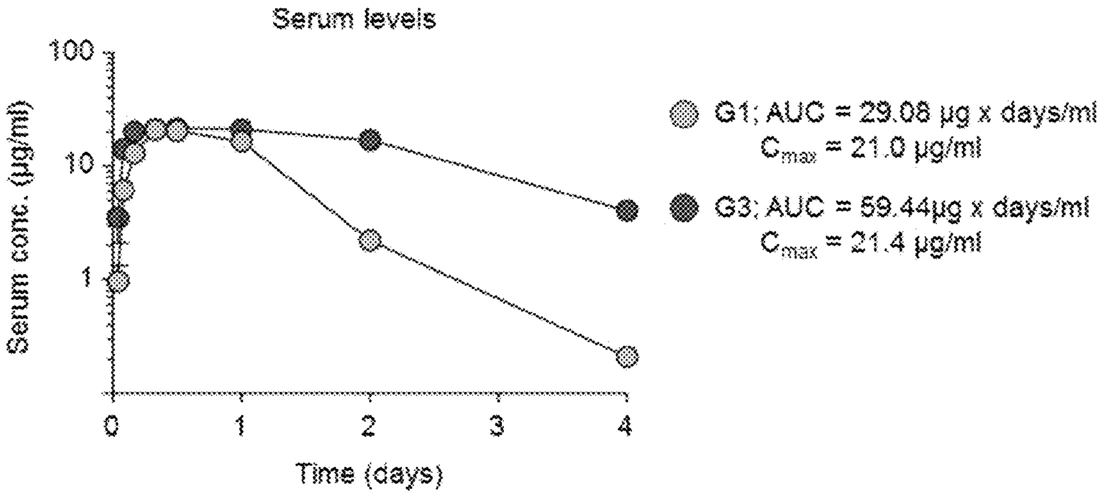
FIG. 14 shows pharmacokinetic profile of VEGF-Grab1 and VEGF-Grab3. Serum levels of G1 after subcutaneous injection of 4 mg/kg. Blood was sampled at 0, 1, 2, 4, 8, 12, 24, 48, and 96 hr, and analysed by ELISA.
Figure 15A:
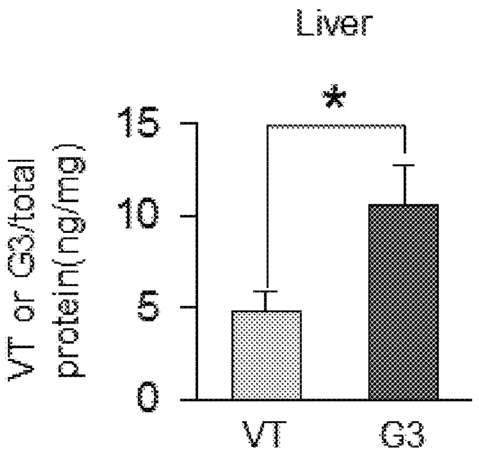
FIGS. 15A-15B show tissue accumulation of VEGF-Trap and VEGF-Grab3.
Figure 15B:
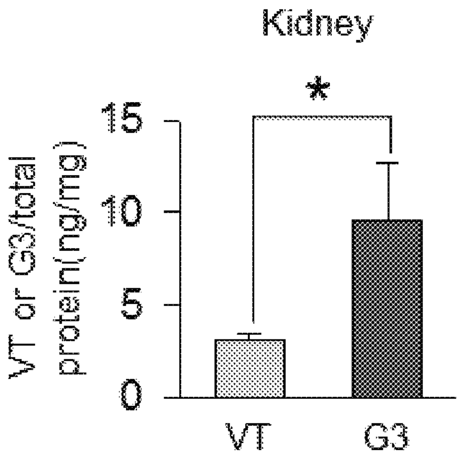

Proteins with high pI values bind non-specifically to the ECM, resulting in poor PK and bioavailability. We confirmed that the reduced pI values of VEGF-Grabs indeed led to the decreased in vitro ECM binding, comparable to that of VT (FIG. 3K). To demonstrate the reduced in vivo ECM binding of G3, we stained control tumor sections with 100 nM of parental VEGFR1-Fc, VT, or G3. While VEGFR1-Fc bound to the tumor section non-specifically, no VT or G3 were detected in the tumor section (FIG. 13). These data confirmed lower ECM binding of both G3 and VT in vivo, suggesting that the charge conversion at the three mutation sites and additionally added glycans to Ser135 of G3 allowed it to effectively overcome the intrinsic problems of VEGFR1-Fc, non-specific binding to ECM. To test whether G1 and G3 displayed an improved in vivo half-life, we analysed their PK profiles at 4 mg/kg dose for 4 days. Interestingly, G3 displayed improved PK profiles (area under the curve (AUC): 59.44 μg×days/ml) compared to G1 (AUC: 29.08 μg×days/ml) (FIG. 14). Therefore, we chose G3 for further in vivo anti-cancer studies. Then, we evaluated the PK profiles of VT and G3 at varying doses (4, 10, 25 mg/kg) for 6 days (FIGS. 3 F and G). VT showed an AUC of 37.57, 34.07, and 65.02 μg×days/ml, whereas G3 showed an AUC of 64.36, 65.68, and 117.5 μg×days/ml after 4, 10, and 25 mg/kg injections, respectively (FIG. 3H). This reflected a 1.7-, 1.9-, 1.8-fold increase over VT, respectively. This enhanced PK profile of G3 also supports low ECM binding of G3 in vivo. Moreover, PK profiles demonstrated that VT was mostly eliminated by 6 days post-injection, while G3 levels at day 6 remained 2-5 fold higher than VT (FIGS. 3F and G), indicating that G3 has a prolonged half-life in serum. We also examined the accumulated levels of VT and G3 in liver, kidney, tumor and urine of LLC tumor-bearing mice 48 hr after subcutaneous injections (4 mg/kg). Higher G3 levels were detected in liver, kidney, and particularly in tumor (18.9-fold increase) than for VT (FIG. 2I and FIG. 15). However, the relative amounts of accumulated G3 in liver and kidney versus tumor were much lower than that of VT (FIG. 3J), suggesting that most G3 accumulate at the tumor site, where VEGF-A and PlGF are predominantly produced. No G3 or VT were detected in urine under our experimental conditions. Taken together, these findings suggest that VEGF-Grab3 has lower ECM binding properties and prolonged half-life.

Figure 4A:
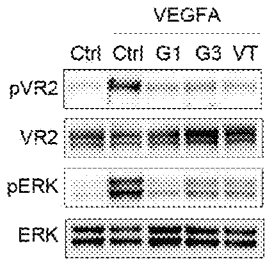
Figure 4B:
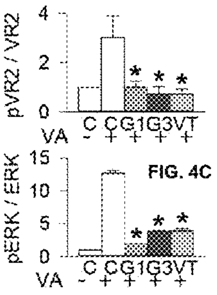
Figure 4D:
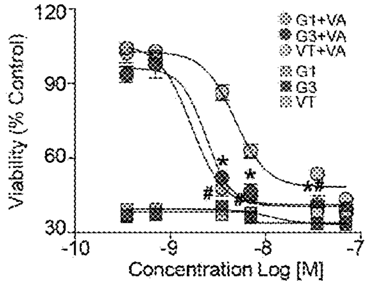
Figure 4E:
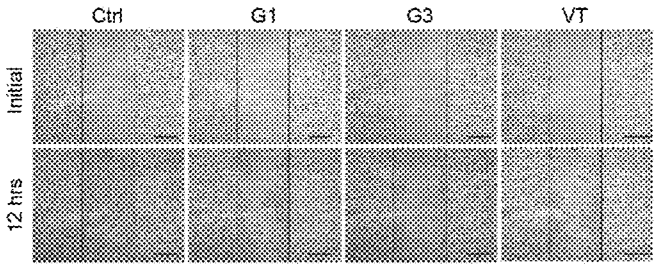
Figure 4F:
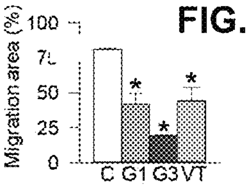
Figure 4G:
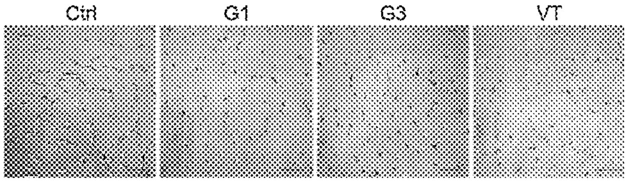
Figure 4H:
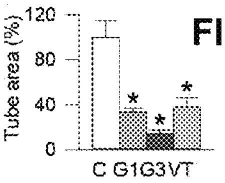
Figures 16A, 16B, 16C, 16D, 16E, 16F, 16G:
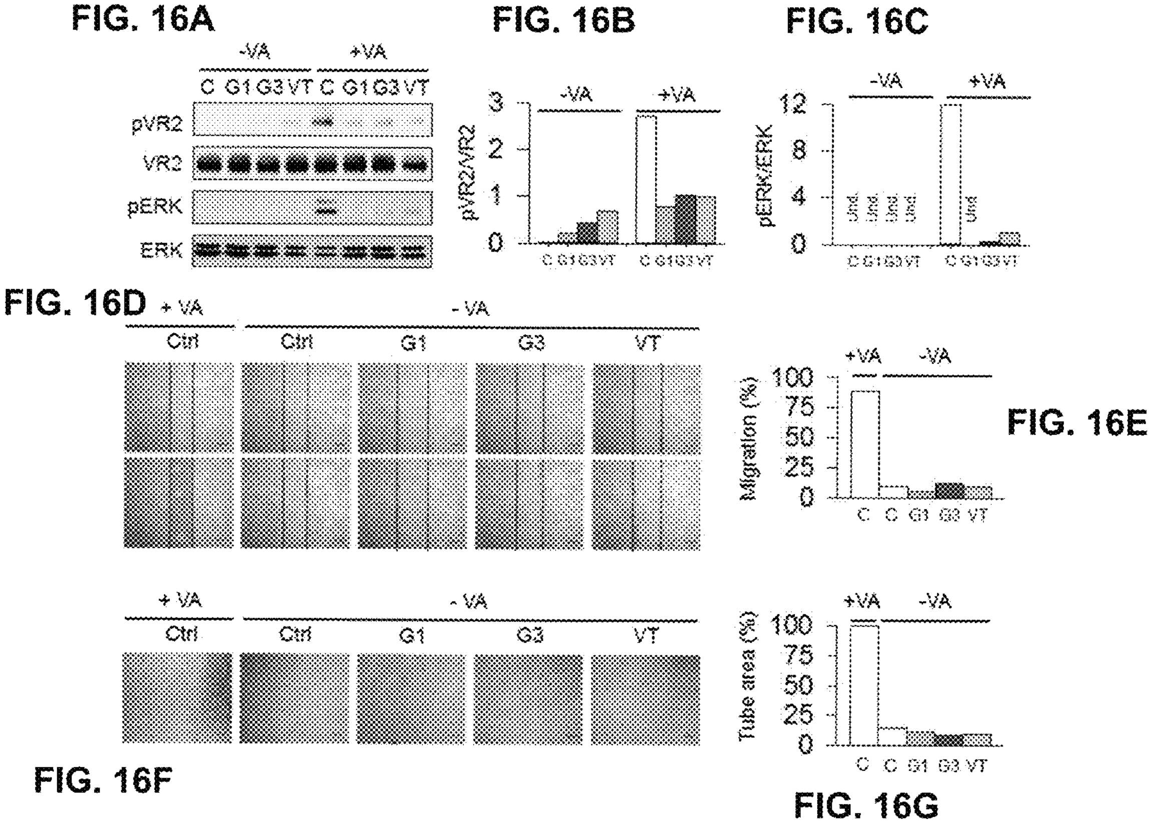
FIGS. 16A-16G show that VEGF-Grabs or VEGF-Trap have no effect on VEGFR2 signalling, EC survival, migration, and tube formation in the absence of VEGFA.

Example 2.4—VEGF-Grabs Inhibits EC Survival, Migration, and Tube Formation Via Suppression of the VEGF Signalling Pathway VEGF-A promotes proliferation, migration, and survival of endothelial cells through VEGFR2 activation. Accordingly, we examined VEGFR2 signalling in HUVECs. Both VEGF-Grabs and VT attenuated VEGF-A-induced phosphorylation of VEGFR2 and its downstream ERK (FIG. 4A-C, and FIG. 16A-C, see FIG. 17 for dose-dependent inhibitions). In addition, VEGF-Grabs inhibited VEGF-A- induced proliferation of HUVECs with a n $IC_{50}$ (half maximal inhibitory concentration) at 1.7 nM and 2.4 nM which are 2.8 and 2-fold more efficient than VT ($IC_{50}$=4.8 nM), respectively (FIG. 4D). Also, VEGF-Grabs and VT strongly suppressed VEGF-A-induced migration (FIGS. 4E and F, and FIGS. 16D and E) and tube formation (FIGS. 4G and H, and FIGS. 16F and G) of HUVECs. These results indicate that VEGF-Grabs and VT inhibit VEGF-A-induced endothelial cell activation at comparable levels, through VEGF-A sequestration.

Example 2.5—VEGF-Grab3 Displays Enhanced Anti-Tumor Activity

Figures 5A, 5B, 5C, 5D, 5E, 5F, 5G, 5H, 5I:
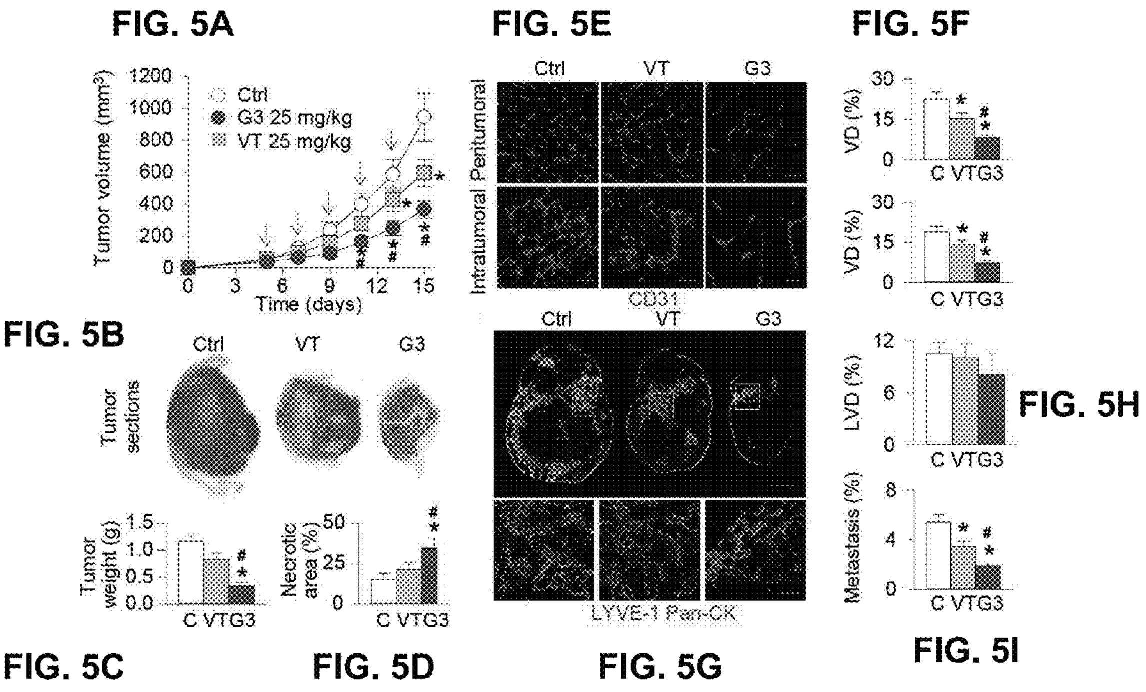

To evaluate the anti-tumor effects of G3, we employed the LLC tumor model and treated them with either VT or G3 at 25 mg/kg. G3 treatment resulted in 61% and 71% reduction in tumor volume and weight, while VT treatment showed 37% and 29% decreases, respectively (FIGS. 5A and C). In addition, intratumoral necrosis was more dramatic in G3-treated tumors (35%) than VT-treated tumors (21%) (FIGS. 5B and D). Furthermore, G3-treated tumors exhibited superior anti-angiogenic effects in both peri- and intratumoral regions and anti-metastatic effects compared with VT-treated tumors, even though there was no significant difference in the lymphatic vascular density (FIG. 5E-I).

Figure 18:
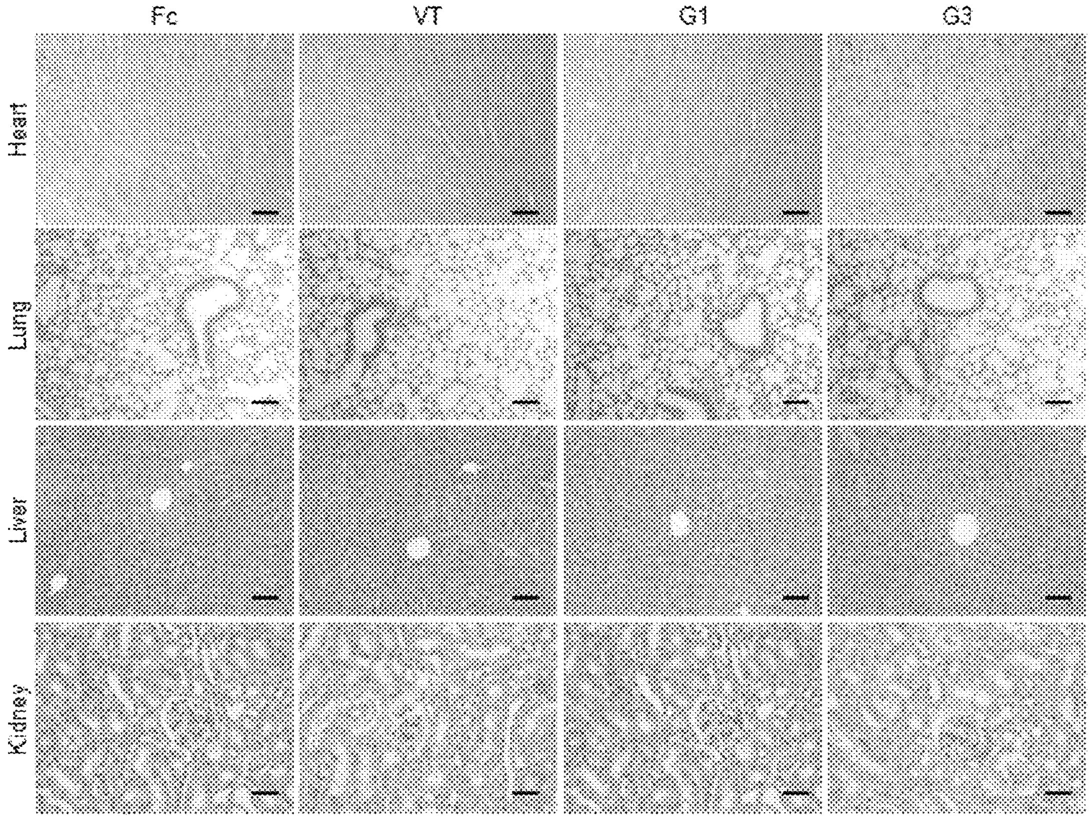
FIG. 18 shows histologic analyses of vital organs after anti-VEGF therapy. After a 2-week treatment with either control, VT, or VEGF-Grabs (25 mg/kg) in LLC tumor-bearing mice, indicated organs were sampled and sectioned for histologic analysis. Images show tissue sections of indicated organs stained with H&E. Scale bars, 100 μm.
Figure 19:
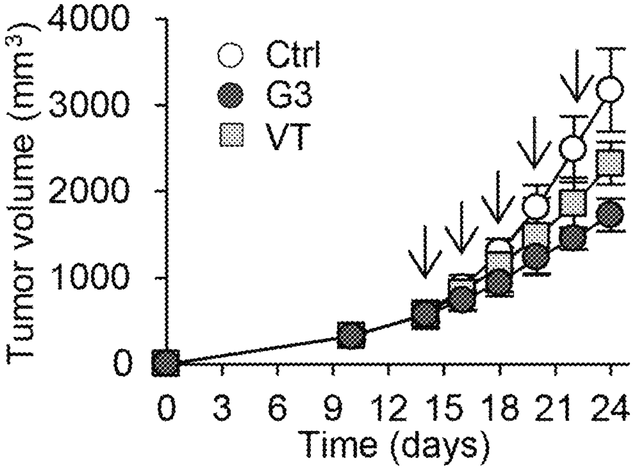
FIG. 19 shows that VEGF-Grab effectively suppresses the growth of established bulky macroscopic tumors. After the volume of tumor exceeded 500 $mm^3$, either control, VT, or G3 were treated to LLC tumor bearing mice on the indicated days (arrows). Comparison of LLC tumor growth.

Anti-VEGF therapy induces hypoxia which in turn stimulates the recruitment of TAM into intratumoral hypoxic region. TAM usually express profound pro-angiogenic and angiogenesis-modulating factors to re-vascularize the tumor. Interestingly, despite such a significant increase in hypoxia in both VT- and G3-treated tumors (FIGS. 5J and K), the level of macrophage infiltration in the G3-treated group remained nearly the same as that in non-treated control tumor (FIGS. 5L and M), which, we believe, is attributed to the increased affinity of G3 to PlGF compared with VT. We next compared the various gene expression profiles in tumors. G3 treatment down-regulated pro-angiogenic genes including VEGF-A, PlGF, VEGF-C, VEGFR1, and VEGFR2. G3 also reduced Bv8 and CCL2 expression compared with VT. These two genes are critical in myeloid cell recruitment to the tumor which can subsequently cause refractoriness to anti-angiogenic therapy (FIG. 5N). Furthermore, no obvious differences were observed in H&E stained sections of vital organs including heart, lung, liver, and kidney of VT- or G3-treated mice (FIG. 18). We also assessed the anti-tumor effect of G3 on established macroscopic tumors (>500 $mm^3$). These results showed 27% and 46% delays in tumor growth after VT and G3 treatment, respectively (FIG. 19), implying that G3 is a promising agent even against bulky macroscopic tumors.

Figures 20A, 20B:
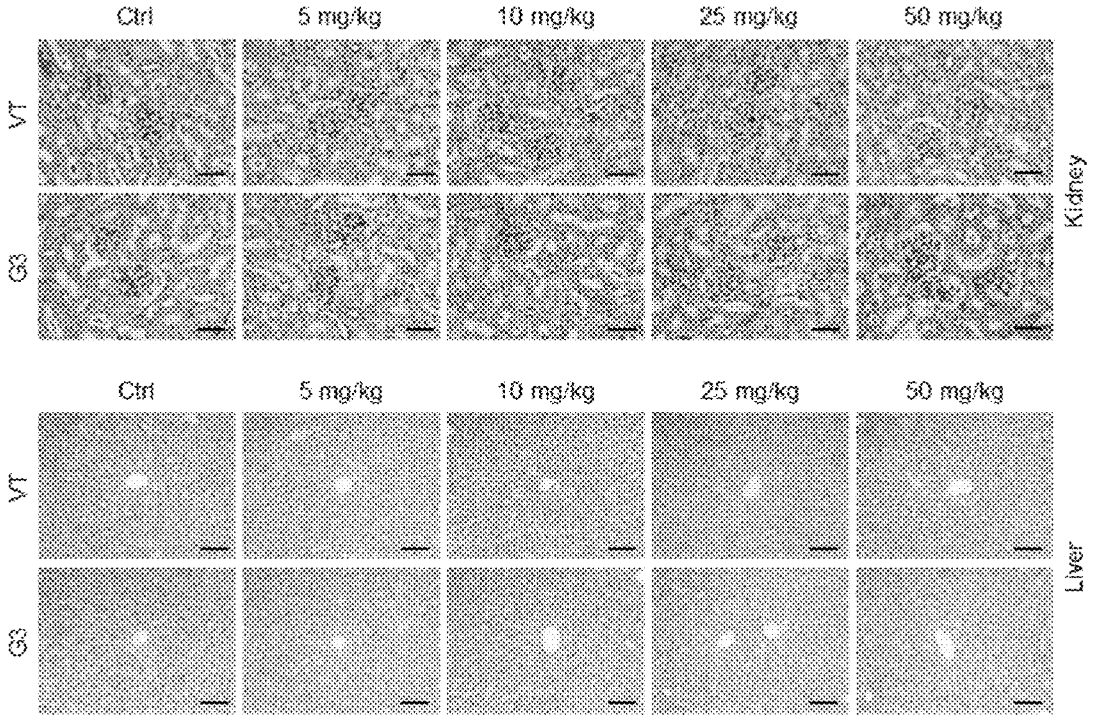
FIGS. 20A-20B show histological analyses of the kidney and liver after dose dependent anti-VEGF therapy. After treatment with either control, VT (5, 10, 25, and 50 mg/kg), or G3 (5, 10, 25, and 50 mg/kg) in LLC tumor-bearing mice, kidney and liver were sampled and sectioned for histologic analysis. Images show tissue sections of kidney (FIG. 20A) and liver (FIG. 20B) stained with H&E. Scale bars, 100 μm.

To confirm dose-responsiveness, tumor-bearing mice received injections of varying doses (5, 10, 25, and 50 mg/kg) of VT, or G3 every 2 days. The tumor growth of G3-treated group was gradually reduced in a dose-dependent manner with the maximal effect at 50 mg/kg. However, no distinct differences on tumor growth were observed between 25 mg/kg and 50 mg/kg in VT-treated group, whose efficiency, strikingly, was comparable to that of 10 mg/kg treatment of G3 (FIGS. 5O and P). In terms of tumor metastasis, VT and G3 both showed maximal anti-metastatic effects at 50 mg/kg (FIGS. 5Q and R). No significant changes were found in kidney or liver stained with H&E for any dosage of VT or G3 (FIG. 20). Taken together, these results suggest that the higher affinity to VEGF-A and PlGF and prolonged half-life of G3 contribute to its higher efficacy in cancer treatment over VT.

Figure 5S:
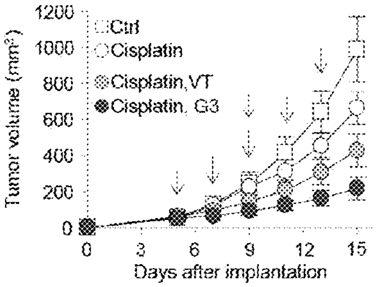
Figure 5T:
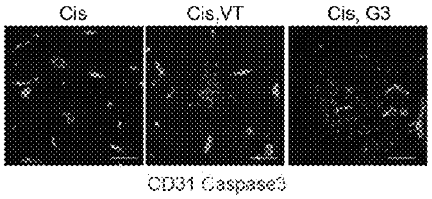
Figure 5U:
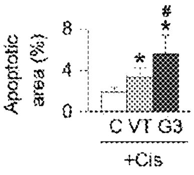
Figure 21:
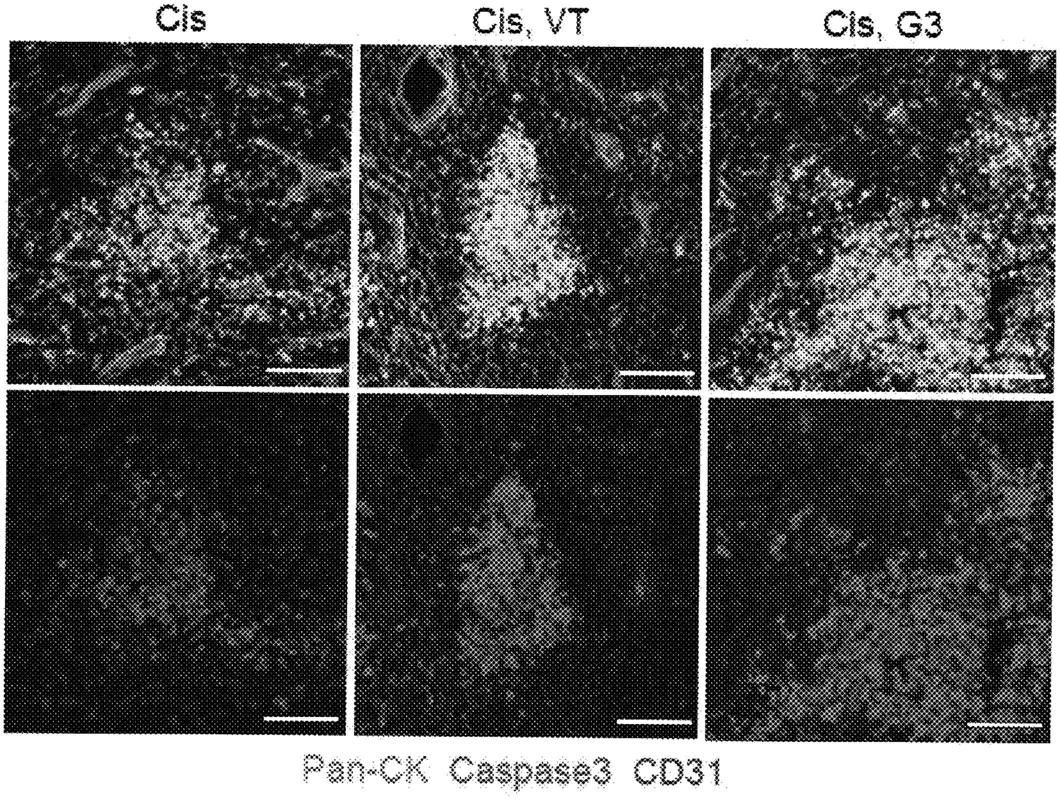
FIG. 21 shows that combination therapy of VEGF-Grab3 and Cisplatin enhances intratumoral apoptosis. LLC tumor-bearing mice received injections of cisplatin (10 mg/kg) 9 days after tumor implantation in combination with either control, VT, or G3 (25 mg/kg) every 2 days. After combination therapy, Caspase 3+ cells (Red) mostly overlap with Pan-cytokeratin+ cells (Green) which are epithelial cell derived LLC tumor, but not with CD31+ cells (Blue), suggesting apoptotic cells are more likely tumor cell.

Combining anti-VEGF therapy with chemotherapeutics is a valuable therapeutic strategy, as anti-VEGF therapy alone is not sufficient to induce complete regression of bulky tumors. The combined therapy of G3 and cisplatin displayed the most potent anti-tumor effect (78% reduction in tumor volume) in comparison to cisplatin monotherapy (33%) or combined therapy of VT and cisplatin (57%) (FIG. 5S). In addition, intratumoral apoptosis of tumor cells increased by >2-fold in the cisplatin+G3 combination group compared with cisplatin monotherapy (FIGS. 5T and U, FIG. 21). These results highlight G3 as a potent therapeutic option for combination chemotherapies.

Figures 6A, 6B, 6C, 6D:
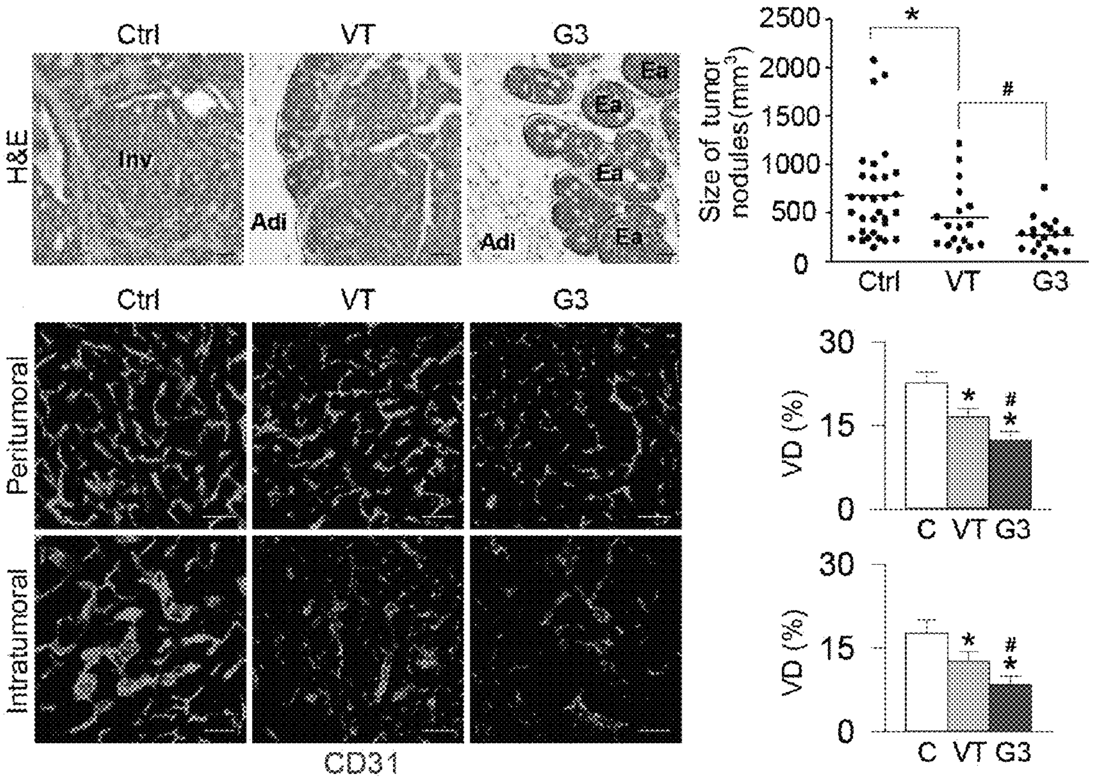

Example 2.6—VEGF-Grab3 Also Suppresses Tumor Growth, Angiogenesis, and Metastasis in a Spontaneous Breast Cancer Model To determine whether G3 consistently inhibits tumor progression in other tumor models, we confirmed our findings using a spontaneous breast cancer model-MMTV-PyMT mice. VT- and G3-treatment reduced the average size of tumor nodules by 34% and 61% compared to the control, respectively (FIG. 6B). Tumor sections stained with H&E showed that control MMTV-PyMT tumors displayed solid sheets of invasive tumor cells (Inv) with no remaining mammary gland structure. In contrast, in G3-treated tumor nodules, more early carcinoma lesions (Ea) were observed, in which the boundaries (dotted lines) between early carcinoma and surrounding adipose tissue (Adi) were well preserved (FIG. 6A). G3 reduced tumor vascular densities by 45% and 53% in peri- and intratumoral regions versus control, respectively, as compared to the 27% and 28% decreases observed in VT-treated tumors (FIGS. 6C and D). Tumor cell apoptosis was also significantly increased in G3-treated tumors compared to controls or VT-treated tumors (FIGS. 6E and F). The metastatic tumor cells were 64% and 52% less abundant in the axillary LNs of G3 and VT-treated mice, respectively, compared to the control, whereas we could not identify any significant differences in the lymphatic vascular density (FIG. 6G-I). These findings demonstrate that the increased anti-angiogenic activity of G3 effectively suppresses tumor growth and metastasis in a breast cancer model as well.

Example 2.7—VEGF-Grab3 Provides Durable Suppression of Tumor Angiogenesis

It has been reported that new vascular sprouts begin to regrow from remaining tumor vasculatures shortly after the cessation of anti-angiogenic therapy. To examine the durability of G3, we treated tumor-bearing mice with either VT, or G3 repeatedly at given time points (FIG. 7A, green arrows). We then withdrew treatment and analysed the remodelling of tumor vasculatures at D17 and D19 (FIG. 7A, blue arrows). While the control tumor vessels showed a 17% increase in tumor vascular density and a 24% increase in vascular sprouts between D17 (2 days off-treatment) and D19 (4 days off-treatment), VT-withdrawn tumor vessels at D19 showed 51% increase in vascular density and a 91% increase in vascular sprouts compared with D17, indicating a vigorous regrowth of tumor vessels upon cessation of conventional anti-VEGF treatment. In contrast to VT, G3-withdrawn tumor vessels showed only 20% and 22% increase in vascular density and vascular sprouts at D19 compared with D17, which are comparable to those of the control (FIG. 7B-D). These findings demonstrate a lasting suppressive effect of G3 on tumor angiogenesis compared to VT.

Figure 9A:
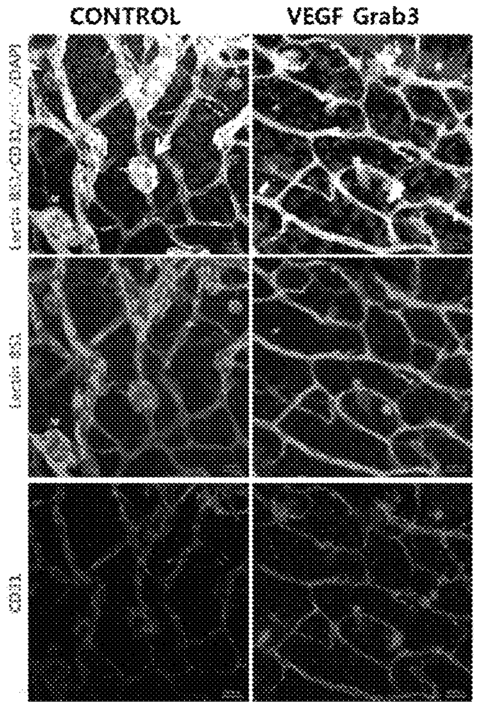
FIGS. 9A-9B show that intravitreal injection of VEGF-Grab3 reduced the vascular density of OIR model mice.
Figure 9B:
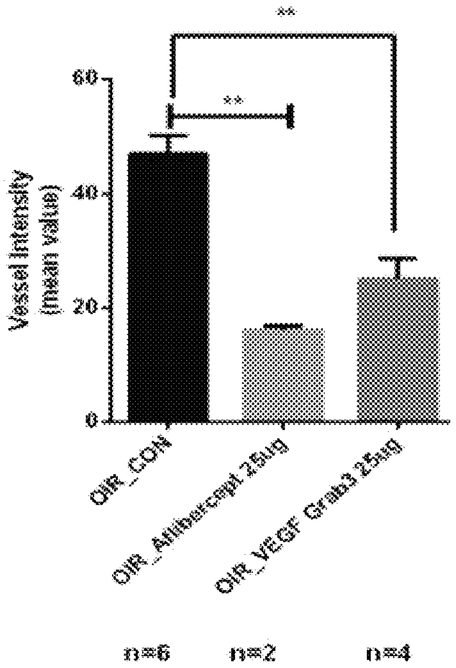

Example 2.8—Intravitreal Injection of VEGF-Grab3 Inhibits Choroidal Neovascularization and OIR Non-Perfusion Area Regression To determine whether G3 decreased CNV size, the area of CNV was measured by immunofluorescence confocal imaging 14 days after the induction of CNV. G3-treated mice demonstrated a significant regression in established CNV compared to PBS-treated control mice. The CNV size of PBS-treated control mice was 10803.34 $\mu m^3$ (range from 3017.24 $\mu m^3$ to 38898.73 $\mu m^3$, n=60) at 14 days after treatment. However, the CNV size of G3-treated mice significantly decreased to 5193.76 $\mu m^3$ (range from 270.52 $\mu m^3$ to 11563.26 $\mu m^3$, n=60) (P<0.01) (FIG. 8A). As shown in representative images of CNVs (FIG. 8B), CNVs size was significantly suppressed in the case of G3 treatment compared to PBS-treatment. Aflibercept-treated mice also demonstrated a significant CNV regression. CNV size was 5221.77 $\mu m^3$ (range from 439.68 $\mu m^3$ to 15984.70 $\mu m^3$, n=60) after Aflibercept treatment (P<0.01). Compared with the G3-treated mice, there was no significant difference in the CNV size of the Aflibercept-treated mice. The size of CNVs area among three groups and their statistical significances are shown in FIG. 8B. In the OIR mouse, treatment with VEGF-Grab increased the area of avascular retina at P17 compared with the PBS-injected control eyes. There was a near 2-fold increase in the vessel intensity of PBS injected eyes at P17 compared with the G3 treated eyes (P<0.01) (FIG. 9B). As shown in representative magnified images of retinal vasculature (FIG. 9A), vascular density was significantly suppressed in the case of G3 treatment compared to PBS-treatment. Our results demonstrate that one administration of G3 could inhibit laser-induced CNV and OIR Non-perfusion Area Regression effectively, highlighting G3 as a potential therapeutic option for AMD and DME.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

TABLE 1

VEGF-Grab Backbone

```
          10         20         30          40         50
60
          |          |          |           |          |
          |
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu
1_______________5__________hVEGFR1 SIGNAL SEQUENCE______15__________________20

          70         80          90         100        110
120
          |          |          |           |          |
          |
ACA GGA TCT AGT TCA GGT GAA TTC GGT AGA CCT TTC GTA GAG ATG TAC AGT GAA ATC CCC
TGT CCT AGA TCA AGT CCA CTT AAG CCA TCT GGA AAG CAT CTC TAC ATG TCA CTT TAG GGG
Thr Gly Ser Ser Ser Gly Glu Phe Gly Arg Pro Phe Val Glu Met Tyr Ser Glu Ile Pro
21______________25__26  27__________VEGFR1 DOMAIN 2_______35________________40

         130        140        150         160        170
180
          |          |          |           |          |
          |
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Tyr Glu Gly Arg Glu Leu Val Ile Pro Cys Arg Val Thr Ser Pro
41______________45__________________VEGFR1 DOMAIN 2_____55__________________60

         190        200        210         220        230
240
          |          |          |           |          |
          |
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val The Leu Lys Lys Phe Pro Leu Asp Thr Leu Ile Pro Asp Gly Lys Arg
61______________65 VEGFR1 DOMAIN 2______________________75__________________80

         250        260        270         280        290
         300
          |          |          |           |          |
          |
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
81______________85__________________VEGFR1 DOMAIN 2_____95__________________100

         310        320        330         340        350
```

TABLE 1-continued

VEGF-Grab Backbone

```
360
            |            |             |             |             |
           |
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
101_________VEGFR1 DOMAIN 2_________110_111 112_______VEGFR1 DOMAIN 3_______120

           370          380           390           400           410
420
            |            |             |             |             |
           |
CGA CAA ACC AAT ACA ATC ATA GAT GTC CAA ATA AGC ACA CCA CGC CCA GTC AAA TTA CTT
GCT GTT TGG TTA TGT TAG TAT CTA CAG GTT TAT TCG TGT GGT GCG GGT CAG TTT AAT GAA
Arg Gln Thr Asn Thr Ile Ile Asp Val Gln Ile Ser Thr Pro Arg Pro Val Lys Leu Leu
121_____________125_________________VEGFR1 DOMAIN 3_____135_________________140

           430          440           450           460           470
480
            |            |             |             |             |
           |
AGA GGC CAT ACT CTT GTC CTC AAT TGT ACT GCT ACC ACT CCC TTG AAC ACG AGA GTT CAA
TCT CCG GTA TGA GAA CAG GAG TTA ACA TGA CGA TGG TGA GGG AAC TTG TGC TCT CAA GTT
Arg Gly His Thr Leu Val Leu Asn Cys Thr Arg Thr Thr Pro Leu Asn Thr Arg Val Gln
141_____________145_________________VEGFR1 DOMAIN 3_____155_________________160

           490          500           510           520           530
540
            |            |             |             |             |
           |
ATG ACC TGG AGT TAC CCT GAT GAA AAA AAT AAG AGA GCT TCC GTA AGG CGA CGA ATT GAC
TAC TGG ACC TCA ATG GGA CTA CTT TTT TTA TTC TCT CGA AGG CAT TCC GCT GCT TAA CTG
Met Thr Trp Set Tyr Pro Asp Glu Lys Asn Lys Arg Ala Ser Val Arg Arg Arg Ile Asp
161_____________165_________________VEGFR1 DOMAIN 3_____175_________________180

           550          560           570           580           590
600
            |            |             |             |             |
           |
CAA AGC AAT TCC CAT GCC AAC ATA TTC TAC AGT GTT CTT ACT ATT GAC AAA ATG CAG AAC
GTT TCG TTA AGG GTA CGG TTG TAT AAG ATG TCA CAA GAA TGA TAA CTG TTT TAC GTC TTG
Gln Ser Asn Ser His Ala Asn Ile Phe Tyr Ser Val Leu Thr Ile Asp Lys Met Gln Asn
181_____________185_________________VEGFR1 DOMAIN 3_____195_________________200

           610          620           630           640           650
660
            |            |             |             |             |
           |
AAA GAC AAA GGA CTT TAT ACT TGT CGT GTA AGG AGT GGA CCA TCA TTC AAA TCT GTT AAC
TTT CTG TTT CCT GAA ATA TGA ACA GCA CAT TCC TCA CCT GGT AGT AAG TTT AGA CAA TTG
Lys Asp Lys Gly Leu Tyr Thr Cys Arg Val Arg Ser Gly Pro Ser Phe Lys Ser Val Asn
201_____________205_________________VEGFR1 DOMAIN 3_____215_________________220

           670          680           690           700           710
720
            |            |             |             |             |
           |
ACC TCA GTG CAT ATA TAT GAT AAA GCA CTC GAG GAC AAA ACT CAC ACA TGC CCA CCC TGC
TGG AGT CAC GTA TAT ATA CTA TTT CGT GAG CTC CTG TTT TGA GTG TGT ACG GGT GGC ACG
Thr Ser val His Ile Tyr Asp Lys Ala Leu Glu Asp Lys Thr His Thr Cys Pro Pro Cys
221_________VEGFR1 DOMAIN 3_____229 230_____________hFC DOMAIN______________240

           730          740           750           760           770
780
            |            |            |              |             |
           |
CCA GCA CCT GAA CTC CTG GGG GGA CCG TCA GTC TTC CTC TTC CCC CCA AAA CCC AAG GAC
GGT CGT GGA CTT GAG GAC CCC CCT GGC AGT CAG AAG GAG AAG GGG GGT TTT GGG TTC CTG
Pro Ala Pro Glu Leu Leu Gly Gly Pro Ser Val Phe Leu Phe Pro Pro Lys Pro Lys Asp
241_____________245_____________________hFC DOMAIN______255_________________260

           790          800           810           820           830
840
            |            |             |             |             |
           |
ACC CTC ATG ATC TCC CGG ACC CCT GAG GTC ACA TGC GTG GTG GTG GAC GTG AGC CAC GAA
TGG GAG TAC TAG AGG GCC TGG GGA CTC CAG TGT ACG CAC CAC CAC CTG CAC TCG GTG CTT
Thr Leu Met Ile Ser Arg Thr Pro Glu Val Thr Cys Val Val Val Asp Val Ser His Glu
```

TABLE 1-continued

VEGF-Grab Backbone

261____________265____________________hFC DOMAIN______275________________280

850 860 870 880 890
900

GAC CCT GAG GTC AAG TTC AAC TGG TAC GTG GAC GGC GTG GAG GTG CAT AAT GCC AAG ACA
CTG GGA CTC CAG TTC AAG TTG ACC ATG CAC CTG CCG CAC CTC CAC GTA TTA CGG TTC TGT
Asp Pro Glu Val Lys Phe Asn Trp Tyr Val Asp Gly Val Glu Val His Asn Ala Lys Thr
281____________285____________________hFC DOMAIN______295________________300

910 920 930 940 950
960

AAG CCG CGG GAG GAG CAG TAG AAC AGC ACG TAC CGT GTG GTC AGC GTC CTC ACC GTC CTG
TTC GGC GCC CTC CTC GTC ATG TTG TCG TGC ATG GCA CAC CAG TCG CAG GAG TGG CAG GAC
Lys Pro Arg Glu Glu Gln Tyr Asn Ser Thr Tyr Arg Val Val Ser Val Leu Thr Val Leu
301____________305____________________hFC DOMAIN______315________________320

970 980 990 1000 1010
1020

CAC CAG GAC TGG CTG AAT GGC AAG GAG TAC AAG TGC AAG GTC TCC AAC AAA GCC CTC CCA
GTG GTC CTG ACC GAC TTA CCG TTC CTC ATG TTC ACG TTC CAG AGG TTG TTT CGG GAG GGT
His Gln Asp Trp Leu Asn Gly Lys Glu Tyr Lys Cys Lys Val Ser Asn Lys Ala Leu Pro
321____________325_____________________hFC DOMAIN_____335________________340

1030 1040 1050 1060 1070
1080

GCC CCC ATC GAG AAA ACC ATC TCC AAA GCC AAA GGG CAG CCC CGA GAA CCA CAG GTG TAC
CGG GGG TAG CTC TTT TGG TAG AGG TTT CGG TTT CCC GTC GGG GCT CTT GGT GTC CAC ATG
Ala Pro Ile Glu Lys Thr Ile Ser Lys Ala Lys Gly Gln Pro Arg Glu Pro Gln Val Tyr
341____________345____________________hFC DOMAIN______355________________360

1090 1100 1110 1120 1130
1140

ACC CTG CCC CCA TCC CGG GAG GAG ATG ACC AAG AAC CAG GTC AGC CTG ACC TGC CTG GTC
TGG GAC GGG GGT AGG GCC CTC CTC TAC TGG TTC TTG GTC CAG TCG GAC TGG ACG GAC CAG
Thr Leu Pro Pro Ser Arg Glu Glu Met Thr Lys Asn Gln Val Ser Leu Thr Cys Leu Val
361____________365____________________hFC DOMAIN______375________________380

1150 1160 1170 1180 1190
1200

AAA GGC TTC TAT CCC AGC GAC ATC GCC GTG GAG TGG GAG AGC AAT GGG CAG CCG GAG AAC
TTT CCG AAG ATA GGG TCG CTG TAG CGG CAC CTC ACC CTC TCG TTA CCC GTC GGC CTC TTG
Lys Gly Phe Tyr Pro Ser Asp Ile Ala Val Glu Trp Glu Ser Asn Gly Gln Pro Glu Asn
381____________385____________________hFC DOMAIN______395________________400

1210 1220 1230 1240 1250
1260

AAC TAC AAG ACC ACG CCT CCC GTG CTG GAC TCC GAC GGC TCC TTC TTC CTC TAC AGC AAG
TTG ATG TTC TGG TGC GGA GGG CAC GAC CTG AGG CTG CCG AGG AAG AAG GAG ATG TCG TTC
Asn Tyr Lys Tyr Tyr Pro Pro Val Leu Asp Ser Asp Gly Ser Phe Phe Leu Tyr Ser Lys
401____________405____________________hFC DOMAIN______415________________420

1270 1280 1290 1300 1310
1320

CTC ACC GTG GAC AAG AGC AGG TGG CAG CAG GGG AAC GTC TTC TCA TGC TCC GTG ATG CAT
GAG TGG CAC CTG TTC TCG TCC ACC GTC GTC CCC TTG CAG AAG AGT ACG AGG CAC TAC GTA
Lys Thr Val Asp Lys Ser Arg Trp Gln Gln Gly Asn Val Phe Ser Cys Ser Val Met His
421____________425____________________hFC DOMAIN______435________________440

1330 1340 1350 1360 1370
1377

TABLE 1-continued

VEGF-Grab Backbone

```
GAG GCT CTG CAC AAC CAC TAC ACG CAG AAG AGC CTC TCC CTG TCT CCG GGT AAA TGA
(SEQ ID NO: 1)
CTC CGA GAC GTG TTG GTG ATG TGC GTC TTC TCG GAG AGG GAC AGA GGC CCA TTT ACT
Glu Ala Leu His Asn His Tyr Thr Gln Lys Ser Leu Ser Leu Ser Pro Gly Lys ***
(SEQ ID NO: 2)
441_____________445______________________hFC DOMAIN_____455_____________459
```

TABLE 2

VEGF-Grab1

```
              10             20             30              40              50
60
            |              |              |               |               |
|
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu
1_______________5__________hVEGFR1 SIGNAL SEQUENCE______15__________________20

            70             80             90              100             110
            120
            |              |              |               |               |
          |
ACA GGA TCT AGT TCA GGT GAA TTC GGT AGA CCT TTC GTA GAG ATG TAC AGT GAA ATC CCC
TGT CCT AGA TCA AGT CCA CTT AAG CCA TCT GGA AAG CAT CTC TAC ATG TCA CTT TAG GGG
Thr Gly Ser Ser Ser Gly Glu Phe Gly Arg Pro Phe Val Glu Met Tyr Ser Glu Ile Pro
21______________25__26 27___________VEGFR1 DOMAIN 2_______35_________________40

            130            140            150             160             170
            180
            |              |              |               |               |
          |
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Tyr Glu Gly Arg Glu Leu Val Ile Pro Cys Arg Val Thr Ser Pro
41______________45__________________VEGFR1 DOMAIN 2_____55___________________60

            190            200            210             220             230
            240
            |              |              |               |               |
          |
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val The Leu Lys Lys Phe Pro Leu Asp Thr Leu Ile Pro Asp Gly Lys Arg
61______________65__________________VEGFR1 DOMAIN 2_____75___________________80

            250            260            270             280             290
            300
            |              |              |               |               |
          |
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
81______________85__________________VEGFR1 DOMAIN 2_____95__________________100

            310            320            330             340             350
            360
            |              |              |               |               |
          |
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
101_________VEGFR1 DOMAIN 2__________110_111 112_______VEGFR1 DOMAIN 3______120

            370            380            390             400             410
            420
            |              |              |               |               |
          |
CGA CAA ACC AAT ACA ATC ATA GAT GTC CAA ATA AGC ACA CCA AGC CCA GTC ACA TTA CTT
GCT GTT TGG TTA TGT TAG TAT CTA CAG GTT TAT TCG TGT GGT TCG GGT CLG TGT AAT GAA
Arg Gln Thr Asn Thr Ile Ile Asp Val Gln Ile Ser Thr Pro Ser Pro Val Thr Leu Leu
121_____________125_________________VEGFR1 DOMAIN 3_____135_________________140

            430            440            450             460             470
```

TABLE 2-continued

VEGF-Grab1

```
         480
          |           |           |           |           |
         |
AGA GGC CAT ACT CTT GTC CTC AAT TGT ACT GCT ACC ACT CCC TTG AAC ACG AGA GTT CAA
TCT CCG GTA TGA GAA CAG GAG TTA ACA TGA CGA TGG TGA GGG AAC TTG TGC TCT CAA GTT
Arg Gly His Thr Leu Val Leu Asn Cys Thr Arg Thr Thr Pro Leu Asn Thr Arg Val Gln
141_____________145_________________VEGFR1 DOMAIN 3_____155_________________160

         490         500         510         520         530
         540
          |           |           |           |           |
         |
ATG ACC TGG AGT TAC CCT GAT GAA AAA AAT AAG AGA GCT TCC GTA AGG CGA CGA ATT GAC
TAC TGG ACC TCA ATG GGA CTA CTT TTT TTA TTC TCT CGA AGG CAT TCC GCT GCT TAA CTG
Met Thr Trp Ser Tyr Pro Asp Glu Lys Asn Lys Alg Ala Ser Val Arg Arg Arg Ile Asp
161_____________165_________________VEGFR1 DOMAIN 3_____175_________________180

         550         560         570         580         590
         600
          |           |           |           |           |
         |
CAA AGC AAT TCC CAT GCC AAC ATA TTC TAC AGT GTT CTT ACT ATT GAC AAA ATG CAG AAC
GTT TCG TTA AGG GTA CGG TTG TAT AAG ATG TCA CAA GAA TGA TAA CTG TTT TAC GTC TTG
Gln Ser Asn Ser His Ala Asn Ile Phe Tyr Ser Val Leu Thr Ile Asp Lys Met Gln Asn
181_____________185_________________VEGFR1 DOMAIN 3_____195_________________200

         610         620         630         640         650
         660
          |           |           |           |           |
         |
AAA GAC AAA GGA CTT TAT ACT TGT CGT GTA AGG AGT GGA CCA TCA TTC AAA TCT GTT AAC
TTT CTG TTT CCT GAA ATA TGA ACA GCA CAT TCC TCA CCT GGT AGT AAG TTT AGA CAA TTG
Lys Asp Lys Gly Leu Tyr Thr Cys Arg Val Arg Ser Gly Pro Ser Phe Lys Ser Val Asn
201_____________205_________________VEGFR1 DOMAIN 3_____215_________________220

         670         680         690         700         710
         720
          |           |           |           |           |
         |
ACC TCA GTG CAT ATA TAT GAT AAA GCA CTC GAG GAC AAA ACT CAC ACA TGC CCA CCG TGC
TGG AGT CAC GTA TAT ATA CTA TTT CGT GAG CTC CTG TTT TGA GTG TGT ACG GGT GGC ACG
Thr Ser Val His Ile Tyr Asp Lys Ala Leu Glu Asp Lys Thr His Thr Cys Pro Pro Cys
221_________VEGFR1 DOMAIN 3_____229 230_____________hFC DOMAIN______________240

         730         740         750         760         770
         780
          |           |           |           |           |
         |
CCA GCA CCT GAA CTC CTG GGG GGA CCG TCA GTC TTC CTC TTC CCC CCA AAA CCC AAG GAC
GGT CGT GGA CTT GAG GAC CCC CCT GGC AGT CAG AAG GAG AAG GGG GGT TTT GGG TTC CTG
Pro Ala Pro Glu Leu Leu Gly Gly Pro Ser Val Phe Leu Phe Pro Pro Lys Pro Lys Asp
241_____________245_____________________hFC DOMAIN______255_________________260

         790         800         810         820         830
         840
          |           |           |           |           |
         |
ACC CTC ATG ATC TCC CGG ACC CCT GAG GTC ACA TGC GTG GTG GTG GAC GTG AGC CAC GAA
TGG GAG TAC TAG AGG GCC TGG GGA CTC CAG TGT ACG CAC CAC CAC CTG CAC TCG GTG CTT
Thr Leu Met Ile Ser Arg Thr Pro Glu Val Thr Cys Val Val Val Asp Val Ser His Glu
261_____________265_____________________hFC DOMAIN______275_________________280

         850         860         870         880         890
         900
          |           |           |           |           |
         |
GAC CCT GAG GTC AAG TTC AAC TGG TAC GTG GAC GGC GTG GAG GTG CAT AAT GCC AAG ACA
CTG GGA CTC CAG TTC AAG TTG ACC ATG CAC CTG CCG CAC CTC CAC GTA TTA CGG TTC TGT
Asp Pro Glu Val Lys Phe Asn Trp Tyr Val Asp Gly Val Glu Val His Asn Ala Lys Thr
281_____________285_____________________hFC DOMAIN______295_________________300

         910         920         930         940         950
         960
          |           |           |           |           |
         |
AAG CCG CGG GAG GAG CAG TAC AAC AGC ACG TAC CGT GTG GTC AGC GTC CTC ACC GTC CTG
TTC GGC GCC CTC CTC GTC ATG TTG TCG TGC ATG GCA CAC CAG TCG CAG GAG TGG CAG GAC
Lys Pro Arg Glu Glu Gln Tyr Asn Ser Thr Tyr Arg Val Val Ser Val Leu Thr Val Leu
```

TABLE 2-continued

VEGF-Grab1

```
301____________305____________________hFC DOMAIN_____315________________320

           970          980            990            1000           1010
           1020
           |             |              |              |              |
         |
CAC CAG GAC TGG CTG AAT GGC AAG GAG TAC AAG TGC AAG GTC TCC AAC AAA GCC CTC CCA
GTG GTC CTG ACC GAC TTA CCG TTC CTC ATG TTC ACG TTC CAG AGG TTG TTT CGG GAG GGT
His Gln Asp Trp Leu Asn Gly Lys Glu Tyr Lys Cys Lys Val Ser Asn Lys Ala Leu Pro
321____________25_____________________hFC DOMAIN_____335________________340

          1030          1040          1050            1060           1070
          1080
           |             |              |              |              |
         |
GCC CCC ATC GAG AAA ACC ATC TCC AAA GCC AAA GGG CAG CCC CGA GAA CCA CAG GTG TAC
CGG GGG TAG CTC TTT TGG TAG AGG TTT CGG TTT CCC GTC GGG GCT CTT GGT GTC CAC ATG
Ala Pro Ile Glu Lys Thr Ile Ser Lys Ala Lys Gly Gln Pro Arg Glu Pro Gln Val Tyr
341____________345____________________hFC DOMAIN_____355________________360

           1090         1100          1110            1120           1130
           1140
           |             |              |              |              |
         |
ACC CTG CCC CCA TCC CGG GAG GAG ATG ACC AAG AAC CAG GTC AGC CTG ACC TGC CTG GTC
TGG GAC GGG GGT AGG GCC CTC CTC TAC TGG TTC TTG GTC CAG TCG GAC TGG ACG GAC CAG
Thr Leu Pro Pro Ser Arg Glu Glu Met Thr Lys Asn Gln Val Ser Leu Thr Cys Leu Val
361 ___________365____________________hFC DOMAIN_____375________________380

           1150         1160          1170            1180           1190
           1200
           |             |              |              |              |
         |
AAA GGC TTC TAT CCC AGC GAC ATC GCC GTG GAG TGG GAG AGC AAT GGG CAG CCG GAG AAC
TTT CCG AAG ATA GGG TCG CTG TAG CGG CAC CTC ACC CTC TCG TTA CCC GTC GGC CTC TTG
Lys Gly Phe Tyr Pro Ser Asp Ile Ala Val Glu Trp Glu Ser Asn Gly Gln Pro Glu Asn
381____________385____________________hFC DOMAIN_____395________________400

           1210         1220          1230            1240           1250
           1260
           |             |              |              |              |
         |
AAC TAC AAG ACC ACG CCT CCC GTG CTG GAC TCC GAC GGC TCC TTC TTC CTC TAC AGC AAG
TTG ATG TTC TGG TGC GGA GGG CAC GAC CTG AGG CTG CCG AGG AAG AAG GAG ATG TCG TTC
Asn Tyr Lys Tyr Tyr Pro Pro Val Leu Asp Ser Asp Gly Ser Phe Phe Leu Tyr Ser Lys
401____________405____________________hFC DOMAIN_____415________________420

           1270         1280          1290            1300           1310
           1320
           |             |              |              |              |
         |
CTC ACC GTG GAC AAG AGC AGG TGG CAG CAG GGG AAC GTC TTC TCA TGC TCC GTG ATG CAT
GAG TGG CAC CTG TTC TCG TCC ACC GTC GTC CCC TTG CAG AAG AGT ACG AGG CAC TAC GTA
Lys Thr Val Asp Lys Ser Arg Trp Gln Gln Gly Asn Val Phe Ser Cys Ser Val Met His
421____________425____________________hFC DOMAIN_____435________________440

           1330         1340          1350            1360      1370
           1377
           |             |              |              |         |
         |
GAG GCT CTG CAC AAC CAC TAC ACG CAG AAG AGC CTC TCC CTG TCT CCG GGT AAA TGA
(SEQ ID NO: 3)
CTC CGA GAC GTG TTG GTG ATG TGC GTC TTC TCG GAG AGG GAC AGA GGC CCA TTT ACT
Glu Ala Leu His Asn His Tyr Thr Gln Lys Ser Leu Ser Leu Ser Pro Gly Lys ***
(SEQ ID NO: 4)
441____________445____________________hFC DOMAIN_____455____________459
```

TABLE 3

VEGF-Grab2

```
           10           20             30              40             50
           60
           |             |              |              |              |
         |
ATG GTC AGC TAC TGG GAC ACC GGG GTC CTG CTG TGC GCG CTG CTC AGC TGT CTG CTT CTC
```

TABLE 3-continued

VEGF-Grab2

```
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu
1_______________5__________hVEGFR1 SIGNAL SEQUENCE______15_________________20

            70             80              90             100            110
            120
            |              |               |               |               |
          |
ACA GGA TCT AGT TCA GGT GAA TTC GGT AGA CCT TTC GTA GAG ATG TAC AGT GAA ATC CCC
TGT CCT AGA TCA AGT CCA CTT AAG CCA TCT GGA AAG CAT CTC TAC ATG TCA CTT TAG GGG
Thr Gly Ser Ser Ser Gly Glu Phe Gly Arg Pro Phe Val Glu Met Tyr Ser Glu Ile Pro
21______________25__26 27___________VEGFR1 DOMAIN 2_______35________________40

            130            140             150            160            170
            180
            |              |               |               |               |
          |
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Tyr Glu Gly Arg Glu Leu Val Ile Pro Cys Arg Val Thr Ser Pro
41______________4___________________VEGFR1 DOMAIN 2_____55__________________60

            190            200             210            220             230
            240
            |              |               |               |               |
          |
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val The Leu Lys Lys Phe Pro Leu Asp Thr Leu Ile Pro Asp Gly Lys Arg
61______________65__________________VEGFR1 DOMAIN 2_____75__________________80

            250            260             270            280            290
            300
            |              |               |               |               |
          |
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
81______________85__________________VEGFR1 DOMAIN 2_____95__________________100

            310            320             330            340            350
            360
            |              |               |               |               |
          |
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
101_________VEGFR1 DOMAIN 2_________110_111 112_______VEGFR1 DOMAIN 3_______120

            370            380             390            400            410
            420
            |              |               |               |               |
          |
CGA CAA ACC AAT ACA ATC ATA GAT GTC CAA ATA AGC ACA CCA CGC CCA GTC AAA TTA CTT
GCT GTT TGG TTA TGT TAG TAT CTA CAG GTT TAT TCG TGT GGT GCG GGT CAG TTT AAT GAA
Arg Gln Thr Asn Thr Ile Ile Asp Val Gln Ile Ser Thr Pro Arg Pro Val Lys Leu Leu
121_____________125_________________VEGFR1 DOMAIN 3_____135_________________140

            430            440             450            460            470
            480
            |              |               |               |               |
          |
AGA GGC CAT ACT CTT GTC CTC AAT TGT ACT GCT ACC ACT CCC TTG AAC ACG AGA GTT CAA
TCT CCG GTA TGA GAA CAG GAG TTA ACA TGA CGA TGG TGA GGG AAC TTG TGC TCT CAA GTT
Arg Gly His Thr Leu Val Leu Asn Cys Thr Arg Thr Thr Pro Leu Asn Thr Arg Val Gln
141_____________145_________________VEGFR1 DOMAIN 3_____155_________________160

            490             500             510             520            530
            540
            |              |               |               |               |
          |
ATG ACC TGG AGT TAC CCT GAT GAA AAA AAT AAG AAC GCT TCC GTA AGG CGA CGA ATT GAC
TAC TGG ACC TCA ATG GGA CTA CTT TTT TTA TTC TTG CGA AGG CAT TCC GCT GCT TAA CTG
Met Thr Trp Ser Tyr Pro Asp Glu Lys Asn Lys Asn Ala Ser Val Arg Arg Arg Ile Asp
161_____________165_________________VEGFR1 DOMAIN 3_____175_________________180

            550            560             570            580            590
            600
```

TABLE 3-continued

VEGF-Grab2

```
CAA AGC AAT TCC CAT GCC AAC ATA TTC TAC AGT GTT CTT ACT ATT GAC AAA ATG CAG AAC
GTT TCG TTA AGG GTA CGG TTG TAT AAG ATG TCA CAA GAA TGA TAA CTG TTT TAC GTC TTG
Gln Ser Asn Ser His Ala Asn Ile Phe Tyr Ser Val Leu Thr Ile Asp Lys Met Gln Asn
181____________185________________VEGFR1 DOMAIN 3_____195________________200

            610          620            630            640           650
            660
AAA GAC AAA GGA CTT TAT ACT TGT CGT GTA AGG AGT GGA CCA TCA TTC AAA TCT GTT AAC
TTT CTG TTT CCT GAA ATA TGA ACA GCA CAT TCC TCA CCT GGT AGT AAG TTT AGA CAA TTG
Lys Asp Lys Gly Leu Tyr Thr Cys Arg Val Arg Ser Gly Pro Ser Phe Lys Ser Val Asn
201____________205________________VEGFR1 DOMAIN 3_____215________________220

            670          680            690            700           710
            720
ACC TCA GTG CAT ATA TAT GAT AAA GCA CTC GAG GAC AAA ACT CAC ACA TGC CCA CCG TGC
TGG AGT CAC GTA TAT ATA CTA TTT CGT GAG CTC CTG TTT TGA GTG TGT ACG GGT GGC ACG
Thr Ser Val His Ile Tyr Asp Lys Ala Leu Glu Asp Lys Thr His Thr Cys Pro Pro Cys
221_________VEGFR1 DOMAIN 3_____229 230____________hFC DOMAIN_____________240

            730          740            750            760           770
            780
CCA GCA CCT GAA CTC CTG GGG GGA CCG TCA GTC TTC CTC TTC CCC CCA AAA CCC AAG GAC
GGT CGT GGA CTT GAG GAC CCC CCT GGC AGT CAG AAG GAG AAG GGG GGT TTT GGG TTC CTG
Pro Ala Pro Glu Leu Leu Gly Gly Pro Ser Val Phe Leu Phe Pro Pro Lys Pro Lys Asp
241____________245____________________hFC DOMAIN______255________________260

            790          800            810            820           830
            840
ACC CTC ATG ATC TCC CGG ACC CCT GAG GTC ACA TGC GTG GTG GTG GAC GTG AGC CAC GAA
TGG GAG TAC TAG AGG GCC TGG GGA CTC CAG TGT ACG CAC CAC CAC CTG CAC TCG GTG CTT
Thr Leu Met Ile Ser Arg Thr Pro Glu Val Thr Cys Val Val Val Asp Val Ser His Glu
261____________265____________________hFC DOMAIN______275________________280

            850          860            870            880           890
            900
GAC CCT GAG GTC AAG TTC AAC TGG TAC GTG GAC GGC GTG GAG GTG CAT AAT GCC AAG ACA
CTG GGA CTC CAG TTC AAG TTG ACC ATG CAC CTG CCG CAC CTC CAC GTA TTA CGG TTC TGT
Asp Pro Glu Val Lys Phe Asn Trp Tyr Val Asp Gly Val Glu Val His Asn Ala Lys Thr
281____________285____________________hFC DOMAIN______295________________300

            910          920            930            940           950
            960
AAG CCG CGG GAG GAG CAG TAC AAC AGC ACG TAC CGT GTG GTC AGC GTC CTC ACC GTC CTG
TTC GGC GCC CTC CTC GTC ATG TTG TCG TGC ATG GCA CAC CAG TCG CAG GAG TGG CAG GAC
Lys Pro Arg Glu Glu Gln Tyr Asn Ser Thr Tyr Arg Val Val Ser Val Leu Thr Val Leu
301____________305____________________hFC DOMAIN______315________________320

            970          980            990            1000          1010
            1020
CAC CAG GAC TGG CTG AAT GGC AAG GAG TAC AAG TGC AAG GTC TCC AAC AAA GCC CTC CCA
GTG GTC CTG ACC GAC TTA CCG TTC CTC ATG TTC ACG TTC CAG AGG TTG TTT CGG GAG GGT
His Gln Asp Trp Leu Asn Gly Lys Glu Tyr Lys Cys Lys Val Ser Asn Lys Ala Leu Pro
321____________325____________________hFC DOMAIN______335________________340

            1030        1040            1050           1060          1070
            1080
GCC CCC ATC GAG AAA ACC ATC TCC AAA GCC AAA GGG CAG CCC CGA GAA CCA CAG GTG TAC
CGG GGG TAG CTC TTT TGG TAG AGG TTT CGG TTT CCC GTC GGG GCT CTT GGT GTC CAC ATG
Ala Pro Ile Glu Lys Thr Ile Ser Lys Ala Lys Gly Gln Pro Arg Glu Pro Gln Val Tyr
341____________345____________________hFC DOMAIN______355________________360
```

TABLE 3-continued

VEGF-Grab2

```
           1090        1100            1110            1120           1130
           1140
            |              |               |               |               |
          |
ACC CTG CCC CCA TCC CGG GAG GAG ATG ACC AAG AAC CAG GTC AGC CTG ACC TGC CTG GTC
TGG GAC GGG GGT AGG GCC CTC CTC TAC TGG TTC TTG GTC CAG TCG GAC TGG ACG GAC CAG
Thr Leu Pro Pro Ser Arg Glu Glu Met Thr Lys Asn Gln Val Ser Leu Thr Cys Leu Val
361____________365_____________________hFC DOMAIN______375_________________380

           1150        1160            1170            1180           1190
           1200
            |              |               |               |               |
          |
AAA GGC TTC TAT CCC AGC GAC ATC GCC GTG GAG TGG GAG AGC AAT GGG CAG CCG GAG AAC
TTT CCG AAG ATA GGG TCG CTG TAG CGG CAC CTC ACC CTC TCG TTA CCC GTC GGC CTC TTG
Lys Gly Phe Tyr Pro Ser Asp Ile Ala Val Glu Trp Glu Ser Asn Gly Gln Pro Glu Asn
381____________385_____________________hFC DOMAIN______395_________________400

           1210        1220            1230            1240           1250
           1260
            |              |               |               |               |
          |
AAC TAC AAG ACC ACG CCT CCC GTG CTG GAC TCC GAC GGC TCC TTC TTC CTC TAC AGC AAG
TTG ATG TTC TGG TGC GGA GGG CAC GAC CTG AGG CTG CCG AGG AAG AAG GAG ATG TCG TTC
Asn Tyr Lys Tyr Tyr Pro Pro Val Leu Asp Ser Asp Gly Ser Phe Phe Leu Tyr Ser Lys
401____________405_____________________hFC DOMAIN______415_________________420

           1270        1280            1290           1300             1310
           1320
            |              |               |               |               |
          |
CTC ACC GTG GAC AAG AGC AGG TGG CAG CAG GGG AAC GTC TTC TCA TGC TCC GTG ATG CAT
GAG TGG CAC CTG TTC TCG TCC ACC GTC GTC CCC TTG CAG AAG AGT ACG AGG CAC TAC GTA
Lys Thr Val Asp Lys Ser Arg Trp Gln Gln Gly Asn Val Phe Ser Cys Ser Val Met His
421____________425_____________________hFC DOMAIN______435_________________440

           1330        1340            1350            1360           1370
           1377
            |              |               |               |               |
          |
GAG GCT CTG CAC AAC CAC TAC ACG CAG AAG AGC CTC TCC CTG TCT CCG GGT AAA TGA
(SEQ ID NO: 5)
CTC CGA GAC GTG TTG GTG ATG TGC GTC TTC TCG GAG AGG GAC AGA GGC CCA TTT ACT
Glu Ala Leu His Asn His Tyr Thr Gln Lys Ser Leu Ser Leu Ser Pro Gly Lys ***
(SEQ ID NO: 6)
441____________445_____________________hFC DOMAIN______455_____________459
```

VEGF-Grab3

```
           10             20              30              40             50
           60
            |              |               |               |               |
          |
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu
1_______________5__________hVEGFR1 SIGNAL SEQUENCE______15__________________20

           70             80              90             100            110
           120
            |              |               |               |               |
          |
ACA GGA TCT AGT TCA GGT GAA TTC GGT AGA CCT TTC GTA GAG ATG TAC AGT GAA ATC CCC
TGT CCT AGA TCA AGT CCA CTT AAG CCA TCT GGA AAG CAT CTC TAC ATG TCA CTT TAG GGG
Thr Gly Ser Ser Ser Gly Glu Phe Gly Arg Pro Phe Val Glu Met Tyr Ser Glu Ile Pro
21_____________25__26 27___________VEGFR1 DOMAIN 2_______35________________40

           130             140             150             160            170
           180
            |              |               |               |               |
          |
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
```

-continued

VEGF-Grab3

```
Glu Ile Ile His Met Tyr Glu Gly Arg Glu Leu Val Ile Pro Cys Arg Val Thr Ser Pro
41_____________45_________________VEGFR1 DOMAIN 2_____55_________________60

            190          200             210             220            230
            240
             |             |               |               |               |
          |
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val The Leu Lys Lys Phe Pro Leu Asp Thr Leu Ile Pro Asp Gly Lys Arg
61_____________65_________________VEGFR1 DOMAIN 2_____75_________________80

            250          260             270             280            290
            300
             |             |               |               |               |
          |
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
81_____________85_________________VEGFR1 DOMAIN 2_____95_________________100

            310          320             330             340            350
            360
             |             |               |               |               |
          |
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
101_________VEGFR1 DOMAIN 2_________110_111 112_______VEGFR1 DOMAIN 3_______120

            370          380             390             400            410
            420
             |             |               |               |               |
          |
CGA CAA ACC AAT ACA ATC ATA GAT GTC CAA ATA AGC ACA CCA AGC CCA GTC ACA TTA CTT
GCT GTT TGG TTA TGT TAG TAT CTA CAG GTT TAT TCG TGT GGT TCG GGT CAG TGT AAT GAA
Arg Gln Thr Asn Thr Ile Ile Asp Val Gln Ile Ser Thr Pro Ser Pro Val Thr Leu Leu
121____________125________________VEGFR1 DOMAIN 3_____135________________140

            430          440             450             460            470
            480
             |             |               |               |               |
          |
AGA GGC CAT ACT CTT GTC CTC AAT TGT ACT GCT ACC ACT CCC TTG AAC ACG AGA GTT CAA
TCT CCG GTA TGA GAA CAG GAG TTA ACA TGA CGA TGG TGA GGG AAC TTG TGC TCT CAA GTT
Arg Gly His Thr Leu Val Leu Asn Cys Thr Arg Thr Thr Pro Leu Asn Thr Arg Val Gln
141____________145________________VEGFR1 DOMAIN 3_____155________________160

            490          500             510             520            530
            540
             |             |               |               |               |
          |
ATG ACC TGG AGT TAC CCT GAT GAA AAA AAT AAG AAC GCT TCC GTA AGG CGA CGA ATT GAC
TAC TGG ACC TCA ATG GGA CTA CTT TTT TTA TTC TTG CGA AGG CAT TCC GCT GCT TAA CTG
Met Thr Trp Ser Tyr Pro Asp Glu Lys Asn Lys Asn Ala Ser Val Arg Arg Arg Ile Asp
161____________165________________VEGFR1 DOMAIN 3_____175________________180

            550          560             570             580            590
            600
             |             |               |               |               |
          |
CAA AGC AAT TCC CAT GCC AAC ATA TTC TAC AGT GTT CTT ACT ATT GAC AAA ATG CAG AAC
GTT TCG TTA AGG GTA CGG TTG TAT AAG ATG TCA CAA GAA TGA TAA CTG TTT TAC GTC TTG
Gln Ser Asn Ser His Ala Asn Ile Phe Tyr Ser Val Leu Thr Ile Asp Lys Met Gln Asn
181____________185________________VEGFR1 DOMAIN 3_____195________________200

            610          620             630             640            650
            660
             |             |               |               |               |
          |
AAA GAC AAA GGA CTT TAT ACT TGT CGT GTA AGG AGT GGA CCA TCA TTC AAA TCT GTT AAC
TTT CTG TTT CCT GAA ATA TGA ACA GCA CAT TCC TCA CCT GGT AGT AAG TTT AGA CAA TTG
Lys Asp Lys Gly Leu Tyr Thr Cys Arg Val Arg Ser Gly Pro Ser Phe Lys Ser Val Asn
201____________205________________VEGFR1 DOMAIN 3_____215________________220

            670          680             690             700            710
            720
```

-continued

```
                              VEGF-Grab3

            |              |               |               |               |
          |
ACC TCA GTG CAT ATA TAT GAT AAA GCA CTC GAG GAC AAA ACT CAC ACA TGC CCA CCG TGC
TGG AGT CAC GTA TAT ATA CTA TTT CGT GAG CTC CTG TTT TGA GTG TGT ACG GGT GGC ACG
Thr Ser Val His Ile Tyr Asp Lys Ala Leu Glu Asp Lys Thr His Thr Cys Pro Pro Cys
221________VEGFR1 DOMAIN 3_____229 230____________hFC DOMAIN_____________240

            730          740             750             760            770
            780
            |              |               |               |               |
          |
CCA GCA CCT GAA CTC CTG GGG GGA CCG TCA GTC TTC CTC TTC CCC CCA AAA CCC AAG GAC
GGT CGT GGA CTT GAG GAC CCC CCT GGC AGT CAG AAG GAG AAG GGG GGT TTT GGG TTC CTG
Pro Ala Pro Glu Leu Leu Gly Gly Pro Ser Val Phe Leu Phe Pro Pro Lys Pro Lys Asp
241____________245____________________hFC DOMAIN_____255________________260

            790          800             810             820            830
            840
            |              |               |               |               |
          |
ACC CTC ATG ATC TCC CGG ACC CCT GAG GTC ACA TGC GTG GTG GTG GAC GTG AGC CAC GAA
TGG GAG TAC TAG AGG GCC TGG GGA CTC CAG TGT ACG CAC CAC CAC CTG CAC TCG GTG CTT
Thr Leu Met Ile Ser Arg Thr Pro Glu Val Thr Cys Val Val Val Asp Val Ser His Glu
261____________265____________________hFC DOMAIN_____275________________280

            850          860             870             880            890
            900
            |              |               |               |               |
          |
GAC CCT GAG GTC AAG TTC AAC TGG TAC GTG GAC GGC GTG GAG GTG CAT AAT GCC AAG ACA
CTG GGA CTC CAG TTC AAG TTG ACC ATG CAC CTG CCG CAC CTC CAC GTA TTA CGG TTC TGT
Asp Pro Glu Val Lys Phe Asn Trp Tyr Val Asp Gly Val Glu Val His Asn Ala Lys Thr
281____________285____________________hFC DOMAIN_____295________________300

            910          920             930             940             950
            960
            |              |               |               |               |
          |
AAG CCG CGG GAG GAG CAG TAC AAC AGC ACG TAC CGT GTG GTC AGC GTC CTC ACC GTC CTG
TTC GGC GCC CTC CTC GTC ATG TTG TCG TGC ATG GCA CAC CAG TCG CAG GAG TGG CAG GAC
Lys Pro Arg Glu Glu Gln Tyr Asn Ser Thr Tyr Arg Val Val Ser Val Leu Thr Val Leu
301____________305____________________hFC DOMAIN_____315________________320

            970          980             990             1000           1010
            1020
            |              |               |               |               |
          |
CAC CAG GAC TGG CTG AAT GGC AAG GAG TAC AAG TGC AAG GTC TCC AAC AAA GCC CTC CCA
GTG GTC CTG ACC GAC TTA CCG TTC CTC ATG TTC ACG TTC CAG AGG TTG TTT CGG GAG GGT
His Gln Asp Trp Leu Asn Gly Lys Glu Tyr Lys Cys Lys Val Ser Asn Lys Ala Leu Pro
321____________325____________________hFC DOMAIN_____335________________340

            1030        1040            1050            1060           1070
            1080
            |              |               |               |               |
          |
GCC CCC ATC GAG AAA ACC ATC TCC AAA GCC AAA GGG CAG CCC CGA GAA CCA CAG GTG TAC
CGG GGG TAG CTC TTT TGG TAG AGG TTT CGG TTT CCC GTC GGG GCT CTT GGT GTC CAC ATG
Ala Pro Ile Glu Lys Thr Ile Ser Lys Ala Lys Gly Gln Pro Arg Glu Pro Gln Val Tyr
341____________345____________________hFC DOMAIN_____355________________360

            1090        1100            1110            1120           1130
            1140
            |              |               |               |               |
          |
ACC CTG CCC CCA TCC CGG GAG GAG ATG ACC AAG AAC CAG GTC AGC CTG ACC TGC CTG GTC
TGG GAC GGG GGT AGG GCC CTC CTC TAC TGG TTC TTG GTC CAG TCG GAC TGG ACG GAC CAG
Thr Leu Pro Pro Ser Arg Glu Glu Met Thr Lys Asn Gln Val Ser Leu Thr Cys Leu Val
361____________365____________________hFC DOMAIN_____375________________380

            1150        1160            1170            1180           1190
            1200
            |              |               |               |               |
          |
AAA GGC TTC TAT CCC AGC GAC ATC GCC GTG GAG TGG GAG AGC AAT GGG CAG CCG GAG AAC
TTT CCG AAG ATA GGG TCG CTG TAG CGG CAC CTC ACC CTC TCG TTA CCC GTC GGC CTC TTG
Lys Gly Phe Tyr Pro Ser Asp Ile Ala Val Glu Trp Glu Ser Asn Gly Gln Pro Glu Asn
```

-continued

```
VEGF-Grab3

381____________385____________________hFC DOMAIN______395________________400

            1210        1220            1230            1240           1250
            1260
            |              |               |               |               |
          |
AAC TAC AAG ACC ACG CCT CCC GTG CTG GAC TCC GAC GGC TCC TTC TTC CTC TAC AGC AAG
TTG ATG TTC TGG TGC GGA GGG CAC GAC CTG AGG CTG CCG AGG AAG AAG GAG ATG TCG TTC
Asn Tyr Lys Tyr Tyr Pro Pro Val Leu Asp Ser Asp Gly Ser Phe Phe Leu Tyr Ser Lys
401____________405____________________hFC DOMAIN______415________________420

            1270        1280            1290            1300           1310
            1320
            |              |               |               |               |
          |
CTC ACC GTG GAC AAG AGC AGG TGG CAG CAG GGG AAC GTC TTC TCA TGC TCC GTG ATG CAT
GAG TGG CAC CTG TTC TCG TCC ACC GTC GTC CCC TTG CAG AAG AGT ACG AGG CAC TAC GTA
Lys Thr Val Asp Lys Ser Arg Trp Gln Gln Gly Asn Val Phe Ser Cys Ser Val Met His
421____________425____________________hFC DOMAIN______435________________440

            1330        1340            1350            1360           1370
            1377
            |              |               |               |               |
          |
GAG GCT CTG CAC AAC CAC TAC ACG CAG AAG AGC CTC TCC CTG TCT CCG GGT AAA TGA
(SEQ ID NO: 7)
CTC CGA GAC GTG TTG GTG ATG TGC GTC TTC TCG GAG AGG GAC AGA GGC CCA TTT ACT
Glu Ala Leu His Asn His Tyr Thr Gln Lys Ser Leu Ser Leu Ser Pro Gly Lys ***
(SEQ ID NO: 8)
441 ___________445____________________hFC DOMAIN______455_____________459
```

TABLE 5

| Primer sequences for site-directed mutagenesis | | |
|---|---|---|
| Mutation sites | | |
| R135S/K138T For VEGF-Grab1 and VEGF-Grab3 | Forward primer | 5'-AGCACACCAAGCCCAGTCACAT TACTTAGA-3' (SEQ ID NO: 9) |
| | Reverse primer | 5'-TCTAAGTAATGTGACTGGGCTT GGTGTGCT-3' (SEQ ID NO: 10) |

TABLE 5-continued

| Primer sequences for site-directed mutagenesis | | |
|---|---|---|
| Mutation sites | | |
| R172N For VEGF-Grab2 and VEGF-Grab3 | Forward primer | 5'-AATAAGAACGCTTCCGTAAGGCG ACGAATT-3' (SEQ ID NO: 11) |
| | Reverse primer | 5'-AATTCGTCGCCTTACGGAAGCGT TCTTATT-3' (SEQ ID NO: 12) |

TABLE 6

Primer sequences for Quantitative Real Time PCR

| Gene | Forward primer | Reverse primer |
|---|---|---|
| mGAPDH | GTCGTGGAGTCTACTGGTGTCTTCAC (SEQ ID NO: 13) | GTTGTCATATTTCTCGTGGTTCACACCC (SEQ ID NO: 14) |
| mVEGFA | GTCAGAGAGCAACATCACCATGCAG (SEQ ID NO: 15) | CTTTGG TCTGCATTCACATCTGCTG (SEQ ID NO: 16) |
| mPIGF | GATGCTGGTCATGAAGCTGTTC (SEQ ID NO: 17) | TCGTCTCC AGAATAGGTCTGCA (SEQ ID NO: 18) |
| mVEGF-C | CGTTCTCTGCCAGCAACATTACCAC (SEQ ID NO: 19) | CTTGTTGG GTCCACAGACATCATGG (SEQ ID NO: 20) |
| mPDGF-B | CACAGAGACTCCGTAGATGAAGATGGG (SEQ ID NO: 21) | CA CTCGGCGATTACAGCAGGCTCTG (SEQ ID NO: 22) |
| mVEGFR1 | GGCTCTACGACCTTAGACTGTCA (SEQ ID NO: 23) | TGCTGTTTCCTGGTCCTAAAATA (SEQ ID NO: 24) |
| mVEGFR2 | ACCAGAAGTAAAAGTGATCCCAGA (SEQ ID NO: 25) | TCCACCAAAAGATGGAGATAATTT (SEQ ID NO: 26) |
| mPDGFRα | CGACTCCAGATGGGAGTTCCC (SEQ ID NO: 27) | TGCCATCCACTTCACAGGCA (SEQ ID NO: 28) |

TABLE 6-continued

| Primer sequences for Quantitative Real Time PCR | | |
|---|---|---|
| Gene | Forward primer | Reverse primer |
| mPDGFRβ | AGCTACATGGCCCCTTATGA (SEQ ID NO: 29) | GGAT CCCAAAAGACCAGACA (SEQ ID NO: 30) |
| mBv8 | GCATGACAGGAGTCATCATTTT (SEQ ID NO: 31) | AAATGGCAGG ATATCAGGAAA (SEQ ID NO: 32) |
| mCCL2 | GAGCATCCACGTGTTGGCT (SEQ ID NO: 33) | TGGTGAATGAGTAGC AGCAGGT (SEQ ID NO: 34) |

TABLE 7

| Antibodies | | |
|---|---|---|
| Antibody | Clone | Source |
| Primary | | |
| Hamster anti-CD31 | Clone 2H8 | Millipore |
| FITC-conjugated mouse anti-α-SMA | Clone 1A4 | Sigma-Aldrich |
| Rat anti-PDGFRβ | APB5 | eBioscience |
| Rabbit anti-LYVE1 | Polyclonal | Angiobio |
| Rabbit anti-CD11b | EP1345Y | Millipore |
| Rabbit anti-caspase3 | Polyclonal | R&D |
| Rabbit anti-collagen type IV | Polyclonal | Cosmobio |
| Mouse anti-pan-cytokeratin | AE1/AE3 | Abcam |
| Rat anti-cisplatin modified DNA | CP9/19 | Abcam |
| FITC-conjugated mouse anti-Hypoxyprobe-1 | 4.3.11.3 | Hypoxyprobe, Inc |
| Rabbit anti-phospho-VEGFR2 | 15D2 | Cell Signaling |
| Rabbit anti-VEGFR2 | D5B1 | Cell Signaling |
| Rabbit anti-phospho-ERK1/2 | Polyclonal | Cell Signaling |
| Rabbit anti-ERK1/2 | Polyclonal | Cell Signaling |
| Secondary | | |
| FITC-conjugated anti-hamster IgG | Polyclonal | Jackson ImmunoResearch |
| Cy3-conjugated anti-hamster IgG | Polyclonal | Jackson ImmunoResearch |
| FITC-conjugated anti-rabbit IgG | Polyclonal | Jackson ImmunoResearch |
| Cy3-conjugated anti-rabbit IgG | Polyclonal | Jackson ImmunoResearch |
| Cy3-conjugated anti-rat IgG | Polyclonal | Jackson ImmunoResearch |
| Cy3-conjugated anti-mouse IgG | Polyclonal | Jackson ImmunoResearch |
| Cy3-conjugated anti-human Fc | Polyclonal | Jackson ImmunoResearch |
| Goat Fab fragment anti-mouse IgG | Polyclonal | Jackson ImmunoResearch |
| HRP-conjugated anti-human Fc | Polyclonal | Sigma Aldrich |

REFERENCES

1. Ferrara N, Alitalo K. Clinical applications of angiogenic growth factors and their inhibitors. Nature medicine 1999; 5(12):1359-64.
2. Sung H K, Michael I P, Nagy A. Multifaceted role of vascular endothelial growth factor signaling in adult tissue physiology: an emerging concept with clinical implications. Current opinion in hematology 2010; 17(3):206-12.
3. Egeblad M, Nakasone E S, Werb Z. Tumors as organs: complex tissues that interface with the entire organism. Developmental cell 2010; 18(6):884-901.
4. Olsson A K, Dimberg A, Kreuger J, Claesson-Welsh L. VEGF receptor signalling—in control of vascular function. Nature reviews Molecular cell biology 2006; 7(5): 359-71.
5. Ferrara N, Hillan K J, Gerber H P, Novotny W. Discovery and development of bevacizumab, an anti-VEGF antibody for treating cancer. Nature reviews Drug discovery 2004; 3(5):391-400.
6. Holash J, Davis S, Papadopoulos N, Croll S D, Ho L, Russell M, et al. VEGF-Trap: a VEGF blocker with potent antitumor effects. Proceedings of the National Academy of Sciences of the United States of America 2002; 99(17): 11393-8.
7. Shibuya M. Vascular endothelial growth factor and its receptor system: physiological functions in angiogenesis and pathological roles in various diseases. Journal of biochemistry 2013; 153(1):13-9.
8. Sullivan L A, Carbon J G, Roland C L, Toombs J E, Nyquist-Andersen M, Kavlie A, et al. r84, a novel therapeutic antibody against mouse and human VEGF with potent anti-tumor activity and limited toxicity induction. PloS one 2010; 5(8):e12031.
9. Bergers G, Hanahan D. Modes of resistance to anti-angiogenic therapy. Nature reviews Cancer 2008; 8(8): 592-603.
10. Potente M, Gerhardt H, Carmeliet P. Basic and therapeutic aspects of angiogenesis. Cell 2011; 146(6):873-87.
11. Mancuso M R, Davis R, Norberg S M, O'Brien S, Sennino B, Nakahara T, et al. Rapid vascular regrowth in tumors after reversal of VEGF inhibition. The Journal of clinical investigation 2006; 116(10):2610-21.
12. Pascolini D, Mariotti S P, Pokharel G P, Pararajasegaram R, Etya'ale D, Negrel A D, et al. 2002 global update of available data on visual impairment: a compilation of population-based prevalence studies. Ophthalmic epidemiology 2004; 11(2):67-115.
13. Campochiaro P A, Soloway P, Ryan S J, Miller J W. The pathogenesis of choroidal neovascularization in patients with age-related macular degeneration. Molecular vision 1999; 5:34.
14. van Wijngaarden P, Coster D J, Williams K A. Inhibitors of ocular neovascularization: promises and potential problems. Jama 2005; 293(12):1509-13.
15. Jager R D, Mieler W F, Miller J W. Age-related macular degeneration. The New England journal of medicine 2008; 358(24):2606-17.
16. Group C R, Martin D F, Maguire M G, Ying G S, Grunwald J E, Fine S L, et al. Ranibizumab and bevacizumab for neovascular age-related macular degeneration. The New England journal of medicine 2011; 364(20): 1897-908.
17. Davis-Smyth T, Chen H, Park J, Presta L G, Ferrara N. The second immunoglobulin-like domain of the VEGF tyrosine kinase receptor Flt-1 determines ligand binding and may initiate a signal transduction cascade. The EMBO journal 1996; 15(18):4919-27.
18. Fischer C, Jonckx B, Mazzone M, Zacchigna S, Loges S, Pattarini L, et al. Anti-PlGF inhibits growth of VEGF (R)-inhibitor-resistant tumors without affecting healthy vessels. Cell 2007; 131(3):463-75.

19. Fischer C, Mazzone M, Jonckx B, Carmeliet P. FLT1 and its ligands VEGFB and PlGF: drug targets for anti-angiogenic therapy? Nature reviews Cancer 2008; 8(12): 942-56.

20. Adini A, Kornaga T, Firoozbakht F, Benjamin L E. Placental growth factor is a survival factor for tumor endothelial cells and macrophages. Cancer research 2002; 62(10):2749-52.

21. Laurent J, Hull E F, Touvrey C, Kuonen F, Lan Q, Lorusso G, et al. Proangiogenic factor PlGF programs CD11b(+) myelomonocytes in breast cancer during differentiation of their hematopoietic progenitors. Cancer research 2011; 71(11):3781-91.

22. Anisimov A, Leppanen V M, Tvorogov D, Zarkada G, Jeltsch M, Holopainen T, et al. The basis for the distinct biological activities of vascular endothelial growth factor receptor-1 ligands. Science signaling 2013; 6(282):ra52.

23. Elliott S, Lorenzini T, Asher S, Aoki K, Brankow D, Buck L, et al. Enhancement of therapeutic protein in vivo activities through glycoengineering. Nature biotechnology 2003; 21(4):414-21.

24. Egrie J C, Browne J K. Development and characterization of novel erythropoiesis stimulating protein (NESP). Nephrology, dialysis, transplantation: official publication of the European Dialysis and Transplant Association—European Renal Association 2001; 16 Suppl 3:3-13.

25. Ratner M. Genentech's glyco-engineered antibody to succeed Rituxan. Nature biotechnology 2014; 32(1):6-7.

26. Jung K, Lee D, Lim H S, Lee S I, Kim Y J, Lee G M, et al. Double anti-angiogenic and anti-inflammatory protein Valpha targeting VEGF-A and TNF-alpha in retinopathy and psoriasis. The Journal of biological chemistry 2011; 286(16):14410-8.

27. Kim J Y, Kim Y G, Lee G M. CHO cells in biotechnology for production of recombinant proteins: current state and further potential. Applied microbiology and biotechnology 2012; 93 (3): 917-30.

28. Koh Y J, Kim H Z, Hwang S I, Lee J E, Oh N, Jung K, et al. Double antiangiogenic protein, DAAP, targeting VEGF-A and angiopoietins in tumor angiogenesis, metastasis, and vascular leakage. Cancer cell 2010; 18(2):171-84.

29. Kronewitter S R, de Leoz M L, Peacock K S, McBride K R, An H J, Miyamoto S, et al. Human serum processing and analysis methods for rapid and reproducible N-glycan mass profiling. Journal of proteome research 2010; 9(10): 4952-9.

30. Kim C, Yang H, Fukushima Y, Saw P E, Lee J, Park J S, et al. Vascular RhoJ is an effective and selective target for tumor angiogenesis and vascular disruption. Cancer cell 2014; 25(1):102-17.

31. Smith L, Wesolowski E, McLellan A, Kostyk S K, D'Amato R, Sullivan R, et al. Oxygen-induced retinopathy in the mouse. Investigative ophthalmology & visual science 1994; 35(1):101-11.

32. Yang Z, Lasker K, Schneidman-Duhovny D, Webb B, Huang C C, Pettersen E F, et al. UCSF Chimera, MODELLER, and IMP: an integrated modeling system. Journal of structural biology 2012; 179(3):269-78.

33. Sola R J, Griebenow K. Effects of glycosylation on the stability of protein pharmaceuticals. Journal of pharmaceutical sciences 2009; 98(4):1223-45.

34. Hua S, Hu C Y, Kim B J, Totten S M, Oh M J, Yun N, et al. Glyco-analytical multispecific proteolysis (Glyco-AMP): a simple method for detailed and quantitative Glycoproteomic characterization. Journal of proteome research 2013; 12(10):4414-23.

35. Jung K, Lee J E, Kim H Z, Kim H M, Park B S, Hwang S I, et al. Toll-like receptor 4 decoy, TOY, attenuates gram-negative bacterial sepsis. PloS one 2009; 4(10): e7403.

36. Shojaei F, Wu X, Malik A K, Zhong C, Baldwin M E, Schanz S, et al. Tumor refractoriness to anti-VEGF treatment is mediated by CD11b+Gr1+ myeloid cells. Nature biotechnology 2007; 25(8):911-20.

37. Murdoch C, Muthana M, Coffelt S B, Lewis C E. The role of myeloid cells in the promotion of tumour angiogenesis. Nature reviews Cancer 2008; 8(8):618-31.

38. Shojaei F, Wu X, Zhong C, Yu L, Liang X H, Yao J, et al. Bv8 regulates myeloid-cell-dependent tumour angiogenesis. Nature 2007; 450(7171):825-31.

39. Qian B Z, Li J, Zhang H, Kitamura T, Zhang J, Campion L R, et al. CCL2 recruits inflammatory monocytes to facilitate breast-tumour metastasis. Nature 2011; 475 (7355):222-5.

40. Kabbinavar F, Hurwitz H I, Fehrenbacher L, Meropol N J, Novotny W F, Lieberman G, et al. Phase II, randomized trial comparing bevacizumab plus fluorouracil (FU)/leucovorin (LV) with FU/LV alone in patients with metastatic colorectal cancer. Journal of clinical oncology: official journal of the American Society of Clinical Oncology 2003; 21(1):60-5.

41. Lin E Y, Jones J G, Li P, Zhu L, Whitney K D, Muller W J, et al. Progression to malignancy in the polyoma middle T oncoprotein mouse breast cancer model provides a reliable model for human diseases. The American journal of pathology 2003; 163(5):2113-26.

42. Kuo C J, Farnebo F, Yu E Y, Christofferson R, Swearingen R A, Carter R, et al. Comparative evaluation of the antitumor activity of antiangiogenic proteins delivered by gene transfer. Proceedings of the National Academy of Sciences of the United States of America 2001; 98(8): 4605-10.

43. Bork K, Horstkorte R, Weidemann W. Increasing the sialylation of therapeutic glycoproteins: the potential of the sialic acid biosynthetic pathway. Journal of pharmaceutical sciences 2009; 98(10):3499-508.

44. des Guetz G, Uzzan B, Chouahnia K, Morere J F. Cardiovascular toxicity of anti-angiogenic drugs. Targeted oncology 2011; 6(4):197-202.

45. Michael I P, Westenskow P D, Hacibekiroglu S, Greenwald A C, Ballios B G, Kurihara T, et al. Local acting Sticky-trap inhibits vascular endothelial growth factor dependent pathological angiogenesis in the eye. EMBO molecular medicine 2014; 6(5):604-23.

46. Stewart M W. Aflibercept (VEGF Trap-eye): the newest anti-VEGF drug. The British journal of ophthalmology 2012; 96(9):1157-8.

47. Heier J S, Brown D M, Chong V, Korobelnik J F, Kaiser P K, Nguyen Q D, et al. Intravitreal aflibercept (VEGF trap-eye) in wet age-related macular degeneration. Ophthalmology 2012; 119(12):2537-48.

What is claimed is:

1. A VEGF decoy fusion polypeptide that synchronously binds to VEGF polypeptide and placenta growth factor (PIGF) polypeptide, comprising parental VEGFR1 second and third immunoglobulin (Ig)-like domains, wherein at least one positive amino acid residue in the third domain of VEGFR1 is mutated to a negatively charged residue so as to comprise a glycosylation site.

2. The polypeptide according to claim 1, which is linked to a multimerizing component.

3. The polypeptide according to claim 1, wherein the amino acid residue is on the β1-β2 loop, which comprises amino acid residues that are expressed from nucleic acid positions 397 to 432 of SEQ ID NO:1 corresponding to amino acid residues 133 to 144 of SEQ ID NO: 2, or β3-β4 loop, which comprises amino acid residues that are expressed from nucleic acid positions 490 to 522 of SEQ ID NO:1 corresponding to amino acid residues 164 to 174 of SEQ ID NO: 2.

4. The polypeptide according to claim 3, wherein the residue to be mutated is R135 residue on the β1-β2 loop, K138 residue on the β1-β2 loop, or R172 residue on the β3-β4 loop on the third domain.

5. The polypeptide according to claim 4, wherein the residue to be mutated is R135 residue on the β1-β2 loop and K138 residue on the β1-β2 loop on the third domain.

6. The polypeptide according to claim 4, wherein the residue to be mutated is R135 residue on the β1-β2 loop, K138 residue on the β1-β2 loop, and R172 residue on the β3-β4 loop on the third domain.

7. The polypeptide according to claim 1, wherein the polypeptide is glycosylated.

8. The polypeptide according to claim 1, wherein the polypeptide is sialylated.

9. The polypeptide according to claim 1, wherein the polypeptide exhibits a decrease in net pI of the polypeptide compared to that which has not been mutated.

* * * * *

SEQUENCE LISTING

<160> NUMBER OF SEQ ID NOS: 35

<210> SEQ ID NO 1
<211> LENGTH: 1377
<212> TYPE: DNA
<213> ORGANISM: Artificial Sequence
<220> FEATURE:
<223> OTHER INFORMATION: VEGF-Grab Backbone

<400> SEQUENCE: 1

```
atggtcagct actgggacac cggggtcctg ctgtgcgcgc tgctcagctg tctgcttctc     60

acaggatcta gttcaggtga attcggtaga cctttcgtag agatgtacag tgaaatcccc    120

gaaattatac acatgactga aggaagggag ctcgtcattc cctgccgggt tacgtcacct    180

aacatcactg ttactttaaa aaagtttcca cttgacactt tgatccctga tggaaaacgc    240

ataatctggg acagtagaaa gggcttcatc atatcaaatg caacgtacaa agaaataggg    300

cttctgacct gtgaagcaac agtcaatggg catttgtata agacaaacta tctcacacat    360

cgacaaacca atacaatcat agatgtccaa ataagcacac cacgcccagt caaattactt    420

agaggccata ctcttgtcct caattgtact gctaccactc ccttgaacac gagagttcaa    480

atgacctgga gttaccctga tgaaaaaaat aagagagctt ccgtaaggcg acgaattgac    540

caaagcaatt cccatgccaa catattctac agtgttctta ctattgacaa aatgcagaac    600

aaagacaaag gactttatac ttgtcgtgta aggagtggac catcattcaa atctgttaac    660

acctcagtgc atatatatga taaagcactc gaggacaaaa ctcacacatg cccaccgtgc    720

ccagcacctg aactcctggg gggaccgtca gtcttcctct tccccccaaa acccaaggac    780

accctcatga tctcccggac ccctgaggtc acatgcgtgg tggtggacgt gagccacgaa    840

gaccctgagg tcaagttcaa ctggtacgtg gacggcgtgg aggtgcataa tgccaagaca    900

aagccgcggg aggagcagta caacagcacg taccgtgtgg tcagcgtcct caccgtcctg    960

caccaggact ggctgaatgg caaggagtac aagtgcaagg tctccaacaa agccctccca   1020

gcccccatcg agaaaaccat ctccaaagcc aaagggcagc cccgagaacc acaggtgtac   1080

accctgcccc catcccggga ggagatgacc aagaaccagg tcagcctgac ctgcctggtc   1140

aaaggcttct atcccagcga catcgccgtg gagtgggaga gcaatgggca gccggagaac   1200

aactacaaga ccacgcctcc cgtgctggac tccgacggct ccttcttcct ctacagcaag   1260

ctcaccgtgg acaagagcag gtggcagcag gggaacgtct tctcatgctc cgtgatgcat   1320

gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: Artificial Sequence
<220> FEATURE:
<223> OTHER INFORMATION: VEGF-Grab Backbone

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Glu Phe Gly Arg Pro Phe
            20                  25                  30

Val Glu Met Tyr Ser Glu Ile Pro Glu Ile Ile His Met Tyr Glu Gly
        35                  40                  45

Arg Glu Leu Val Ile Pro Cys Arg Val Thr Ser Pro Asn Ile Thr Val
    50                  55                  60
```

-continued

```
Thr Leu Lys Lys Phe Pro Leu Asp Thr Leu Ile Pro Asp Gly Lys Arg
65                  70                  75                  80

Ile Ile Trp Asp Ser Arg Lys Gly Phe Ile Ile Ser Asn Ala Thr Tyr
                85                  90                  95

Lys Glu Ile Gly Leu Leu Thr Cys Glu Ala Thr Val Asn Gly His Leu
            100                 105                 110

Tyr Lys Thr Asn Tyr Leu Thr His Arg Gln Thr Asn Thr Ile Ile Asp
        115                 120                 125

Val Gln Ile Ser Thr Pro Arg Pro Val Lys Leu Leu Arg Gly His Thr
    130                 135                 140

Leu Val Leu Asn Cys Thr Arg Thr Thr Pro Leu Asn Thr Arg Val Gln
145                 150                 155                 160

Met Thr Trp Ser Tyr Pro Asp Glu Lys Asn Lys Arg Ala Ser Val Arg
                165                 170                 175

Arg Arg Ile Asp Gln Ser Asn Ser His Ala Asn Ile Phe Tyr Ser Val
            180                 185                 190

Leu Thr Ile Asp Lys Met Gln Asn Lys Asp Lys Gly Leu Tyr Thr Cys
        195                 200                 205

Arg Val Arg Ser Gly Pro Ser Phe Lys Ser Val Asn Thr Ser Val His
    210                 215                 220

Ile Tyr Asp Lys Ala Leu Glu Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Tyr Tyr Pro Pro Val Leu Asp Ser Asp Gly Ser Phe Phe
                405                 410                 415

Leu Tyr Ser Lys Lys Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 3
<211> LENGTH: 1377

-continued

<212> TYPE: DNA
<213> ORGANISM: Artificial Sequence
<220> FEATURE:
<223> OTHER INFORMATION: VEGF-Grab1

<400> SEQUENCE: 3
atggtcagct actgggacac cggggtcctg ctgtgcgcgc tgctcagctg tctgcttctc 60
acaggatcta gttcaggtga attcggtaga cctttcgtag agatgtacag tgaaatcccc 120
gaaattatac acatgactga aggaagggag ctcgtcattc cctgccgggt tacgtcacct 180
aacatcactg ttactttaaa aaagtttcca cttgacactt tgatccctga tggaaaacgc 240
ataatctggg acagtagaaa gggcttcatc atatcaaatg caacgtacaa agaaataggg 300
cttctgacct gtgaagcaac agtcaatggg catttgtata agacaaacta tctcacacat 360
cgacaaacca atacaatcat agatgtccaa ataagcacac caagcccagt cacattactt 420
agaggccata ctcttgtcct caattgtact gctaccactc ccttgaacac gagagttcaa 480
atgacctgga gttaccctga tgaaaaaaat aagagagctt ccgtaaggcg acgaattgac 540
caaagcaatt cccatgccaa catattctac agtgttctta ctattgacaa aatgcagaac 600
aaagacaaag gactttatac ttgtcgtgta aggagtggac catcattcaa atctgttaac 660
acctcagtgc atatatatga taaagcactc gaggacaaaa ctcacacatg cccaccgtgc 720
ccagcacctg aactcctggg gggaccgtca gtcttcctct tccccccaaa acccaaggac 780
accctcatga tctcccggac ccctgaggtc acatgcgtgg tggtggacgt gagccacgaa 840
gaccctgagg tcaagttcaa ctggtacgtg gacggcgtgg aggtgcataa tgccaagaca 900
aagccgcggg aggagcagta caacagcacg taccgtgtgg tcagcgtcct caccgtcctg 960
caccaggact ggctgaatgg caaggagtac aagtgcaagg tctccaacaa agccctccca 1020
gcccccatcg agaaaaccat ctccaaagcc aaagggcagc cccgagaacc acaggtgtac 1080
accctgcccc catcccggga ggagatgacc aagaaccagg tcagcctgac ctgcctggtc 1140
aaaggcttct atcccagcga catcgccgtg gagtgggaga gcaatgggca gccggagaac 1200
aactacaaga ccacgcctcc cgtgctggac tccgacggct ccttcttcct ctacagcaag 1260
ctcaccgtgg acaagagcag gtggcagcag gggaacgtct tctcatgctc cgtgatgcat 1320
gaggctctgc acaaccacta cacgcagaag agcctctccc tgtctccggg taaatga 1377

<210> SEQ ID NO 4
<211> LENGTH: 458
<212> TYPE: PRT
<213> ORGANISM: Artificial Sequence
<220> FEATURE:
<223> OTHER INFORMATION: VEGF-Grab1

<400> SEQUENCE: 4

Met Val Ser Tyr Trp Asp Thr Gly Val Leu Leu Cys Ala Leu Leu Ser
1 5 10 15

Cys Leu Leu Leu Thr Gly Ser Ser Ser Gly Glu Phe Gly Arg Pro Phe
20 25 30

Val Glu Met Tyr Ser Glu Ile Pro Glu Ile Ile His Met Tyr Glu Gly
35 40 45

Arg Glu Leu Val Ile Pro Cys Arg Val Thr Ser Pro Asn Ile Thr Val
50 55 60

Thr Leu Lys Lys Phe Pro Leu Asp Thr Leu Ile Pro Asp Gly Lys Arg
65 70 75 80

Ile Ile Trp Asp Ser Arg Lys Gly Phe Ile Ile Ser Asn Ala Thr Tyr

-continued 85 90 95

Lys Glu Ile Gly Leu Leu Thr Cys Glu Ala Thr Val Asn Gly His Leu
100 105 110

Tyr Lys Thr Asn Tyr Leu Thr His Arg Gln Thr Asn Thr Ile Ile Asp
115 120 125

Val Gln Ile Ser Thr Pro Ser Pro Val Thr Leu Leu Arg Gly His Thr
130 135 140

Leu Val Leu Asn Cys Thr Arg Thr Thr Pro Leu Asn Thr Arg Val Gln
145 150 155 160

Met Thr Trp Ser Tyr Pro Asp Glu Lys Asn Lys Arg Ala Ser Val Arg
165 170 175

Arg Arg Ile Asp Gln Ser Asn Ser His Ala Asn Ile Phe Tyr Ser Val
180 185 190

Leu Thr Ile Asp Lys Met Gln Asn Lys Asp Lys Gly Leu Tyr Thr Cys
195 200 205

Arg Val Arg Ser Gly Pro Ser Phe Lys Ser Val Asn Thr Ser Val His
210 215 220

Ile Tyr Asp Lys Ala Leu Glu Asp Lys Thr His Thr Cys Pro Pro Cys
225 230 235 240

Pro Ala Pro Glu Leu Leu Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Asn Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Glu Glu
355 360 365

Met Thr Lys Asn Gln Val Ser Leu Thr Cys Leu Val Lys Gly Phe Tyr
370 375 380

Pro Ser Asp Ile Ala Val Glu Trp Glu Ser Asn Gly Gln Pro Glu Asn
385 390 395 400

Asn Tyr Lys Tyr Tyr Pro Pro Val Leu Asp Ser Asp Gly Ser Phe Phe
405 410 415

Leu Tyr Ser Lys Lys Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Gly Lys
450 455

<210> SEQ ID NO 5
<211> LENGTH: 1377
<212> TYPE: DNA
<213> ORGANISM: Artificial Sequence
<220> FEATURE:
<223> OTHER INFORMATION: VEGF-Grab2

<400> SEQUENCE: 5

```
atggtcagct actgggacac cggggtcctg ctgtgcgcgc tgctcagctg tctgcttctc     60
acaggatcta gttcaggtga attcggtaga cctttcgtag agatgtacag tgaaatcccc    120
gaaattatac acatgactga aggaagggag ctcgtcattc cctgccgggt tacgtcacct    180
aacatcactg ttactttaaa aaagtttcca cttgacactt tgatccctga tggaaaacgc    240
ataatctggg acagtagaaa gggcttcatc atatcaaatg caacgtacaa agaaataggg    300
cttctgacct gtgaagcaac agtcaatggg catttgtata agacaaacta tctcacacat    360
cgacaaacca atacaatcat agatgtccaa ataagcacac cacgcccagt caaattactt    420
agaggccata ctcttgtcct caattgtact gctaccactc ccttgaacac gagagttcaa    480
atgacctgga gttaccctga tgaaaaaaat aagaacgctt ccgtaaggcg acgaattgac    540
caaagcaatt cccatgccaa catattctac agtgttctta ctattgacaa aatgcagaac    600
aaagacaaag gactttatac ttgtcgtgta aggagtggac catcattcaa atctgttaac    660
acctcagtgc atatatatga taaagcactc gaggacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga ggagatgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 6
<211> LENGTH: 458
<212> TYPE: PRT
<213> ORGANISM: Artificial Sequence
<220> FEATURE:
<223> OTHER INFORMATION: VEGF-Grab2

<400> SEQUENCE: 6

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Glu Phe Gly Arg Pro Phe
            20                  25                  30

Val Glu Met Tyr Ser Glu Ile Pro Glu Ile Ile His Met Tyr Glu Gly
        35                  40                  45

Arg Glu Leu Val Ile Pro Cys Arg Val Thr Ser Pro Asn Ile Thr Val
    50                  55                  60

Thr Leu Lys Lys Phe Pro Leu Asp Thr Leu Ile Pro Asp Gly Lys Arg
65                  70                  75                  80

Ile Ile Trp Asp Ser Arg Lys Gly Phe Ile Ile Ser Asn Ala Thr Tyr
                85                  90                  95

Lys Glu Ile Gly Leu Leu Thr Cys Glu Ala Thr Val Asn Gly His Leu
            100                 105                 110
```

-continued

```
Tyr Lys Thr Asn Tyr Leu Thr His Arg Gln Thr Asn Thr Ile Ile Asp
        115                 120                 125

Val Gln Ile Ser Thr Pro Arg Pro Val Lys Leu Leu Arg Gly His Thr
    130                 135                 140

Leu Val Leu Asn Cys Thr Arg Thr Thr Pro Leu Asn Thr Arg Val Gln
145                 150                 155                 160

Met Thr Trp Ser Tyr Pro Asp Glu Lys Asn Lys Asn Ala Ser Val Arg
                165                 170                 175

Arg Arg Ile Asp Gln Ser Asn Ser His Ala Asn Ile Phe Tyr Ser Val
            180                 185                 190

Leu Thr Ile Asp Lys Met Gln Asn Lys Asp Lys Gly Leu Tyr Thr Cys
        195                 200                 205

Arg Val Arg Ser Gly Pro Ser Phe Lys Ser Val Asn Thr Ser Val His
    210                 215                 220

Ile Tyr Asp Lys Ala Leu Glu Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Tyr Tyr Pro Pro Val Leu Asp Ser Asp Gly Ser Phe Phe
                405                 410                 415

Leu Tyr Ser Lys Lys Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 7
<211> LENGTH: 1377
<212> TYPE: DNA
<213> ORGANISM: Artificial Sequence
<220> FEATURE:
<223> OTHER INFORMATION: VEGF-Grab3

<400> SEQUENCE: 7

```
atggtcagct actgggacac cggggtcctg ctgtgcgcgc tgctcagctg tctgcttctc      60

acaggatcta gttcaggtga attcggtaga cctttcgtag agatgtacag tgaaatcccc     120
```

```
gaaattatac acatgactga aggaagggag ctcgtcattc cctgccgggt tacgtcacct    180

aacatcactg ttactttaaa aaagtttcca cttgacactt tgatccctga tggaaaacgc    240

ataatctggg acagtagaaa gggcttcatc atatcaaatg caacgtacaa agaaataggg    300

cttctgacct gtgaagcaac agtcaatggg catttgtata agacaaacta tctcacacat    360

cgacaaacca atacaatcat agatgtccaa ataagcacac caagcccagt cacattactt    420

agaggccata ctcttgtcct caattgtact gctaccactc ccttgaacac gagagttcaa    480

atgacctgga gttaccctga tgaaaaaaat aagaacgctt ccgtaaggcg acgaattgac    540

caaagcaatt cccatgccaa catattctac agtgttctta ctattgacaa aatgcagaac    600

aaagacaaag gactttatac ttgtcgtgta aggagtggac catcattcaa atctgttaac    660

acctcagtgc atatatatga taaagcactc gaggacaaaa ctcacacatg cccaccgtgc    720

ccagcacctg aactcctggg gggaccgtca gtcttcctct tccccccaaa acccaaggac    780

accctcatga tctcccggac ccctgaggtc acatgcgtgg tggtggacgt gagccacgaa    840

gaccctgagg tcaagttcaa ctggtacgtg gacggcgtgg aggtgcataa tgccaagaca    900

aagccgcggg aggagcagta caacagcacg taccgtgtgg tcagcgtcct caccgtcctg    960

caccaggact ggctgaatgg caaggagtac aagtgcaagg tctccaacaa agccctccca   1020

gcccccatcg agaaaaccat ctccaaagcc aaagggcagc cccgagaacc acaggtgtac   1080

accctgcccc catcccggga ggagatgacc aagaaccagg tcagcctgac ctgcctggtc   1140

aaaggcttct atcccagcga catcgccgtg gagtgggaga gcaatgggca gccggagaac   1200

aactacaaga ccacgcctcc cgtgctggac tccgacggct ccttcttcct ctacagcaag   1260

ctcaccgtgg acaagagcag gtggcagcag gggaacgtct tctcatgctc cgtgatgcat   1320

gaggctctgc acaaccacta cacgcagaag agcctctccc tgtctccggg taaatga      1377
```

<210> SEQ ID NO 8
<211> LENGTH: 458
<212> TYPE: PRT
<213> ORGANISM: Artificial Sequence
<220> FEATURE:
<223> OTHER INFORMATION: VEGF-Grab3

<400> SEQUENCE: 8

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Glu Phe Gly Arg Pro Phe
            20                  25                  30

Val Glu Met Tyr Ser Glu Ile Pro Glu Ile Ile His Met Tyr Glu Gly
        35                  40                  45

Arg Glu Leu Val Ile Pro Cys Arg Val Thr Ser Pro Asn Ile Thr Val
    50                  55                  60

Thr Leu Lys Lys Phe Pro Leu Asp Thr Leu Ile Pro Asp Gly Lys Arg
65                  70                  75                  80

Ile Ile Trp Asp Ser Arg Lys Gly Phe Ile Ile Ser Asn Ala Thr Tyr
                85                  90                  95

Lys Glu Ile Gly Leu Leu Thr Cys Glu Ala Thr Val Asn Gly His Leu
            100                 105                 110

Tyr Lys Thr Asn Tyr Leu Thr His Arg Gln Thr Asn Thr Ile Ile Asp
        115                 120                 125

Val Gln Ile Ser Thr Pro Ser Pro Val Thr Leu Leu Arg Gly His Thr
    130                 135                 140
```

```
Leu Val Leu Asn Cys Thr Arg Thr Thr Pro Leu Asn Thr Arg Val Gln
145                 150                 155                 160

Met Thr Trp Ser Tyr Pro Asp Glu Lys Asn Lys Asn Ala Ser Val Arg
                165                 170                 175

Arg Arg Ile Asp Gln Ser Asn Ser His Ala Asn Ile Phe Tyr Ser Val
            180                 185                 190

Leu Thr Ile Asp Lys Met Gln Asn Lys Asp Lys Gly Leu Tyr Thr Cys
        195                 200                 205

Arg Val Arg Ser Gly Pro Ser Phe Lys Ser Val Asn Thr Ser Val His
    210                 215                 220

Ile Tyr Asp Lys Ala Leu Glu Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Tyr Tyr Pro Pro Val Leu Asp Ser Asp Gly Ser Phe Phe
                405                 410                 415

Leu Tyr Ser Lys Lys Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 9
<211> LENGTH: 30
<212> TYPE: DNA
<213> ORGANISM: Artificial Sequence
<220> FEATURE:
<223> OTHER INFORMATION: Forward primer - R135S/K138T for VEGF-Grab1 and
      VEGF-Grab3

<400> SEQUENCE: 9

agcacaccaa gcccagtcac attacttaga                                    30


<210> SEQ ID NO 10
<211> LENGTH: 30
<212> TYPE: DNA
<213> ORGANISM: Artificial Sequence
```

-continued

```
<220> FEATURE:
<223> OTHER INFORMATION: Reverse Primer - R135S/K138T for VEGF-Grab1 and
      VEGF-Grab3

<400> SEQUENCE: 10

tctaagtaat gtgactgggc ttggtgtgct                                        30


<210> SEQ ID NO 11
<211> LENGTH: 30
<212> TYPE: DNA
<213> ORGANISM: Artificial Sequence
<220> FEATURE:
<223> OTHER INFORMATION: Forward primer - R172N for VEGF-Grab2 and
      VEGF-Grab3

<400> SEQUENCE: 11

aataagaacg cttccgtaag gcgacgaatt                                        30


<210> SEQ ID NO 12
<211> LENGTH: 30
<212> TYPE: DNA
<213> ORGANISM: Artificial Sequence
<220> FEATURE:
<223> OTHER INFORMATION: Reverse primer - R172N for VEGF-Grab2 and
      VEGF-Grab3

<400> SEQUENCE: 12

aattcgtcgc cttacggaag cgttcttatt                                        30


<210> SEQ ID NO 13
<211> LENGTH: 26
<212> TYPE: DNA
<213> ORGANISM: Artificial Sequence
<220> FEATURE:
<223> OTHER INFORMATION: Forward primer - mGAPDH

<400> SEQUENCE: 13

gtcgtggagt ctactggtgt cttcac                                            26


<210> SEQ ID NO 14
<211> LENGTH: 28
<212> TYPE: DNA
<213> ORGANISM: Artificial Sequence
<220> FEATURE:
<223> OTHER INFORMATION: Reverse primer - mGAPDH

<400> SEQUENCE: 14

gttgtcatat ttctcgtggt tcacaccc                                          28


<210> SEQ ID NO 15
<211> LENGTH: 25
<212> TYPE: DNA
<213> ORGANISM: Artificial Sequence
<220> FEATURE:
<223> OTHER INFORMATION: Forward primer - mVEGFA

<400> SEQUENCE: 15

gtcagagagc aacatcacca tgcag                                             25


<210> SEQ ID NO 16
<211> LENGTH: 25
<212> TYPE: DNA
<213> ORGANISM: Artificial Sequence
<220> FEATURE:
<223> OTHER INFORMATION: Reverse primer - mVEGFA

<400> SEQUENCE: 16
```

ctttggtctg cattcacatc tgctg 25

<210> SEQ ID NO 17
<211> LENGTH: 22
<212> TYPE: DNA
<213> ORGANISM: Artificial Sequence
<220> FEATURE:
<223> OTHER INFORMATION: Forward primer - mPlGF

<400> SEQUENCE: 17
gatgctggtc atgaagctgt tc 22

<210> SEQ ID NO 18
<211> LENGTH: 22
<212> TYPE: DNA
<213> ORGANISM: Artificial Sequence
<220> FEATURE:
<223> OTHER INFORMATION: Reverse Primer- mPlGF

<400> SEQUENCE: 18
tcgtctccag aataggtctg ca 22

<210> SEQ ID NO 19
<211> LENGTH: 25
<212> TYPE: DNA
<213> ORGANISM: Artificial Sequence
<220> FEATURE:
<223> OTHER INFORMATION: Forward primer - mVEGF-C

<400> SEQUENCE: 19
cgttctctgc cagcaacatt accac 25

<210> SEQ ID NO 20
<211> LENGTH: 25
<212> TYPE: DNA
<213> ORGANISM: Artificial Sequence
<220> FEATURE:
<223> OTHER INFORMATION: Reverse Primer-  mVEGF-C

<400> SEQUENCE: 20
cttgttgggt ccacagacat catgg 25

<210> SEQ ID NO 21
<211> LENGTH: 27
<212> TYPE: DNA
<213> ORGANISM: Artificial Sequence
<220> FEATURE:
<223> OTHER INFORMATION: Forward primer - mPDGF-B

<400> SEQUENCE: 21
cacagagact ccgtagatga agatggg 27

<210> SEQ ID NO 22
<211> LENGTH: 25
<212> TYPE: DNA
<213> ORGANISM: Artificial Sequence
<220> FEATURE:
<223> OTHER INFORMATION: Reverse primer - mPDGF-B

<400> SEQUENCE: 22
cactcggcga ttacagcagg ctctg 25

<210> SEQ ID NO 23
<211> LENGTH: 23
<212> TYPE: DNA

-continued

<213> ORGANISM: Artificial Sequence
<220> FEATURE:
<223> OTHER INFORMATION: Forward primer - mVEGFR1

<400> SEQUENCE: 23
ggctctacga ccttagactg tca 23

<210> SEQ ID NO 24
<211> LENGTH: 23
<212> TYPE: DNA
<213> ORGANISM: Artificial Sequence
<220> FEATURE:
<223> OTHER INFORMATION: mVEGFR1

<400> SEQUENCE: 24
tgctgtttcc tggtcctaaa ata 23

<210> SEQ ID NO 25
<211> LENGTH: 24
<212> TYPE: DNA
<213> ORGANISM: Artificial Sequence
<220> FEATURE:
<223> OTHER INFORMATION: Forward Primer - mVEGFR2

<400> SEQUENCE: 25
accagaagta aaagtgatcc caga 24

<210> SEQ ID NO 26
<211> LENGTH: 24
<212> TYPE: DNA
<213> ORGANISM: Artificial Sequence
<220> FEATURE:
<223> OTHER INFORMATION: Reverse Primer - mVEGFR2

<400> SEQUENCE: 26
tccaccaaaa gatggagata attt 24

<210> SEQ ID NO 27
<211> LENGTH: 21
<212> TYPE: DNA
<213> ORGANISM: Artificial Sequence
<220> FEATURE:
<223> OTHER INFORMATION: Forward primer - mPDGFRalpha

<400> SEQUENCE: 27
cgactccaga tgggagttcc c 21

<210> SEQ ID NO 28
<211> LENGTH: 20
<212> TYPE: DNA
<213> ORGANISM: Artificial Sequence
<220> FEATURE:
<223> OTHER INFORMATION: Reverse primer - mPDGFRalpha

<400> SEQUENCE: 28
tgccatccac ttcacaggca 20

<210> SEQ ID NO 29
<211> LENGTH: 20
<212> TYPE: DNA
<213> ORGANISM: Artificial Sequence
<220> FEATURE:
<223> OTHER INFORMATION: Forward primer - mPDGFRbeta

<400> SEQUENCE: 29
agctacatgg ccccttatga 20

<210> SEQ ID NO 30
<211> LENGTH: 20
<212> TYPE: DNA
<213> ORGANISM: Artificial Sequence
<220> FEATURE:
<223> OTHER INFORMATION: Reverse primer - mPDGFRbeta

<400> SEQUENCE: 30
ggatcccaaa agaccagaca 20

<210> SEQ ID NO 31
<211> LENGTH: 22
<212> TYPE: DNA
<213> ORGANISM: Artificial Sequence
<220> FEATURE:
<223> OTHER INFORMATION: Forward primer - mBv8

<400> SEQUENCE: 31
gcatgacagg agtcatcatt tt 22

<210> SEQ ID NO 32
<211> LENGTH: 21
<212> TYPE: DNA
<213> ORGANISM: Artificial Sequence
<220> FEATURE:
<223> OTHER INFORMATION: Reverse primer - mBv8

<400> SEQUENCE: 32
aaatggcagg atatcaggaa a 21

<210> SEQ ID NO 33
<211> LENGTH: 19
<212> TYPE: DNA
<213> ORGANISM: Artificial Sequence
<220> FEATURE:
<223> OTHER INFORMATION: Forward primer - mCCL2

<400> SEQUENCE: 33
gagcatccac gtgttggct 19

<210> SEQ ID NO 34
<211> LENGTH: 22
<212> TYPE: DNA
<213> ORGANISM: Artificial Sequence
<220> FEATURE:
<223> OTHER INFORMATION: Reverse primer - mCCL2

<400> SEQUENCE: 34
tggtgaatga gtagcagcag gt 22

<210> SEQ ID NO 35
<211> LENGTH: 60
<212> TYPE: PRT
<213> ORGANISM: Artificial Sequence
<220> FEATURE:
<223> OTHER INFORMATION: VR1-Ig3

<400> SEQUENCE: 35

```
Leu Thr His Arg Gln Thr Asn Thr Ile Ile Asp Val Gln Ile Ser Thr
1               5                   10                  15

Pro Arg Pro Val Lys Leu Leu Arg Gly His Thr Leu Val Leu Asn Cys
            20                  25                  30

Thr Ala Thr Thr Pro Leu Asn Thr Arg Val Gln Met Thr Trp Ser Tyr
        35                  40                  45
```

-continued

```
Pro Asp Glu Lys Asn Lys Arg Ala Ser Val Arg Arg
    50                  55                  60
```